(12) United States Patent
Mikoshiba et al.

(10) Patent No.: US 8,017,809 B2
(45) Date of Patent: Sep. 13, 2011

(54) BISBORON COMPOUND

(75) Inventors: Katsuhiko Mikoshiba, Saitama (JP); Shoichiro Ozaki, Saitama (JP); Akinobu Suzuki, Saitama (JP); Takeshi Nakamura, Tokyo (JP); Kyoko Nakamura, legal representative, Tokyo (JP); Aiko Nakamura, legal representative, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 109 days.

(21) Appl. No.: 12/094,968

(22) PCT Filed: Nov. 24, 2006

(86) PCT No.: PCT/JP2006/323492
§ 371 (c)(1),
(2), (4) Date: Oct. 13, 2009

(87) PCT Pub. No.: WO2007/061074
PCT Pub. Date: May 31, 2007

(65) Prior Publication Data
US 2010/0087645 A1    Apr. 8, 2010

(30) Foreign Application Priority Data
Nov. 25, 2005    (JP) ................................. 2005-340864

(51) Int. Cl.
C07F 5/02    (2006.01)
A61K 31/69    (2006.01)
(52) U.S. Cl. ............................................. 568/3; 514/64
(58) Field of Classification Search .................. None
See application file for complete search history.

(56) References Cited

FOREIGN PATENT DOCUMENTS
WO    03/033002 A1    4/2003

OTHER PUBLICATIONS

I.G.C. Coutts, et al.; "Organoboron Compounds. Part IX.[1] Diborinic Acids and their Derivatives"; Journal of the Chemical Society, C: Organic; 1970; pp. 2225-2227; No. 16.

*Primary Examiner* — Brian J Davis
(74) *Attorney, Agent, or Firm* — Sughrue Mion, PLLC

(57) ABSTRACT

A bisboron compound represented by the general formula (I):

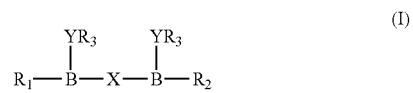

wherein B represents a boron atom, Y represents an oxygen or sulfur atom, $R_1$ and $R_2$ independently represent a monocyclic aromatic group, a polycyclic aromatic group, or a heterocyclic group containing at least one heteroatom selected from oxygen, nitrogen and sulfur atoms, $R_3$ represents a hydrogen atom; —$(CH_2)_m$—$NR_4R_5$; —CO—$(CH_2)_m$—$NR_4R_5$; —COCH$(NH_2)R_6$; —CHR$_7R_8$; —CH$_2$CH$(NH_2)$—$R_9$; quinolyl substituted with C1-C4 alkyl group; or C1-C4 alkyl substituted with pyridyl, piperidino or pyrrolidinyl group, and X represents a monocyclic aromatic group, a polycyclic aromatic group or a heterocyclic group, which may be the same as or different from $R_1$ and $R_2$, or a bifunctional group having a monocyclic aromatic group, polycyclic aromatic group or heterocyclic group bonded to each side of a group selected from the group consisting of a single bond, O, $CH_2$, S, $SO_2$, $CH_2OCH_2$, $OCH_2$, $OCH_2CH_2OCH_2$, $OCH_2OCH_2CH_2$ and $CH_2OCH_2CH_2$, or a salt thereof, and a composition for controlling the intracellular calcium concentration, which comprises the compound or salt thereof as an active ingredient.

17 Claims, No Drawings

BISBORON COMPOUND

CROSS-REFERENCE TO RELATED APPLICATIONS

This application is a National Stage of International Application No. PCT/JP2006/323492 filed Nov. 24, 2006, claiming priority based on Japanese Patent Application No. 2005-340864 filed Nov. 25, 2005, the contents of all of which are incorporated herein by reference in their entirety.

TECHNICAL FIELD

The present invention relates to a novel bisboron compound having activity to control the intracellular calcium concentration, and an intracellular calcium concentration control agent comprising the compound as an active ingredient.

BACKGROUND ART

Cells exhibit a wide variety of physiological functions in response to various exogenous stimuli such as neurotransmitters, hormones and growth factors. In this regard, calcium ions play an important role as a messenger for intracellular signaling. Main calcium sources are intracellular calcium stores and extracellular fluids. Calcium is released from an intracellular calcium store through an inositol 1,4,5-triphosphate ($IP_3$) receptor that is a second messenger or through a ryanodine receptor that is insensitive to $IP_3$ but releases calcium in accordance with an increase in the intracellular calcium concentration.

$IP_3$ as an intracellular second messenger carries out $IP_3$-induced calcium (Ca) release (IICR) to induce liberation of calcium ions from an intracellular calcium ion pool. An $IP_3$ receptor is an intracellular calcium ion release channel activated by binding to $IP_3$. The $IP_3$ receptor forms a gene family, exhibits various functions, tissue- or cell-specific expressions and intracellular localizations, and plays an essentially important role in the biological functions.

It is known that $IP_3$ is produced in a pathway of activating various receptors coupled with G-proteins or in a pathway of activating various receptors coupled with tyrosine kinase activity. Phospholipase C activated in the above pathway decomposes phosphatidylinositol 4,5-bisphosphate ($PIP_2$) into two second messengers, $IP_3$ and diacylglycerol (DG). $IP_3$ binds to an $IP_3$ receptor present in an intracellular calcium store to release calcium. On the other hand, DG together with the calcium activates protein kinase C to control various physiological functions.

It is known that various channels are involved in calcium ion entry from an extracellular fluid. The channels are roughly classified into voltage-dependent channels activated in accordance with the potential of a cell membrane and channels activated irrespective of the potential. Calcium permeable neurotransmitter receptors (such as NMDA receptors) are known as the latter channels. Recently, calcium permeable channels activated by activation of G-protein coupled receptors or tyrosine kinase receptors and receptor activated calcium channels (RACC) have been attracted attention. RACCs include capacitative calcium entry (CCE) channels, second messenger response channels and G-protein response channels.

A CCE channel is activated when calcium ions are released from and depleted in an intracellular calcium store, and has a function of allowing entry of extracellular calcium ions to refill the intracellular calcium store with calcium ions. For this reason, the CCE channel is also called store operated calcium entry channel (SOC).

The presence of this channel has been electrophysiologically revealed mainly in nonexcitable cells such as immunocytes, vascular endothelial cells and platelets, and the channel is known as a main calcium entry pathway in nonexcitable cells. However, the molecular entity of the channel has not been clear. Further, the mechanism of recognition of depletion in the intracellular calcium store and the mechanism of activation have not been clear.

However, it has been verified in the experiments shown below and the like that capacitative calcium entry and calcium release from the intracellular calcium store caused by involvement of the aforementioned $IP_3$ play an important role in expression of functions of cells.

(1) When platelets are stimulated by thromboxane $A_2$, thrombin or the like, the platelets are aggregated through $IP_3$ and thrombi are formed, resulting in ischemic heart or brain disease. In this regard, it is known that capacitative calcium entry subsequent to $IP_3$-induced calcium release (IICR) is also essential to platelet aggregation Biochimica et Biophysica Acta, 1082, 219-238 (1991); Platelets, 11(4), 215-21 (2000)].

(2) Helper T cells (Th1) of subset 1 in T-lymphocytes produce and secrete cytokines such as interleukin 2 (IL-2) and interferon γ in accordance with activation by antigen presenting cells to express IL-2 receptors. In this regard, NF-AT as an enhancer must become active and be transferred into nuclei in order to start transcription of IL-2 genes. It is known that an increase in the intracellular calcium concentration by capacitative calcium entry is essential for an activation of the NF-AT [J. Cell Biol., 131(3), 655-67 (1995)].

(3) $IP_3$ is produced and calcium is released by stimuli from leukotriene $D_4$ ($LTD_4$), angiotensin II or the like, so that bronchial smooth muscle and vascular smooth muscle contract to cause asthma, hypertension, cerebral vasospasm or the like. In this regard, it is known that capacitative calcium entry is also essential [J. Pharm. Exp. Ther., 244, 508-515 (1987); Protein Nucleic Acid and Enzyme, 36, 885-895 (1991); J. Membr. Biol., 155(1), 61-73 (1997)].

(4) In exocrine pancreatic cells, the intracellular calcium concentration is increased through $IP_3$ by stimuli from cholecystokinin, acetylcholine or the like and abnormal secretion of protease occurs to cause pancreatitis. In this regard, it is known that capacitative calcium entry is also essential [Pharmacology & Toxicology, 68, 83-87 (1991); Proc. Natl. Acad. Sci. USA, 97(24), 13126-13131 (2000)].

(5) Leukotriene $B_4$ ($LTB_4$) produced from neutrophils increases the intracellular calcium concentration through $IP_3$ and causes migration of the neutrophils to the inflammatory site to develop inflammation [ANN. NY. ACAD. Sci., 524, 187-195 (1988)]. $LTB_4$ production is also involved in expansion of the necrotic layer in myocardial infarction [J. Pharm. Exp. Ther., 228, 510-522 (1983)].

(6) In the kidneys, stimuli from angiotensin II, bradykinin or the like produce $IP_3$ and proliferate mesangial cells to cause glomerulonephritis. $IP_3$ also has an influence on various other renal diseases [Metabolism, 27, 413-425 (1990)].

In recent years, it has been clear that capacitative calcium entry has an important function not only in the nonexcitable cells described above but also in neurons. For example, it is known that presenilin known as a gene responsible for familial Alzheimer's disease has a function as γ-secretase cleaving amyloid precursor protein. It has been clear that capacitative calcium entry is abnormal in culture cells when expressing presenilin discovered in a familial Alzheimer's disease patient into which a point mutation is introduced [Neuron, 27(3), 561-72 (2000)]. It has also been clear that capacitative calcium entry is abnormal in an experiment using mouse-derived primary culture cells having presenilin genes destroyed [J. Cell Biol., 149(4), 793-8 (2000)].

As described above, endogenous calcium and capacitative calcium entry are extremely highly associated with various diseases.

Accordingly, it is assumed that endogenous calcium release inhibitors or capacitative calcium entry inhibitors have an action of inhibiting an increase in the intracellular calcium concentration and are therefore useful as prophylactic and/or therapeutic agents for diseases such as platelet aggregation, ischemic heart or brain disease, immunodeficiency, allergic disease, bronchial asthma, hypertension, cerebral vasospasm, various renal diseases, pancreatitis or Alzheimer's disease.

JP Patent No. 2987727 discloses (2-aminoethoxy)diphenylborane and tetraphenyldiboroxane (tetraphenyldiboroxide) having an effect of inhibiting calcium release from an endogenous calcium store by mechanisms of IICR and calcium induced calcium release (CICR).

It is also described that (2-aminoethoxy)diphenylborane has an SOC inhibitory action through an $IP_3$ receptor inhibitory action [Science, 287, 1647-1651 (2000)].

Further, WO 03/033002 describes that bis-1-oxaquinolizidine, xestospongin C, xestospongin A, araguspongin B and the like are useful as inhibitors for calcium channels through $IP_3$ receptors.

In such a situation, it can be greatly expected that a drug reducing the intracellular calcium concentration abnormally increased by $IP_3$ receptor activation or capacitative calcium entry is useful for prevention or treatment of the various above-described diseases caused by an increase in the intracellular calcium concentration, if such a drug can be developed.

To attain such an object, the present inventors have found a certain 2-APB derivative as an intracellular calcium concentration control agent having activity stronger than that of (2-aminoethoxy)diphenylborane (2-APB) and filed an international application (WO 03/033002).

DISCLOSURE OF THE INVENTION

An object of the present invention is to provide an intracellular calcium concentration control compound that physiologically inhibits extracellular calcium entry caused by calcium release through an $IP_3$ receptor in intracellular endoplasmic reticulum, which is called capacitative calcium entry (CCE).

The present inventors have found that a certain bisboron compound has intracellular calcium concentration control activity stronger than that of a monoboron compound such as 2-APB. This finding has led to the completion of the present invention.

Accordingly, in summary, the present invention has the following characteristics.

In a first aspect, the present invention provides a bisboron compound represented by the general formula (I):

[Formula 1]

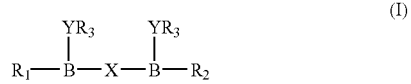

wherein B represents a boron atom,

Y represents an oxygen or sulfur atom, $R_1$ and $R_2$ independently represent a monocyclic aromatic group, a polycyclic aromatic group, or a heterocyclic group containing at least one heteroatom selected from oxygen, nitrogen and sulfur atoms, $R_3$ represents a hydrogen atom; —$(CH_2)_m$—$NR_4R_5$, wherein m represents an integer of 1 to 4, and $R_4$ and $R_5$ independently represent a hydrogen atom, or C1-C4 alkyl substituted or unsubstituted with amino, mono- or di-C1-C4 alkylamino or phenyl group, or $R_4$ and $R_5$ are taken together with the nitrogen atom to which they are bonded to form a 5- or 6-membered cyclic ring; —CO—$(CH_2)_m$—$NR_4R_5$, wherein m, $R_4$ and $R_5$ are as defined above; —COCH($NH_2$)$R_6$, wherein $R_6$ represents an amino acid residue or —$(CH_2)_n NH_2$, wherein n represents an integer of 1 to 3; —$CHR_7R_8$, wherein $R_7$ and $R_8$ independently represent C1-C4 alkyl substituted or unsubstituted with amino, mono- or di-(amino group-substituted or unsubstituted C1-C4 alkyl)amino or phenyl group, pyridyl, or phenyl substituted with C1-C3 alkoxy group; —$CH_2CH$($NH_2$)—$R_9$, wherein $R_9$ represents phenyl, or C1-C4 alkyl substituted with phenyl group; quinolyl or isoquinolyl substituted with C1-C4 alkyl group; or C1-C4 alkyl substituted with pyridyl, piperidino or pyrrolidinyl group, and X represents a monocyclic aromatic group, a polycyclic aromatic group or a heterocyclic group, which may be the same as or different from $R_1$ and $R_2$, or a bifunctional group having a monocyclic aromatic group, polycyclic aromatic group or heterocyclic group bonded to each side of a group selected from the group consisting of a single bond, O, $CH_2$, S, $SO_2$, $CH_2OCH_2$, $OCH_2$, $OCH_2CH_2OCH_2$, $OCH_2OCH_2CH_2$ and $CH_2OCH_2CH_2$, or a salt thereof, provided that bis[2-(hydroxyphenylboryl)benzyl]ether, 1,4-bis(4-(hydroxyphenylboryl)phenoxy)butane, bis[4-(hydroxyphenylboryl)benzyl]ether, bis[2-[(2-aminoethoxy)phenylboryl]benzyl]ether, bis[4-((2-aminoethoxy)phenylboryl)benzyl]ether, [4-[(2-aminoethoxy)phenylboryl]benzyl][2-[4-[(2-aminoethoxy)phenylboryl]phenyl]ethyl]ether, [2-[(2-aminoethoxy)phenylboryl]benzyl][2-[4-[(2-aminoethoxy)phenylboryl]phenyl]ethyl]ether and salts thereof are excluded.

In one embodiment of the present invention, the monocyclic aromatic group or polycyclic aromatic group is an aromatic group such as phenyl, diphenyl, terphenyl, naphthyl, binaphthyl, anthryl, phenanthryl, indenyl or fluorenyl, which is substituted or unsubstituted with at least one substituent selected from the group consisting of halogen, halogenated C1-C4 alkyl, cyano, hydroxy, sulfanyl, amino, nitro, mono- or di-C1-C4 alkylamino, carboxyl, C1-C4 alkylcarbonyl, C1-C4 alkylcarbonyloxy, C1-C4 alkyl, C2-C4 alkenyl, C2-C4 alkynyl, cycloalkyl, cycloalkenyl, C1-C4 alkylthio, C1-C4 alkoxy, amide and C1-C4 alkylamide.

In another embodiment, the heterocyclic group is a substituted or unsubstituted 5-15-membered heterocyclic group such as thiophenyl (another name: thienyl), furyl, pyridyl, dipyridyl, triazinyl, thiazolyl, pyrrolidinyl, oxazolyl, imidazolyl, pyrazolyl, indazolyl, quinolyl, indolyl, isoquinolyl, pyrimidyl, piperidinyl, piperidino, pyrazyl, morpholinyl or morpholino. The substituent, if any, is selected from the group consisting of halogen, cyano, hydroxy, sulfanyl, amino, nitro, mono- or di-C1-C4 alkylamino, carboxyl, C1-C4 alkylcarbonyl, C1-C4 alkylcarbonyloxy, C1-C4 alkyl, C2-C4 alkenyl, C2-C4 alkynyl, C1-C4 alkylthio, C1-C4 alkoxy, amide, C1-C4 alkylamide, aryl, cycloalkenyl and cycloalkyl, for example.

In another embodiment, the X is a group selected from the group consisting of the following groups.

[Formula 2]

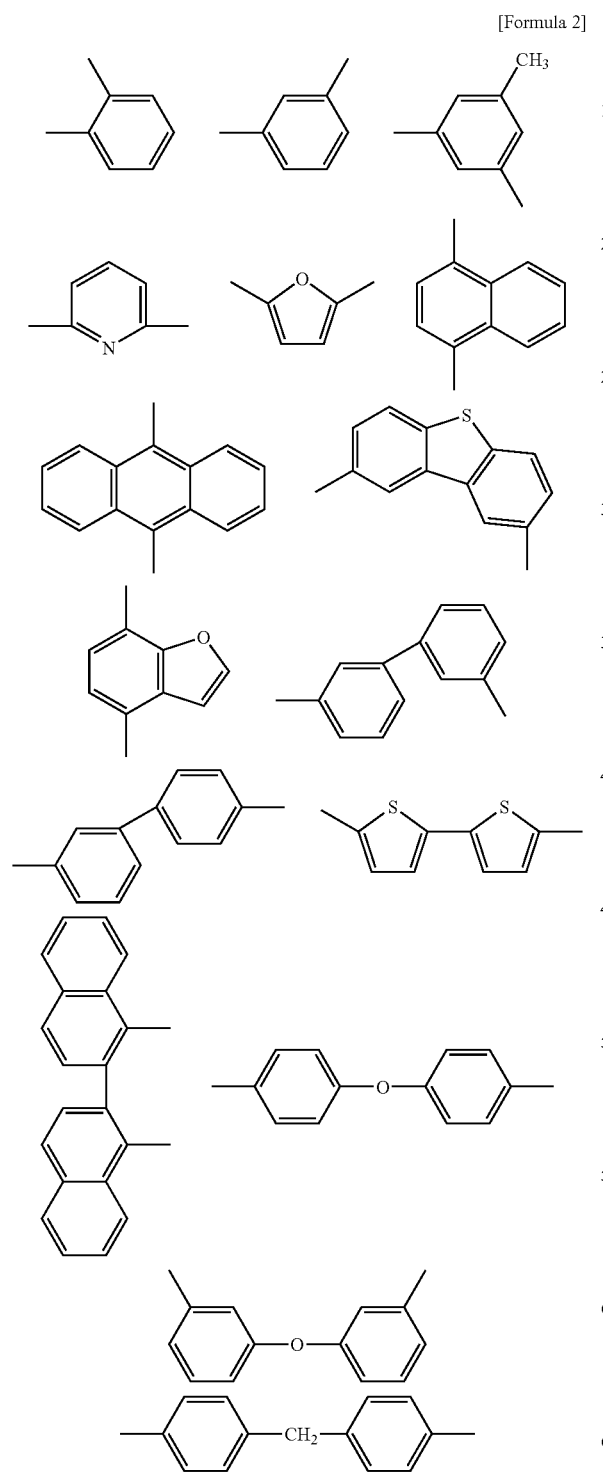

In another embodiment, the X is substituted or unsubstituted diphenyl ether, dibenzyl ether, phenyl benzyl ether, benzyl phenethyl ether, phenoxyethyl benzyl ether or diphenyl, having a meta-meta, ortho-ortho, para-para, meta-para, meta-ortho or ortho-para orientation.

In another embodiment, the X is diphenyl ether having any of meta-meta, ortho-ortho, para-para, ortho-para, ortho-meta and meta-para orientations.

In another embodiment, the X is diphenyl ether having a meta-meta, ortho-ortho or para-para orientation.

In another embodiment, the X is dibenzyl ether having any of meta-meta, ortho-para, ortho-meta and meta-para orientations.

In another embodiment, the X is dibenzyl ether having a meta-meta orientation.

In another embodiment, the X is benzyl phenethyl ether having any of meta-meta, ortho-ortho, ortho-meta and meta-para orientations.

In another embodiment, the X is benzyl phenethyl ether having a meta-meta or ortho-ortho orientation.

In another embodiment, the $R_1$ and $R_2$ are independently a substituted or unsubstituted phenyl or phenylene group.

In another embodiment, the $R_3$ is a hydrogen atom or a 2-aminoethyl group.

In another embodiment, the Y is an oxygen atom.

In another embodiment, the compound is a compound selected from the group consisting of:
bis(4,4'-(phenylhydroxyboryl)phenyl) ether;
bis(4,4'-(phenylaminoethoxyboryl)phenyl) ether;
bis(4,4'-(3-chloro-4-methylphenylhydroxyboryl)benzyl) ether;
bis(3,3'-(phenylhydroxyboryl)benzyl) ether;
bis(3,3'-(phenylaminoethoxyboryl)benzyl) ether;
bis(4-(4-trifluoromethylphenylhydroxyboryl)benzyl) ether;
bis(4-(1-naphthylhydroxyboryl)benzyl) ether;
bis(4-(fluorophenylhydroxyboryl)benzyl) ether;
bis(3-(4-methoxyphenylhydroxyboryl)benzyl) ether;
(3-(phenylhydroxyboryl)benzyl) (4-(phenylhydroxyboryl)benzyl) ether;

(2-(phenylhydroxyboryl)benzyl) (3-(phenylhydroxyboryl)benzyl) ether;
(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
bis(3-(3-chloro-4-methylphenylhydroxyboryl)benzyl) ether;
(2-(phenylaminoethoxyboryl)benzyl) (3-(phenylaminoethoxyboryl)benzyl) ether;
2-(phenylaminoethoxyboryl)benzyl) (4-(phenylaminoethoxyboryl)benzyl) ether;
bis(3-(4-fluorophenylhydroxyboryl)benzyl) ether;
bis(3-(4-fluorophenylaminoethoxyboryl)benzyl) ether;
bis(4-(4-chloro-3-methyl-phenylhydroxyboryl)benzyl) ether;
bis(4-(4-chloro-3-methyl-phenylaminoethoxyboryl)benzyl) ether;
bis(3-(3',4'-methylenedioxy-phenylhydroxyboryl)benzyl) ether;
(3-(3-chloro-4-methylphenylhydroxyboryl)benzyl) (4-(3-chloro-4-methylphenylhydroxyboryl)benzyl) ether;
(3-(3',4',5'-trifluorophenylhydroxyboryl)benzyl) (4-(3',4',5'-trifluorophenylhydroxyboryl)benzyl) ether;
bis(3-(4-methoxyphenylaminoethoxyboryl)benzyl) ether;
(3-(4-chloro-3-methylphenylhydroxyboryl)benzyl) (2-(4-chloro-3-methylphenylhydroxyboryl)benzyl) ether;
bis(3-(4-cyanophenylhydroxyboryl)benzyl) ether;
bis(3-(2'-thiophenylhydroxyboryl)benzyl) ether;
bis(3-(1'-naphthylhydroxyboryl)benzyl) ether;
bis(3-(2'-thiophenylhydroxyboryl)benzyl) ether;
bis(4-(2-methoxy-5-fluorophenylhydroxyboryl)benzyl) ether;
bis(4-(2-methoxy-5-fluorophenylaminoethoxyboryl)benzyl) ether;
(3-(4-chloro-3-methyl-phenylaminoethoxyboryl)benzyl) (2-(4-chloro-3-methyl-phenylaminoethoxyboryl)benzyl) ether;
bis(4-(3,4-difluorophenylhydroxyboryl)benzyl) ether;
bis(4-(3,4-difluorophenylaminoethoxyboryl)benzyl) ether;
(3-(3',4',5'-trifluorophenylaminoethoxyboryl)benzyl) (4-(3',4',5'-trifluorophenylaminoethoxyboryl)benzyl) ether;
5,5'-(phenylhydroxyboryl)-2,2'-dithiophene;
5,5'-(phenylaminoethoxyboryl)-2,2'-dithiophene;
3,5-di(phenylaminoethoxyboryl)toluene;
2,5-di(phenylhydroxyboryl)toluene;
2,2'-di(phenylhydroxyboryl)-1,1'-binaphthyl;
2,2'-di(phenylaminoethoxyboryl)-1,1'-binaphthyl;
bis(4-(4-methylphenylhydroxyboryl)benzyl) ether;
bis(4-(4-methylphenylaminoethoxyboryl)benzyl) ether;
4,4'-(4-methylphenylaminoethoxyboryl)diphenyl;
4,4'-(4-methylphenylhydroxyboryl)diphenyl ether;
4,4'-(4-methylphenylaminoethoxyboryl)diphenyl ether;
4,4'-bis(3-chloro-4-methyl-phenylaminoethoxyboryl)phenyl ether;
(2-(phenylhydroxyboryl)phenethyl) ((2-phenylhydroxyboryl)benzyl) ether;
(2-(phenylhydroxyboryl)phenethyl) ((2-phenylaminoethoxyboryl)benzyl) ether;
(4-phenylhydroxyborylphenyl) (4'-phenylhydroxyborylbenzyl) ether;
(4-phenylaminoethoxyborylphenyl) (4'-phenylaminoethoxyborylbenzyl) ether;
(4-(2-thiopheneaminoethoxyboryl)phenoxyethyl) (4'-(2-thiopheneaminoethoxyboryl)benzyl) ether;
(4-trifluoromethylphenylhydroxyborylphenyl) (4'-trifluoromethylphenylhydroxyborylbenzyl) ether;
(4-trifluoromethylphenylaminoethoxyborylphenyl) (4'-trifluoromethylphenylaminoethoxyborylbenzyl) ether;
9,10-bis-(trifluoromethylphenylhydroxyboryl)anthracene;
9,10-bis-(trifluoromethylphenylaminoethoxyboryl)anthracene;
bis(3-(1-naphthylaminoethoxyboryl)benzyl) ether;
4,5-di(phenylhydroxyboryl)-2,7-di-t-butyl-9,9-dimethylxanthrene;
4,5-di(phenylaminoethoxyboryl)-2,7-di-t-butyl-9,9-dimethylxanthrene;
(4-(phenylhydroxyboryl)phenoxyethyl) (4-(phenylhydroxyboryl)benzyl) ether;
(4-(phenylaminoethoxyboryl)phenoxyethyl) (4-(phenylaminoethoxyboryl)benzyl) ether;
6,6'-(phenylhydroxyboryl)-2,2'-dipyridyl;
6,6'-(phenylaminoethoxyboryl)-2,2'-dipyridyl;
bis(2,5-(phenylhydroxyboryl)furan;
bis(2,5-(phenylaminoethoxyboryl)furan;
bis(4,4'-(phenyl-N,N-dimethylaminoethoxyboryl)phenyl) ether;
bis(4,4'-(phenyl-N-methylaminoethoxyboryl)phenyl) ether;
bis(4,4'-(phenyl-glycineboryl)phenyl) ether;
bis(4,4'-(phenyl-glutamineboryl)phenyl) ether;
bis(4,4'-(phenyl-cysteineboryl)phenyl) ether;
bis(4,4'-(phenyl-asparagineboryl)phenyl) ether;
(4-(phenyl-N-methylaminoethylboryl)phenyl) (4'-(hydroxymethylphenyl-N-methylaminoethylboryl)phenyl) ether;
(4-(phenyl-N,N-dimethylaminoethylboryl)phenyl) (4'-(hydroxymethylphenyl-N,N-dimethylaminoethylboryl)phenyl) ether;
(4-(phenyl-glutamic acid boryl)phenyl) (4'-(hydroxymethylphenyl-glutamic acid boryl)phenyl) ether;
(4-(phenyl-glutamineboryl)phenyl) (4'-(hydroxymethylphenyl-glutamineboryl)phenyl) ether;
bis(4,4'-(phenyl-N,N-dimethylaminoethoxyboryl)benzyl) ether;
bis(4,4'-(phenyl-N-aminoethyl-aminoethoxyboryl)phenyl) ether;
(4-(phenyl-cysteineboryl)phenyl) (4'-(hydroxymethylphenyl-cysteineboryl)phenyl) ether;
bis(4,4'-(phenoxyphenyl-aminoethoxyboryl)phenyl) ether;
bis(4,4'-(phenyl-N-aminoethyl-aminoethoxyboryl)benzyl) ether;
bis(4,4'-(phenyl-N-methylaminoethoxyboryl)benzyl) ether;
(4'-trifluoromethylphenyl-N,N-dimethylaminoethoxyboryl)-4-phenyl (4'-trifluoromethylphenyl-N,N-dimethylaminoethoxyboryl)benzyl ether;
(4'-trifluoromethylphenyl-N-methylaminoethoxyboryl)-4-phenyl (4'-trifluoromethylphenyl-N-methylaminoethoxyboryl)-4-benzyl ether;
bis(3,3'-(phenyl-N,N-dimethylaminoethoxyboryl)benzyl) ether;
bis(3,3'-(phenyl-asparagineboryl)benzyl) ether;
bis(3,3'-(phenyl-aminothioethoxyboryl)benzyl) ether;
bis(4,4'-(phenyl-2-pyridylmethoxyboryl)benzyl) ether;
bis(4,4'-(p-trifluoromethylphenyl-hydroxyboryl)benzyl) ether;
bis(4,4'-(3-chloro-4-methylphenyl-hydroxyboryl)benzyl) ether;
bis(4,4'-(phenyl-lysineboryl)benzyl) ether;
bis(4,4'-(p-methoxymethyl-phenyl-hydroxyboryl)benzyl) ether;
bis(4,4'-(3,4-difluorophenyl-hydroxyboryl)benzyl) ether;
bis(4,4'-(p-methoxyphenyl-aminoethoxyboryl)benzyl) ether;

bis(4,4'-(p-methoxyphenyl-N-methylaminoethoxyboryl)benzyl) ether;
bis(4,4'-(p-methoxyphenyl-N,N-dimethylaminoethoxyboryl)benzyl) ether;
bis(4,4'-(p-methoxyphenyl-2,4-diaminobutyric acid boryl)benzyl) ether;
bis(4,4'-(3,4-difluorophenyl-aminoethoxyboryl)benzyl) ether;
bis(4,4'-(3,4-difluorophenyl-N-methylaminoethoxyboryl)benzyl) ether;
bis(4,4'-(3,4-difluorophenyl-N,N-dimethylaminoethoxyboryl)benzyl) ether;
bis(4,4'-(3,4-difluorophenyl-N-aminoethylaminoethoxyboryl)benzyl) ether;
bis(4,4'-(3-chloro-4-methylphenyl-aminoethoxyboryl)benzyl) ether;
bis(4,4'-(3-chloro-4-methylphenyl-N-methylaminoethoxyboryl)benzyl) ether;
bis(4,4'-(3-chloro-4-methylphenyl-N,N-dimethylaminoethoxyboryl)benzyl) ether;
bis(4,4'-(3-chloro-4-methylphenyl-2-piperidylmethyloxyboryl)benzyl) ether;
bis(4,4'-(p-trifluoromethylphenyl-N,N-dimethylaminoethoxyboryl)benzyl) ether;
bis(4,4'-(p-trifluoromethylphenyl-asparagineboryl)benzyl) ether;
bis(4,4'-(p-trifluoromethylphenyl-aminoethoxyboryl)benzyl) ether;
(4-phenyl-N-methylaminoethoxyborylphenyl) 4'-(N-methylaminoethoxyborylbenzyl) ether;
(4-phenyl-N,N-dimethylaminoethoxyborylphenyl) 4'-(N,N-dimethylaminoethoxyborylbenzyl) ether;
(4-phenyl-2-pyridylmethoxyborylphenyl) (4'-phenyl-2-pyridylmethoxyborylbenzyl) ether;
4-(phenyl-p-methoxyphenyl-2-pyridylmethoxyboryl)-phenyl 4'(p-methoxyphenyl-2-pyridylmethoxyboryl)benzyl ether;
bis(4,4'-(phenyl-3-piperidyloxyboryl)phenyl) ether;
bis(4,4'-(phenyl-2-pyridylmethoxyboryl)phenyl) ether;
bis(4,4'-(phenyl-aminothioethoxyboryl)phenyl) ether;
bis(4,4'-(phenyl-2-amino-1-phenylethoxyboryl)phenyl) ether;
bis(4,4'-(phenyl-ornithineboryl)phenyl) ether;
bis(4,4'-(phenyl-2,3-diaminopropionic acid boryl)phenyl) ether;
bis(4,4'-(phenyl-lysineboryl)phenyl) ether;
bis(4,4'-(phenyl-2-pyrrolidinemethoxyboryl)phenyl) ether;
bis(4,4'-(naphthylhydroxyboryl)phenyl) ether;
bis(4,4'-(tolylhydroxyboryl)phenyl) ether;
bis(4,4'-(naphthyl-aminoethoxyboryl)phenyl) ether;
bis(4,4'-(naphthyldimethylaminoethoxyboryl)phenyl) ether;
bis(4,4'-(naphthyl-2-pyridylmethoxyboryl)phenyl) ether;
bis(4,4'-(naphthylglutamineboryl)phenyl) ether;
bis(4,4'-(naphthyl-2,4-diaminopropionic acid boryl)phenyl) ether;
bis(4,4'-(tolyldimethylaminoethoxyboryl)phenyl) ether;
bis(4,4'-(tolylpiperazylethoxyboryl)phenyl) ether;
bis(4,4'-(tolylglutamineboryl)phenyl) ether;
bis(4,4'-(tolyllysineboryl)phenyl) ether;
bis(4,4'-(phenyl-2-amino-1-phenylethoxyboryl)benzyl) ether;
bis(4,4'-(phenyl-aminothioethoxyboryl)benzyl) ether;
bis(4,4'-(phenyl-2-pyrrolidinemethoxyboryl)benzyl) ether;
bis(4,4'-(phenyl-2,4-diaminobutyric acid boryl)benzyl) ether;
bis(4,4'-(phenyl-butylaminoethoxyboryl)benzyl) ether;
bis(4,4'-(phenyl-phenylaminoethoxyboryl)benzyl) ether;
bis(4,4'-(phenyl-benzylaminoethoxyboryl)benzyl) ether;
bis(4,4'-(phenyl-N-methylpiperidine-methoxyboryl)benzyl) ether;
bis(4,4'-(phenyl-1-methyl-2-aminoethoxyboryl)benzyl) ether;
bis(4,4'-(phenyl-1-piperidylethoxyboryl)benzyl) ether;
bis(3,3'-(phenyl-2-pyrrolidinomethoxyboryl)benzyl) ether;
bis(3,3'-(phenyl-aminothioethoxyboryl)benzyl) ether;
bis(3,3'-(phenyl-2-phenyl-2-aminoethoxyboryl)benzyl) ether;
bis(3,3'-(phenyl-2-piperazylmethoxyboryl)benzyl) ether;
bis(3,3'-(phenyl-dimethylaminoethoxyboryl)benzyl) ether;
bis(3,3'-(phenyl-1-methyl-2-aminoethoxyboryl)benzyl) ether;
bis(3,3'-(phenyl-2-piperidylethoxyboryl)benzyl) ether;
bis(3,3'-(phenyl-2-pyridylmethoxyboryl)benzyl) ether;
bis(3,3'-(phenyl-2-amino-1-phenylethoxyboryl)benzyl) ether;
bis(3,3'-(phenyl-N-methylethoxyboryl)benzyl) ether;
bis(3,3'-(phenyl-N-aminoethyl-1-methyl-3-aminopropoxyboryl)benzyl) ether;
bis(3,3'-(phenyl-glutamineboryl)benzyl) ether;
bis(3,3'-(phenyl-2,4-diaminobutyric acid boryl)benzyl) ether;
bis(3,3'-(phenyl-N-butylaminoethylboryl)benzyl) ether;
bis(3,3'-(phenyl-asparagineboryl)benzyl) ether;
bis(3,3'-(phenyl-lysineboryl)benzyl) ether;
bis(3,3'-(phenyl-ornithineboryl)benzyl) ether;
bis(4,4'-(phenyl-2-methyl-8-quinolinooxyboryl)phenyl) ether;
bis(4,4'-(phenyl-2-pyridylmethoxyboryl)phenyl) ether;
bis(4,4'-(phenyl-2-benzyl-2-amino-ethoxyboryl)benzyl) ether;
bis(4,4'-(phenyl-2-benzyl-2-amino-ethoxyboryl)phenyl) ether;
bis(3,3'-(phenyl-2-benzyl-2-amino-ethoxyboryl)phenyl) ether;
bis(4,4'-(phenyl-2-phenyl-2-amino-ethoxyboryl)benzyl) ether;
and salts thereof.

In a second aspect, the present invention provides a composition for controlling the intracellular calcium concentration, characterized in that the composition comprises the bisboron compound represented by the general formula (I) or a salt thereof as an active ingredient.

The bisboron compound includes all bisboron compounds within the scope of the present invention as defined and described above.

In another embodiment, the composition of the present invention may be used for prevention, alleviation or treatment of a disease caused by an increase in the intracellular calcium concentration.

The phrase "controlling the intracellular calcium concentration" refers to inhibition of release of endogenous calcium and/or entry of capacitative calcium, preferably inhibition of entry of capacitative calcium.

In another embodiment, the disease is ischemic heart or brain disease, cardiac hypertrophy, renal disease (such as glomerulosclerosis), hypertension, cerebral vasospasm, pancreatitis, (bronchial) asthma, immunodeficiency, allergic disease or Alzheimer's disease.

The bisboron compound of the present invention significantly inhibits an increase in the intracellular calcium concentration. Most of the compounds of the present invention exhibit intracellular calcium concentration control activity at a capacitative calcium entry (CCE) $IC_{50}$ of less than 3 μM, and some of them exhibit such activity at an extremely low CCE $IC_{50}$ concentration of 50 nM to 1 µM. Thus, the compound of the present invention may be an intracellular calcium concentration control agent superior to a monoboron compound (5 µM or more), advantageously.

BEST MODE FOR CARRYING OUT THE INVENTION

The bisboron compound of the present invention is represented by the general formula (I),
wherein B represents a boron atom,
Y represents an oxygen or sulfur atom,
$R_1$ and $R_2$ independently represent a monocyclic aromatic group, a polycyclic aromatic group, or a heterocyclic group containing at least one heteroatom selected from oxygen, nitrogen and sulfur atoms,
$R_3$ represents a hydrogen atom; —$(CH_2)_m$—$NR_4R_5$, wherein m represents an integer of 1 to 4, and $R_4$ and $R_5$ independently represent a hydrogen atom, or C1-C4 alkyl substituted or unsubstituted with amino, mono- or di-C1-C4 alkylamino or phenyl group, or $R_4$ and $R_5$ are taken together with the nitrogen atom to which they are bonded to form a 5- or 6-membered cyclic ring; —CO—$(CH_2)_m$—$NR_4R_5$, wherein m, $R_4$ and $R_5$ are as defined above; —COCH($NH_2$)$R_6$, wherein $R_6$ represents an amino acid residue or —$(CH_2)_n NH_2$, wherein n represents an integer of 1 to 3; —$CHR_7R_8$, wherein $R_7$ and $R_8$ independently represent C1-C4 alkyl substituted or unsubstituted with amino, mono- or di-(amino group-substituted or unsubstituted C1-C4 alkyl)amino or phenyl group, pyridyl, or phenyl substituted with C1-C3 alkoxy group; —$CH_2CH(NH_2)$—$R_9$, wherein $R_9$ represents phenyl, or C1-C4 alkyl substituted with phenyl group; quinolyl or isoquinolyl substituted with C1-C4 alkyl group; or C1-C4 alkyl substituted with pyridyl, piperidino or pyrrolidinyl group, and
X represents a monocyclic aromatic group, a polycyclic aromatic group or a heterocyclic group, which may be the same as or different from $R_1$ and $R_2$, or a bifunctional group having a monocyclic aromatic group, polycyclic aromatic group or heterocyclic group bonded to each side of a group selected from the group consisting of a single bond, O, $CH_2$, S, $SO_2$, $CH_2OCH_2$, $OCH_2$, $OCH_2CH_2OCH_2$, $OCH_2OCH_2CH_2$ and $CH_2OCH_2CH_2$.

However, the bisboron compound of the present invention does not include the following compounds disclosed in International Publication WO 03/033002 by the present inventors:
bis[2-(hydroxyphenylboryl)benzyl]ether;
1,4-bis(4-(hydroxyphenylboryl)phenoxy)butane;
bis[4-(hydroxyphenylboryl)benzyl]ether;
bis[2-[(2-aminoethoxy)phenylboryl]benzyl]ether;
bis[4-((2-aminoethoxy)phenylboryl)benzyl]ether;
[4-[(2-aminoethoxy)phenylboryl]benzyl][2-[4-[(2-aminoethoxy)phenylboryl]phenyl]ethyl]ether;
[2-[(2-aminoethoxy)phenylboryl]benzyl][2-[4-[(2-aminoethoxy)phenylboryl]phenyl]ethyl]ether;
and salts thereof.

The present inventors have synthesized many bisboron compounds not specifically disclosed in International Publication WO 03/033002 and having activity unknown and measured their capacitative calcium entry (CCE) inhibitory activity. As a result, the inventors have found that many of the newly synthesized bisboron compounds have a CCE $IC_{50}$ at a physiological level in the µM order and have a CCE $IC_{50}$ of preferably less than 3 µM, more preferably 1 µM or less, still more preferably 0.5 µM or less, and most preferably 0.2 µM or less. Here, the CCE $IC_{50}$ refers to a concentration of an inhibitory drug inhibiting 50% of capacitative calcium entry.

The compound of the present invention also has activity to inhibit calcium release by $IP_3$ from endoplasmic reticulum through an $IP_3$ receptor. In the present specification, such calcium release is called endogenous calcium release. This activity is based on inhibition of $IP_3$ receptor activity by the compound of the present invention.

The "intracellular calcium concentration control" used in the present specification refers to inhibition of an abnormal increase in the intracellular calcium concentration. Specifically, the intracellular calcium concentration control refers to inhibition of calcium release from endoplasmic reticulum through an $IP_3$ receptor and inhibition of extracellular calcium entry accompanied by the calcium release, which are specific and physiological inhibitions. In the present invention, such inhibitory activity is called intracellular calcium concentration control activity.

The "monocyclic aromatic group" used in the present specification refers to a substituted or unsubstituted phenyl or phenylene group. The phenylene group includes o-, m- and p-phenylene. An example of the substituent is at least one substituent selected from the group consisting of halogen, halogenated C1-C4 alkyl, cyano, hydroxy, hydroxy C1-C4 alkyl, sulfanyl, amino, nitro, mono- or di-C1-C4 alkylamino, carboxyl, C1-C4 alkylcarbonyl, C1-C4 alkylcarbonyloxy, C1-C4 alkyl, C2-C4 alkenyl, C2-C4 alkynyl, cycloalkyl, cycloalkenyl, C1-C4 alkylthio, C1-C4 alkoxy, aryl, aryloxy, amide and C1-C4 alkylamide. Specific examples of the substituted phenyl include, but are not limited to, mono-, di- or trifluorophenyl, methoxyphenyl, tolyl, xylyl, o-chlorotolyl, trifluoromethylphenyl, 2-methoxy-5-fluorophenyl, hydroxymethylphenyl and phenoxyphenyl. Examples of the substituted phenylene include, but are not limited to, 5-methyl-m-phenylene and 5-methyl-p-phenylene.

The "polycyclic aromatic group" used in the present specification refers to a fused polycyclic hydrocarbon group formed by a fused ring of 2 to 6, preferably 2 to 3, 5-membered and/or 6-membered monocyclic carbon rings. Examples of the group include, but are not limited to, substituted or unsubstituted naphthyl, anthryl, phenanthryl, indenyl and fluorenyl. Here, examples of the substituent include the same substituents as listed above.

The heterocyclic ring used in the present specification refers to a cyclic compound containing in the ring at least one heteroatom selected from a nitrogen atom, an oxygen atom and a sulfur atom. The heterocyclic group is preferably a substituted or unsubstituted 5- to 15-membered heterocyclic group. Examples of the group include, but are not limited to, thiophenyl, furyl, pyridyl, dipyridyl, triazinyl, thiazolyl, pyrrolidinyl, oxazolyl, imidazolyl, pyrazolyl, indazolyl, quinolyl, indolyl, isoquinolyl, pyrimidyl, piperidinyl, piperidino, pyrazyl, morpholinyl, morpholino and xanthrene. Here, examples of the substituent include the same substituents as listed above.

The "C1-C4 alkyl" or "C1-C3 alkyl" used in the present specification refers to methyl, ethyl, propyl, butyl and their isomers.

The "C1-C4 alkoxy" used in the present specification refers to methoxy, ethoxy, propoxy, butoxy and their isomers.

The "C1-C4 alkylthio" used in the present specification refers to methylthio, ethylthio, propylthio, butylthio and their isomers.

The "isomer" used in the present specification includes both a structural isomer and an optical isomer.

The "halogen atom" used in the present specification refers to fluorine, chlorine, bromine and iodine.

The "aryl" used in the present specification refers to a remaining atomic group obtained by excluding one hydrogen atom from an aromatic hydrocarbon. Examples of the aryl include substituted or unsubstituted phenyl, naphthyl and anthryl. Here, examples of the substituent include the same substituents as listed above.

The "cycloalkyl" used in the present specification refers to a cyclic saturated hydrocarbon. Examples of the cycloalkyl include 3- to 10-membered, preferably 5- to 6-membered, cycloalkyl such as cyclopentyl and cyclohexyl.

The "cycloalkenyl" used in the present specification refers to a cyclic unsaturated hydrocarbon having one or two carbon-carbon double bonds. Preferable examples of the cycloalkenyl include 5- or 6-membered cycloalkenyl such as cyclopentenyl and cyclohexenyl.

The "C2-C4 alkenyl" used in the present specification refers to ethenyl, propenyl, butenyl and their isomers.

The "C2-C4 alkynyl" used in the present specification refers to ethynyl, propynyl, butynyl and their isomers.

The "amino acid residue" used in the present specification refers to a side group other than a carboxyl group and an amino group bonded to the α-carbon atom of an amino acid. The amino acid refers to any L-, D- or DL-amino acid and includes lysine, arginine, asparagine, aspartic acid, glutamine, glutamic acid, serine, threonine, glycine, alanine, valine, leucine, isoleucine, tyrosine, phenylalanine, tryptophan, cysteine, methionine, histidine and proline.

Unless otherwise specified, the number of substituted groups described in the present specification is 1 or more, and preferably 1, 2 or 3.

Examples of the suitable compounds in the present invention are listed as follows:
bis(4,4'-(phenylhydroxyboryl)phenyl) ether;
bis(4,4'-(phenylaminoethoxyboryl)phenyl) ether;
bis(4,4'-(3-chloro-4-methylphenylhydroxyboryl)benzyl) ether;
bis(3,3'-(phenylhydroxyboryl)benzyl) ether;
bis(3,3'-(phenylaminoethoxyboryl)benzyl) ether;
bis(4-(4-trifluoromethylphenylhydroxyboryl)benzyl) ether;
bis(4-(1-naphthylhydroxyboryl)benzyl) ether;
bis(4-(fluorophenylhydroxyboryl)benzyl) ether;
bis(3-(4-methoxyphenylhydroxyboryl)benzyl) ether;
(3-(phenylhydroxyboryl)benzyl) (4-(phenylhydroxyboryl)benzyl) ether;
(2-(phenylhydroxyboryl)benzyl) (3-(phenylhydroxyboryl)benzyl) ether;
(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
bis(3-(3-chloro-4-methylphenylhydroxyboryl)benzyl) ether;
(2-(phenylaminoethoxyboryl)benzyl) (3-(phenylaminoethoxyboryl)benzyl) ether;
2-(phenylaminoethoxyboryl)benzyl) (4-(phenylaminoethoxyboryl)benzyl) ether;
bis(3-(4-fluorophenylhydroxyboryl)benzyl) ether;
bis(3-(4-fluorophenylaminoethoxyboryl)benzyl) ether;
bis(4-(4-chloro-3-methyl-phenylhydroxyboryl)benzyl) ether;
bis(4-(4-chloro-3-methyl-phenylaminoethoxyboryl)benzyl) ether;
bis(3-(3',4'-methylenedioxy-phenylhydroxyboryl)benzyl) ether;
(3-(3-chloro-4-methylphenylhydroxyboryl)benzyl) (4-(3-chloro-4-methylphenylhydroxyboryl)benzyl) ether;
(3-(3',4',5'-trifluorophenylhydroxyboryl)benzyl) (4-(3',4',5'-trifluorophenylhydroxyboryl)benzyl) ether;
bis(3-(4-methoxyphenylaminoethoxyboryl)benzyl) ether;
(3-(4-chloro-3-methylphenylhydroxyboryl)benzyl) (2-(4-chloro-3-methylphenylhydroxyboryl)benzyl) ether;
bis(3-(4-cyanophenylhydroxyboryl)benzyl) ether;
bis(3-(2'-thiophenylhydroxyboryl)benzyl) ether;
bis(3-(1'-naphthylhydroxyboryl)benzyl) ether;
bis(3-(2'-thiophenylhydroxyboryl)benzyl) ether;
bis(4-(2-methoxy-5-fluorophenylhydroxyboryl)benzyl) ether;
bis(4-(2-methoxy-5-fluorophenylaminoethoxyboryl)benzyl) ether;
(3-(4-chloro-3-methyl-phenylaminoethoxyboryl)benzyl) (2-(4-chloro-3-methyl-phenylaminoethoxyboryl)benzyl) ether;
bis(4-(3,4-difluorophenylhydroxyboryl)benzyl) ether;
bis(4-(3,4-difluorophenylaminoethoxyboryl)benzyl) ether;
(3-(3',4',5'-trifluorophenylaminoethoxyboryl)benzyl) (4-(3',4',5'-trifluorophenylaminoethoxyboryl)benzyl) ether;
5,5'-(phenylhydroxyboryl)-2,2'-dithiophene;
5,5'-(phenylaminoethoxyboryl)-2,2'-dithiophene;
3,5-di(phenylaminoethoxyboryl)toluene;
2,5-di(phenylhydroxyboryl)toluene;
2,2'-di(phenylhydroxyboryl)-1,1'-binaphthyl;
2,2'-di(phenylaminoethoxyboryl)-1,1'-binaphthyl;
bis(4-(4-methylphenylhydroxyboryl)benzyl) ether;
bis(4-(4-methylphenylaminoethoxyboryl)benzyl) ether;
4,4'-(4-methylphenylaminoethoxyboryl)diphenyl;
4,4'-(4-methylphenylhydroxyboryl)diphenyl ether;
4,4'-(4-methylphenylaminoethoxyboryl)diphenyl ether;
4,4'-bis(3-chloro-4-methyl-phenylaminoethoxyboryl)phenyl ether;
(2-(phenylhydroxyboryl)phenethyl) ((2-phenylhydroxyboryl)benzyl) ether;
(2-(phenylhydroxyboryl)phenethyl) ((2-phenylaminoethoxyboryl)benzyl) ether;
(4-phenylhydroxyborylphenyl) (4'-phenylhydroxyborylbenzyl) ether;
(4-phenylaminoethoxyborylphenyl) (4'-phenylaminoethoxyborylbenzyl) ether;
(4-(2-thiopheneaminoethoxyboryl)phenoxyethyl) (4'-(2-thiopheneaminoethoxyboryl)benzyl) ether;
(4-trifluoromethylphenylhydroxyborylphenyl) (4'-trifluoromethylphenylhydroxyborylbenzyl) ether;
(4-trifluoromethylphenylaminoethoxyborylphenyl) (4'-trifluoromethylphenylaminoethoxyborylbenzyl) ether;
9,10-bis-(trifluoromethylphenylhydroxyboryl)anthracene;
9,10-bis-(trifluoromethylphenylaminoethoxyboryl)anthracene;
bis(3-(1-naphthylaminoethoxyboryl)benzyl) ether;
4,5-di(phenylhydroxyboryl)-2,7-di-t-butyl-9,9-dimethylxanthrene;
4,5-di(phenylaminoethoxyboryl)-2,7-di-t-butyl-9,9-dimethylxanthrene;
(4-(phenylhydroxyboryl)phenoxyethyl) (4-(phenylhydroxyboryl)benzyl) ether;
(4-(phenylaminoethoxyboryl)phenoxyethyl) (4-(phenylaminoethoxyboryl)benzyl) ether;
6,6'-(phenylhydroxyboryl)-2,2'-dipyridyl;
6,6'-(phenylaminoethoxyboryl)-2,2'-dipyridyl;
bis(2,5-(phenylhydroxyboryl)furan;
bis(2,5-(phenylaminoethoxyboryl)furan;
bis(4,4'-(phenyl-N,N-dimethylaminoethoxyboryl)phenyl) ether;
bis(4,4'-(phenyl-N-methylaminoethoxyboryl)phenyl) ether;
bis(4,4'-(phenyl-glycineboryl)phenyl) ether;
bis(4,4'-(phenyl-glutamineboryl)phenyl) ether;
bis(4,4'-(phenyl-cysteineboryl)phenyl) ether;
bis(4,4'-(phenyl-asparagineboryl)phenyl) ether;

(4-(phenyl-N-methylaminoethylboryl)phenyl) (4'-(hydroxymethylphenyl-N-methylaminoethylboryl)phenyl) ether;
(4-(phenyl-N,N-dimethylaminoethylboryl)phenyl) (4'-(hydroxymethylphenyl-N,N-dimethylaminoethylboryl)phenyl) ether;
(4-(phenyl-glutamic acid boryl)phenyl) (4'-(hydroxymethylphenyl-glutamic acid boryl)phenyl) ether;
(4-(phenyl-glutamineboryl)phenyl) (4'-(hydroxymethylphenyl-glutamineboryl)phenyl) ether;
bis(4,4'-(phenyl-N,N-dimethylaminoethoxyboryl)benzyl) ether;
bis(4,4'-(phenyl-N-aminoethyl-aminoethoxyboryl)phenyl) ether;
(4-(phenyl-cysteineboryl)phenyl) (4'-(hydroxymethylphenyl-cysteineboryl)phenyl) ether;
bis(4,4'-(phenoxyphenyl-aminoethoxyboryl)phenyl) ether;
bis(4,4'-(phenyl-N-aminoethyl-aminoethoxyboryl)benzyl) ether;
bis(4,4'-(phenyl-N-methylaminoethoxyboryl)benzyl) ether;
(4'-trifluoromethylphenyl-N,N-dimethylaminoethoxyboryl)-4-phenyl (4'-trifluoromethylphenyl-N,N-dimethylaminoethoxyboryl)benzyl ether;
(4'-trifluoromethylphenyl-N-methylaminoethoxyboryl)-4-phenyl (4'-trifluoromethylphenyl-N-methylaminoethoxyboryl)-4-benzyl ether;
bis(3,3'-(phenyl-N,N-dimethylaminoethoxyboryl)benzyl) ether;
bis(3,3'-(phenyl-asparagineboryl)benzyl) ether;
bis(3,3'-(phenyl-aminothioethoxyboryl)benzyl) ether;
bis(4,4'-(phenyl-2-pyridylmethoxyboryl)benzyl) ether;
bis(4,4'-(p-trifluoromethylphenyl-hydroxyboryl)benzyl) ether;
bis(4,4'-(3-chloro-4-methylphenyl-hydroxyboryl)benzyl) ether;
bis(4,4'-(phenyl-lysineboryl)benzyl) ether;
bis(4,4'-(p-methoxymethyl-phenyl-hydroxyboryl)benzyl) ether;
bis(4,4'-(3,4-difluorophenyl-hydroxyboryl)benzyl) ether;
bis(4,4'-(p-methoxyphenyl-aminoethoxyboryl)benzyl) ether;
bis(4,4'-(p-methoxyphenyl-N-methylaminoethoxyboryl)benzyl) ether;
bis(4,4'-(p-methoxyphenyl-N,N-dimethylaminoethoxyboryl)benzyl) ether;
bis(4,4'-(p-methoxyphenyl-2,4-diaminobutyric acid boryl)benzyl) ether;
bis(4,4'-(3,4-difluorophenyl-aminoethoxyboryl)benzyl) ether;
bis(4,4'-(3,4-difluorophenyl-N-methylaminoethoxyboryl)benzyl) ether;
bis(4,4'-(3,4-difluorophenyl-N,N-dimethylaminoethoxyboryl)benzyl) ether;
bis(4,4'-(3,4-difluorophenyl-N-aminoethylaminoethoxyboryl)benzyl) ether;
bis(4,4'-(3-chloro-4-methylphenyl-aminoethoxyboryl)benzyl) ether;
bis(4,4'-(3-chloro-4-methylphenyl-N-methylaminoethoxyboryl)benzyl) ether;
bis(4,4'-(3-chloro-4-methylphenyl-N,N-dimethylaminoethoxyboryl)benzyl) ether;
bis(4,4'-(3-chloro-4-methylphenyl-2-piperidylmethyloxyboryl)benzyl) ether;
bis(4,4'-(p-trifluoromethylphenyl-N,N-dimethylaminoethoxyboryl)benzyl) ether;
bis(4,4'-(p-trifluoromethylphenyl-asparagineboryl)benzyl) ether;
bis(4,4'-(p-trifluoromethylphenyl-aminoethoxyboryl)benzyl) ether;
(4-phenyl-N-methylaminoethoxyborylphenyl) 4'-(N-methylaminoethoxyborylbenzyl) ether;
(4-phenyl-N,N-dimethylaminoethoxyborylphenyl) 4'-(N,N-dimethylaminoethoxyborylbenzyl) ether;
(4-phenyl-2-pyridylmethoxyborylphenyl) (4'-phenyl-2-pyridylmethoxyborylbenzyl) ether;
4-(phenyl-p-methoxyphenyl-2-pyridylmethoxyboryl)-phenyl 4'(p-methoxyphenyl-2-pyridylmethoxyboryl)benzyl ether;
bis(4,4'-(phenyl-3-piperidyloxyboryl)phenyl) ether;
bis(4,4'-(phenyl-2-pyridylmethoxyboryl)phenyl) ether;
bis(4,4'-(phenyl-aminothioethoxyboryl)phenyl) ether;
bis(4,4'-(phenyl-2-amino-1-phenylethoxyboryl)phenyl) ether;
bis(4,4'-(phenyl-ornithineboryl)phenyl) ether;
bis(4,4'-(phenyl-2,3-diaminopropionic acid boryl)phenyl) ether;
bis(4,4'-(phenyl-lysineboryl)phenyl) ether;
bis(4,4'-(phenyl-2-pyrrolidinemethoxyboryl)phenyl) ether;
bis(4,4'-(naphthylhydroxyboryl)phenyl) ether;
bis(4,4'-(tolylhydroxyboryl)phenyl) ether;
bis(4,4'-(naphthyl-aminoethoxyboryl)phenyl) ether;
bis(4,4'-(naphthyldimethylaminoethoxyboryl)phenyl) ether;
bis(4,4'-(naphthyl-2-pyridylmethoxyboryl)phenyl) ether;
bis(4,4'-(naphthylglutamineboryl)phenyl) ether;
bis(4,4'-(naphthyl-2,4-diaminopropionic acid boryl)phenyl) ether;
bis(4,4'-(tolyldimethylaminoethoxyboryl)phenyl) ether;
bis(4,4'-(tolylpiperazylethoxyboryl)phenyl) ether;
bis(4,4'-(tolylglutamineboryl)phenyl) ether;
bis(4,4'-(tolyllysineboryl)phenyl) ether;
bis(4,4'-(phenyl-2-amino-1-phenylethoxyboryl)benzyl) ether;
bis(4,4'-(phenyl-aminothioethoxyboryl)benzyl) ether;
bis(4,4'-(phenyl-2-pyrrolidinemethoxyboryl)benzyl) ether;
bis(4,4'-(phenyl-2,4-diaminobutyric acid boryl)benzyl) ether;
bis(4,4'-(phenyl-butylaminoethoxyboryl)benzyl) ether;
bis(4,4'-(phenyl-phenylaminoethoxyboryl)benzyl) ether;
bis(4,4'-(phenyl-benzylaminoethoxyboryl)benzyl) ether;
bis(4,4'-(phenyl-N-methylpiperidine-methoxyboryl)benzyl) ether;
bis(4,4'-(phenyl-1-methyl-2-aminoethoxyboryl)benzyl) ether;
bis(4,4'-(phenyl-1-piperidylethoxyboryl)benzyl) ether;
bis(3,3'-(phenyl-2-pyrrolidinomethoxyboryl)benzyl) ether;
bis(3,3'-(phenyl-aminothioethoxyboryl)benzyl) ether;
bis(3,3'-(phenyl-2-phenyl-2-aminoethoxyboryl)benzyl) ether;
bis(3,3'-(phenyl-2-piperazylmethoxyboryl)benzyl) ether;
bis(3,3'-(phenyl-dimethylaminoethoxyboryl)benzyl) ether;
bis(3,3'-(phenyl-1-methyl-2-aminoethoxyboryl)benzyl) ether;
bis(3,3'-(phenyl-2-piperidylethoxyboryl)benzyl) ether;
bis(3,3'-(phenyl-2-pyridylmethoxyboryl)benzyl) ether;
bis(3,3'-(phenyl-2-amino-1-phenylethoxyboryl)benzyl) ether;
bis(3,3'-(phenyl-N-methylethoxyboryl)benzyl) ether;
bis(3,3'-(phenyl-N-aminoethyl-1-methyl-3-aminopropoxyboryl)benzyl) ether;
bis(3,3'-(phenyl-glutamineboryl)benzyl) ether;
bis(3,3'-(phenyl-2,4-diaminobutyric acid boryl)benzyl) ether;
bis(3,3'-(phenyl-N-butylaminoethylboryl)benzyl) ether;
bis(3,3'-(phenyl-asparagineboryl)benzyl) ether;

bis(3,3'-(phenyl-lysineboryl)benzyl) ether;
bis(3,3'-(phenyl-ornithineboryl)benzyl) ether;
bis(4,4"-(phenyl-2-methyl-8-quinolinooxyboryl)phenyl) ether;
bis(4,4"-(phenyl-2-pyridylmethoxyboryl)phenyl) ether;
bis(4,4"-(phenyl-2-benzyl-2-amino-ethoxyboryl)benzyl) ether;
bis(4,4"-(phenyl-2-benzyl-2-amino-ethoxyboryl)phenyl) ether;
bis(3,3'-(phenyl-2-benzyl-2-amino-ethoxyboryl)phenyl) ether;
bis(4,4'-(phenyl-2-phenyl-2-amino-ethoxyboryl)benzyl) ether; and
salts thereof.

Examples of the suitable compounds having a CCE $IC_{50}$ of less than 3 μM in the present invention are listed as follows:
bis(4,4'-(phenylhydroxyboryl)phenyl) ether;
bis(4,4'-(phenylaminoethoxyboryl)phenyl) ether;
bis(3,3'-(phenylaminoethoxyboryl)benzyl) ether;
(3-(phenylhydroxyboryl)benzyl) (4-(phenylhydroxyboryl)benzyl) ether;
(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
(2-(phenylaminoethoxyboryl)benzyl) (3-(phenylaminoethoxyboryl)benzyl) ether;
4,4'-(4-methylphenylaminoethoxyboryl)diphenyl;
(4-phenylhydroxyborylphenyl) (4'-phenylhydroxyborylbenzyl) ether;
(4-phenylaminoethoxyborylphenyl) (4'-phenylaminoethoxyborylbenzyl) ether;
(4-(2-thiopheneaminoethoxyboryl)phenoxyethyl) (4'-(2-thiopheneaminoethoxyboryl)benzyl) ether;
(4-trifluoromethylphenylhydroxyborylphenyl) (4'-trifluoromethylphenylhydroxyborylbenzyl) ether;
(4-trifluoromethylphenylaminoethoxyborylphenyl) (4'-trifluoromethylphenylaminoethoxyborylbenzyl) ether;
4,5-di(phenylaminoethoxyboryl)-2,7-di-t-butyl-9,9-dimethylxanthrene;
bis(4,4'-(phenyl-N-methylaminoethoxyboryl)phenyl) ether;
(4'-trifluoromethylphenyl-N-methylethoxyboryl)-4-phenyl (4'-trifluoromethylphenyl-N-methylethoxyboryl)-4-benzyl ether;
bis(3,3'-(phenyl-N,N-dimethylaminoethoxyboryl)benzyl) ether;
bis(4,4'-(phenyl-2-pyridylmethoxyboryl)benzyl) ether;
bis(4,4'-(3-chloro-4-methylphenyl-hydroxyboryl)benzyl) ether;
bis(4,4'-(p-methoxyphenyl-aminoethoxyboryl)benzyl) ether;
bis(4,4'-(p-methoxyphenyl-N-methylaminoethoxyboryl)benzyl) ether;
bis(4,4'-(3-chloro-4-methylphenyl-aminoethoxyboryl)benzyl) ether;
bis(4,4'-(3-chloro-4-methylphenyl-N-methylaminoethoxyboryl)benzyl) ether;
bis(4,4'-(3-chloro-4-methylphenyl-N,N-dimethylaminoethoxyboryl)benzyl) ether;
bis(4,4'-(3-chloro-4-methylphenyl-2-piperidylmethyloxyboryl)benzyl) ether;
bis(4,4'-(p-trifluoromethylphenyl-N,N-dimethylaminoethoxyboryl)benzyl) ether;
bis(4,4'-(p-trifluoromethylphenyl-aminoethoxyboryl)benzyl) ether;
(4-phenyl-N-methylaminoethoxyborylphenyl) 4'-(N-methylaminoethoxyborylbenzyl) ether;
(4-phenyl-N,N-dimethylaminoethoxyborylphenyl) 4'-(N,N-dimethylaminoethoxyborylbenzyl) ether;
(4-phenyl-2-pyridylmethoxyborylphenyl) (4'-phenyl-2-pyridylmethoxyborylbenzyl) ether;
bis(4,4'-(phenyl-ornithineboryl)phenyl) ether;
bis(4,4'-(phenyl-2-pyrrolidinemethoxyboryl)benzyl) ether;
bis(4,4'-(phenyl-butylaminoethoxyboryl)benzyl) ether;
bis(4,4'-(phenyl-N-methylpiperidine-methoxyboryl)benzyl) ether;
bis(3,3'-(phenyl-2-amino-1-phenylethoxyboryl)benzyl) ether;
bis(3,3'-(phenyl-N-methylethoxyboryl)benzyl) ether;
bis(3,3'-(phenyl-N-aminoethyl-1-methyl-3-aminopropoxyboryl)benzyl) ether;
bis(3,3'-(phenyl-N-butylaminoethylboryl)benzyl) ether;
bis(4,4'-(phenyl-2-phenyl-2-amino-ethoxyboryl)benzyl) ether; and
salts thereof.

Examples of the suitable compounds having a CCE $IC_{50}$ of 1 μM or less in the present invention are listed as follows:
bis(4,4'-(phenylaminoethoxyboryl)phenyl) ether;
bis(3,3'-(phenylaminoethoxyboryl)benzyl) ether;
(3-(phenylhydroxyboryl)benzyl) (4-(phenylhydroxyboryl)benzyl) ether;
(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
(2-(phenylaminoethoxyboryl)benzyl) (3-(phenylaminoethoxyboryl)benzyl) ether;
(4-trifluoromethylphenylhydroxyborylphenyl) (4'-trifluoromethylphenylhydroxyborylbenzyl) ether;
bis(4,4'-(phenyl-N-methylaminoethoxyboryl)phenyl) ether;
(4'-trifluoromethylphenyl-N-methylaminoethoxyboryl)-4-phenyl (4'-trifluoromethylphenyl-N-methylaminoethoxyboryl)-4-benzyl ether;
bis(4,4'-(phenyl-2-pyridylmethoxyboryl)benzyl) ether;
bis(4,4'-(p-methoxyphenyl-N-methylaminoethoxyboryl)benzyl) ether;
(4-phenyl-N-methylaminoethoxyborylphenyl) 4'-(N-methylaminoethoxyborylbenzyl) ether;
bis(4,4'-(phenyl-ornithineboryl)phenyl) ether;
bis(3,3'-(phenyl-2-amino-1-phenylethoxyboryl)benzyl) ether;
bis(3,3'-(phenyl-N-methylethoxyboryl)benzyl) ether;
bis(3,3'-(phenyl-N-butylaminoethylboryl)benzyl) ether; and
salts thereof.

Examples of the suitable compounds having a CCE $IC_{50}$ of 500 nM or less in the present invention are listed as follows:
bis(4,4'-(phenylaminoethoxyboryl)phenyl) ether;
bis(3,3'-(phenylhydroxyboryl)benzyl) ether;
bis(3,3'-(phenylaminoethoxyboryl)benzyl) ether;
(3-(phenylhydroxyboryl)benzyl) (4-(phenylhydroxyboryl)benzyl) ether;
(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
(2-(phenylaminoethoxyboryl)benzyl) (3-(phenylaminoethoxyboryl)benzyl) ether; and
salts thereof.

Examples of the suitable compounds having a CCE $IC_{50}$ of 200 nM or less in the present invention are listed as follows:
bis(4,4'-(phenylaminoethoxyboryl)phenyl) ether;
bis(3,3'-(phenylhydroxyboryl)benzyl) ether;
bis(3,3'-(phenylaminoethoxyboryl)benzyl) ether;

(3-(phenylhydroxyboryl)benzyl) (4-(phenylhydroxyboryl) benzyl) ether;
(3-(phenylaminoethoxyboryl)benzyl) (4-(phenylaminoethoxyboryl)benzyl) ether; and
salts thereof.

The compound of the present invention may be converted into a pharmaceutically acceptable non-toxic salt by a known method. Examples of the non-toxic salt include alkali metal salts, alkali earth metal salts, amine salts, acid addition salts and solvates (including hydrates). The non-toxic salt is preferably water-soluble.

Suitable non-toxic salts include salts of alkali metals such as potassium and sodium; salts of alkali earth metals such as calcium and magnesium; and salts of organic amines such as triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine, and are preferably salts of alkali metals.

Suitable acid addition salts include inorganic acid salts such as hydrochlorides, hydrobromides, sulfates, phosphates and nitrate; or organic acid salts such as acetates, trifluoroacetates, lactates, tartrates, oxalates, fumarates, maleates, citrates, benzoates, methanesulfonates, ethanesulfonates, benzenesulfonates, toluenesulfonates, isethionates, glucuronates and gluconates.

The bisboron compound of the present invention also includes a solvate. The solvate is a combination of the compound of the present invention and a pharmaceutically acceptable solvent (such as water or an organic solvent) in a stoichiometric or non-stoichiometric ratio, in particular, a crystal form.

The compound of the present invention represented by the general formula (I) can be produced by the method described below or the method described in examples.

The compound of the present invention can be produced by the method shown in the following scheme, for example. In the scheme, B, $R_1$, $R_2$, $R_3$ and X are the same as described above.

A bislithium compound Li—X—Li is synthesized by allowing an alkyllithium (such as sec-butyllithium) to act on a bisbromo compound (Br—X—Br) (Formula (1)).

On the other hand, $R_1$Li is synthesized by allowing an alkyllithium (such as sec-butyllithium) to act on an aromatic bromide $R_1$—Br (Formula (2)).

An aryldialkoxyborane $R_1$—B(OAlk)$_2$, wherein Alk represents a C1-4 alkyl group, is synthesized by allowing a trialkoxyborane to act on the $R_1$Li (Formula (3)).

Li—X—Li is reacted with $R_1$—B(OAlk)$_2$ (Formula (4)).

The resulting product is treated with acid water to give a target compound $R_1$—B(OH)—X—B(OH)$R_1$ (Formula (5)).

2-Ethanolamine is allowed to act on $R_1$—B(OH)—X—B(OH)$R_1$ to give another target compound $R_1$—B(OCH$_2$CH$_2$NH$_2$)—X—B(OCH$_2$CH$_2$NH$_2$)—$R_1$ (Formula (6)).

[Formula 3]

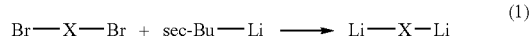
(1)

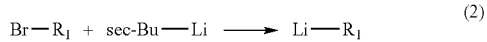
(2)

(3)

-continued

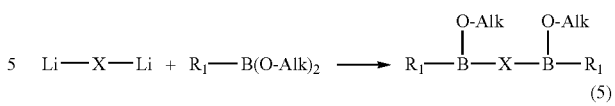
(4)

(5)

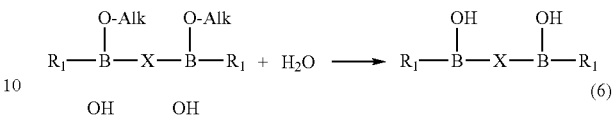
(6)

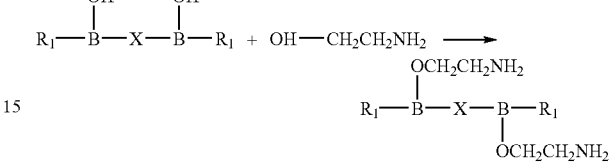

$R_1$—B(SCH$_2$CH$_2$NH$_2$)—X—B(SCH$_2$CH$_2$NH$_2$)—$R_1$ can be obtained by carrying out reaction using 2-aminoethylthiol as a thiol compound, for example, in place of 2-ethanolamine in the Formula (6).

As described above, when a compound having a hydroxy, carboxyl or thiol group (HO—$R_3$; HOOC—$R_3$; or HS—$R_3$) is reacted with $R_1$—B(OH)—X—B(OH)$R_1$ in the Formula (6), it is possible to give $R_1$—B(OR$_3$)—X—B(OR$_3$)$R_1$ or $R_1$—B(SR$_3$)—X—B(SR$_3$)$R_1$, wherein $R_3$ is as defined above. The reaction optionally may be carried out by stirring the reaction substances in the presence of an organic solvent such as ethanol at a temperature of room temperature to about 90° C.

Alternatively, the target compound bilaterally symmetric and/or bilaterally asymmetric with respect to X can be synthesized by the following reaction.

First, a trialkoxyborane (B(OAlk)$_3$) is allowed to act on $R_2$—Li to give $R_2$—B(OAlk)$_2$.

Next, when a mixture of $R_1$—B(OAlk)$_2$ and $R_2$—B(OAlk)$_2$ is used in the Formulas (4) to (6), $R_1$—B(YR$_3$)—X—B(YR$_3$)—$R_2$, $R_1$—B(YR$_3$)—X—B(YR$_3$)—$R_1$ or $R_2$—B(YR$_3$)—X—B(YR$_3$)—$R_2$ is obtained, wherein $R_1$ and $R_2$ are as defined above; and Y represents O or S.

Diarylboric acid is generally prepared from a Grignard reagent and arylboric acid dialkoxy. However, it is difficult to neatly prepare the target compound, presumably because it is difficult to completely react two bromine atoms in a bisbromo compound with magnesium or the solubility is decreased. Therefore, the lithium method shown in the scheme is preferable for synthesis of the bisboron compound.

The reaction using a lithium compound or lithium reagent is preferably carried out in an organic solvent such as ether at a temperature of −78° C. After the reaction, treatment is carried out with an acid such as dilute hydrochloric acid.

The starting material and each reagent are themselves known or can be produced according to a known method.

In each reaction of the scheme, the reaction product optionally may be purified by a common purification means, for example, a method such as distillation under normal pressure or reduced pressure; solvent extraction; salting-out; chromatography such as high performance liquid chromatography (HPLC), thin layer chromatography (TLC), silica gel column chromatography, reverse phase column chromatography or ion exchange column chromatography; or recrystallization. Purification may be carried out for each reaction or after completion of some reactions.

The target bisboron compound can be identified based on NMR, IR or mass spectral analysis, TLC analysis, elemental analysis, melting point or the like.

The action of inhibiting the intracellular calcium concentration, that is, the action of inhibiting capacitative calcium entry or endogenous calcium release by the bisboron compound of the present invention may be measured by the following assay, for example.

(Assay of Capacitative Calcium Entry Inhibition)

Fura-2 acetoxymethyl ester as a calcium sensitive fluorescent dye is introduced into an $IP_3$ receptor-deficient strain prepared from a chicken-derived cell line DT40 (H. Iwasaki et al., Receptors and Channels 7: 429-439, 2001). Its 510 nm fluorescence obtained at 340 nm and 380 nm is measured and the fluorescence ratio F340/380 is measured to determine the intracellular calcium ion concentration. Next, thapsigargin (an endoplasmic reticulum calcium ion pump inhibitor) is allowed to act without calcium ion in an extracellular fluid to deplete an intracellular calcium store. Calcium chloride at a final concentration of 2 mM is added to the extracellular fluid. The $IC_{50}$ value is calculated by estimating the effect of each compound on the degree of increase in the intracellular calcium concentration at the time of the addition.

(Assay of Endogenous Calcium Release Inhibition)

A mouse cerebellum was removed, homogenated and centrifuged (12,000 g, 15 min) according to the method of S. Nakade et al. [Biochem. J., 277; 125-131 (1991)]. Further, the supernatant was centrifuged (105,000 g, 60 min). To the precipitate were added 2 µM fura2, 1.25 mM ATP, 10 V/ml creatine kinase, 10 mM phosphocreatine and 2.5 µg/ml oligomycin, and calcium was allowed to be taken in a microsome. Next, $IP_3$ was added, and the released calcium was measured using 500 nm fluorescence obtained by two-wavelength excitation at 340 nm and 380 nm and the fluorescence ratio F340/380 was determined. The ratio of calcium release in the presence of a test drug was determined and the $IC_{50}$ value was calculated, based on calcium release occurring when $IP_3$ is at 30 nM as 100%.

When capacitative calcium entry (CCE) inhibitory activity of the compound of the present invention was measured, it was verified that the compound significantly inhibits an increase in the intracellular calcium concentration. Specifically, while most of the bisboron compounds of the present invention were effective at a CCE $IC_{50}$ of less than 3 µM and some of them were effective at an extremely low concentration of 50 nM to 1 µM, a monoboron compound having one boron atom such as (2-aminoethoxy)diphenylborane was effective only at a high concentration of 5 µM.

Accordingly, the present invention provides a composition for controlling the intracellular calcium concentration, characterized in that the composition comprises the bisboron compound or a salt thereof as an active ingredient.

Examples of the composition include pharmaceuticals, food and drinks (such as health foods) and research reagents.

It has also been verified that the compound of the present invention has sufficiently low toxicity and is sufficiently safe for use in pharmaceuticals, food and drinks and the like.

The bisboron compound of the present invention has an action of strongly inhibiting an increase in the intracellular calcium concentration, and thus is useful for control of vasoconstriction or vascular permeability; control of the respiratory tract; adjustment of gastrointestinal tract movement, neuronal differentiation or nerve growth cone; and control of pheromone reception, smooth muscle contraction or the like. Specifically, the compound of the present invention can be used as an active ingredient in a pharmaceutical or food and drink (in particular, a health food) for treatment, alleviation or prevention of a disease caused by an increase in the intracellular calcium concentration, for example, a disease such as ischemic heart or brain disease, cardiac hypertrophy, renal disease (such as glomerulosclerosis), hypertension, cerebral vasospasm, pancreatitis, asthma, immunodeficiency, allergic disease or Alzheimer's disease.

The compound of the present invention may be administered to a patient having the above-described disease alone or as a concomitant drug by combination with another drug.

The concomitant drug of the compound of the present invention and the other drug may be administered as a formulation having both ingredients formulated in one preparation, or may be administered as separate preparations. The administration of separate preparations includes coadministration and time-lag administration. In the time-lag administration, it is possible to administer the compound of the present invention first and the other drug later, or it is possible to administer the other drug first and the compound of the present invention later. Each ingredient may be administered by the same method or different methods. The weight ratio of the compound of the present invention to the other drug is not particularly limited and may be appropriately any ratio according to the symptom of the patient.

Usually, the compound of the present invention represented by the general formula (I) may be systemically or topically, orally or parenterally administered.

The dose varies according to the age, weight, symptom, therapeutic effect, administration method, treatment time and the like. However, usually, a dose of 1 mg to 1000 mg per adult may be orally administered once to several times a day. Alternatively, a dose of 0.1 mg to 100 mg per adult may be parenterally administered (preferably intravenously administered) once to several times a day or may be continuously intravenously administered over 1 to 24 hours a day.

Obviously, since the dose varies according to various conditions as described above, a dose smaller than the above dose may be sufficient, and a dose over the above range may be necessary.

When administered, the compound of the present invention can be used as an oral solid preparation or oral liquid preparation for oral administration and as an injection, external preparation, suppository or the like for parenteral administration.

The oral solid preparation for oral administration includes tablets, pills, capsules, powders and granules. Capsules include hard capsules and soft capsules.

In such an oral solid preparation, one or more active substances are used directly, or as mixed with an excipient (such as lactose, mannitol, glucose, microcrystalline cellulose or starch), a binder (such as hydroxypropylcellulose, polyvinylpyrrolidone or magnesium aluminometasilicate), a disintegrant (such as calcium carboxymethylcellulose), a lubricant (such as magnesium stearate), a stabilizer, a solubilizer (such as glutamic acid or aspartic acid) and the like and prepared according to a conventional method. The oral solid preparation optionally may be coated with a coating agent (such as saccharose, gelatin, hydroxypropylcellulose or hydroxypropylmethylcellulose phthalate), or may be coated with two or more layers. The preparation may be in such a form as a control release preparation or enteric coated preparation by such coating. Further, the preparation includes capsules of a substance capable of being absorbed such as gelatin.

The oral liquid preparation for oral administration includes pharmaceutically acceptable solutions, suspensions, emulsions, syrups and elixirs. In such a liquid preparation, one or more active substances are dissolved, suspended or emulsified in a diluent generally used (such as purified water, ethanol or their mixed solution). The liquid preparation may further contain a wetting agent, a suspending agent, an emulsifier, a stabilizer, a sweetener, a flavor, an aromatic, a preservative, a buffer and the like conventionally used for a preparation.

The injection for parenteral administration includes a solution, a suspension, an emulsion, and a solid injection dissolved or suspended in a solvent before use. In the injection used, one or more active substances are dissolved, suspended or emulsified in a solvent. Examples of the solvent used include distilled water for injection, saline, vegetable oil, alcohols such as propylene glycol, polyethylene glycol and ethanol, and combinations thereof. The injection may further contain a stabilizer (amino acid such as lysine or methionine; or sugar such as trehalose), a solubilizer (such as glutamic acid, aspartic acid or polysolvate 80 (registered trademark)), a suspending agent, an emulsifier, a soothing agent, a buffer, a preservative and the like. The injection is prepared by sterilization in the final step or aseptic manipulation. Alternatively, it is possible to produce a sterile solid preparation such as a lyophilized product and dissolve the preparation in a sterilized or sterile distilled water for injection or another solvent before use.

Other preparations for parenteral administration include an external liquid preparation, an ointment, a liniment, an inhalant, a spray, a suppository and a pessary for intravaginal administration, which contain one or more active substances and are formulated by a conventional method.

The spray may contain a stabilizer such as sodium bisulfite; and a buffer providing isotonicity, for example, an isotonizing agent such as sodium chloride, sodium citrate or citric acid, in addition to a diluent generally used.

As the excipient, the diluent and the additive, those generally used in the pharmaceutical industry can be used here. For example, it is possible to refer to the preparations and preparation methods described in Remington: The Science and Practice of Pharmacy 9th edition (1995) MACK PUBLISHING COMPANY (United States).

When the composition of the present invention is a food and drink, in particular, a health food, the composition can be provided as a product containing the compound of the present invention as an active ingredient using an excipient, a diluent, an additive and the like usually used for foods or pharmaceuticals. The form of the food and drink is, but is not limited to, a drink, granules, tablets or a gel. Alternatively, the compound of the present invention can be mixed with an existing food and drink.

The present invention will be described in detail by way of the following examples; however, the scope of the present invention is not limited by these examples.

EXAMPLES

In the following examples, the solvent in parentheses shown in chromatographic separation and TLC (silica gel; $R_f$) represents an elution solvent or developing solvent used, and the ratio represents a volume ratio. The solvent in parentheses shown in NMR represents a solvent used for measurement.

Further, the CCE inhibitory assay was carried out according to the above method.

Example 1

Bis(4,4'-(phenylhydroxyboryl)phenyl) ether

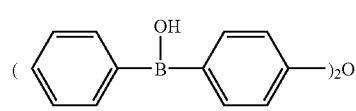

[Formula 4]

4,4'-Dibromodiphenyl ether (330 mg) was dissolved in 10 mL of ether, and the solution was cooled to −78° C. After addition of 2 mL of a 1 M sec-BuLi solution, the mixture was stirred for one hour (solution A).

Bromobenzene (221 µL) was dissolved in 8 mL of ether, and the solution was cooled to −100° C. sec-BuLi (a 1 M solution, 2.25 mL) was gradually added, and the mixture was brought to −78° C. over 25 minutes. After addition of 0.46 mL of triisopropoxyborane thereto, the mixture was stirred for 1.5 hours. The solution A was added to the solution at once. Then, the mixture was gradually returned to room temperature from −78° C. and stirred overnight. Aqueous dilute hydrochloric acid was added, and the mixture was stirred. The organic layer was concentrated and applied to a silica gel column to give 250 mg of the entitled compound.

$R_f$=0.45 (EtOAc, Hexane 1:1)

NMR (CDCl$_3$) 6.7-7.4 (m)

CCE: 50% inhibition at 3 µM

Example 2

Bis(4,4'-(phenylaminoethoxyboryl)phenyl) ether

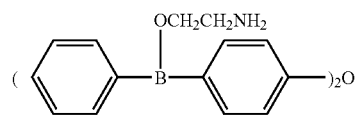

[Formula 5]

Bis(4,4'-(phenylhydroxyboryl)phenyl) ether (195 mg) was dissolved in 3 mL of ethanol. After addition of 68 mg of ethanolamine, the mixture was stirred for 35 minutes and concentrated under reduced pressure. Ether was added to precipitate 250 mg of the entitled compound as crystals.

NMR (DMSO-d$_6$) 2.82 (t, 4H, J=5.7 Hz), 3.75 (t, 4H, J=5.7 Hz), 6.7-6.74 (m, 4H), 7.0-7.06 (m, 2H), 7.10-7.15 (m, 4H), 7.31-7.49 (m, 8H)

Capacitative calcium entry (CCE) inhibitory action of this compound

CCE: 100% inhibition at 1 µM, 100% inhibition at 0.3 µM

CCE: 80% inhibition at 0.1 µM

IC$_{50}$=80 nM

Example 3

Bis(4,4'-(3-chloro-4-methylphenylhydroxyboryl)benzyl) ether

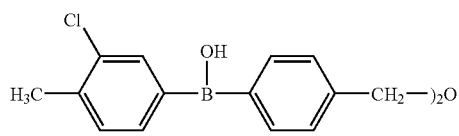

[Formula 6]

Bis(4-bromobenzyl) ether (157 mg) was dissolved in 8 mL of ether, and the solution was cooled to −78° C. After addition of 2 mL of a 1 M sec-BuLi solution, the mixture was stirred for two hours (solution A). 4-Bromo-2-chlorotoluene (205 mg) was dissolved in 8 mL of ether, and the solution was cooled to −90° C. After addition of 2 mL of a 1 M sec-BuLi solution, the mixture was stirred for two hours. Triisopropoxyborane (0.46 mL) was added to the resulting solution, and the mixture was stirred for 1.5 hours. The solution A was added to the solution, and the mixture was gradually returned to room temperature and stirred overnight. Aqueous dilute hydrochloric acid was added, and the mixture was stirred. The organic layer was dried and then concentrated and applied to a silica gel column to give 77 mg of the entitled compound as a grease.

$R_f$=0.48 (EtOAc, Hexane 1:1)

NMR (CDCl$_3$) 2.35 (s, 6H), 4.53 (s, 4H), 7.1-8.2 (m, 14H)

Example 4

Bis(3,3'-(phenylhydroxyboryl)benzyl) ether

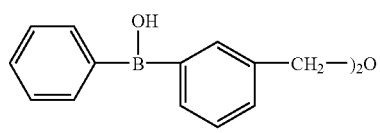

[Formula 7]

The entitled compound (23 mg) was obtained as a grease by the same method as in Example 1 using 180 mg of bis(3-bromobenzyl) ether and 242 μL of diisopropoxyphenylborane as main raw materials.

$R_f$=0.28 (EtOAc, Hexane 1:3)

NMR (CDCl$_3$) 4.48 (s, 4H), 7.0-7.8 (m, 16H)

Capacitative calcium entry (CCE) inhibitory action of this compound

CCE: 100% inhibition at 1 μM, 95% inhibition at 0.3 μM, 70% inhibition at 0.1 μM IC$_{50}$=80 nM

Example 5

Bis(3,3'-(phenylaminoethoxyboryl)benzyl) ether

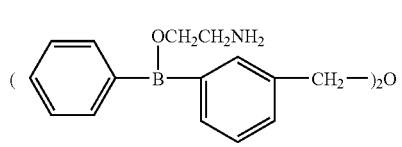

[Formula 8]

Bis(3,3'-(phenylhydroxyboryl)benzyl) ether (20 mg) was dissolved in 0.4 mL of ethanol. After addition of 8 mg of ethanolamine, the mixture was stirred for three hours and then dried in vacuo. The residue was recrystallized from chloroform-hexane to give 15 mg of the entitled compound.

NMR (CDCl$_3$) 2.91 (t, 4H, J=6.3 Hz), 3.84 (t, 4H, J=6.3 Hz), 4.38 (s, 4H), 6.95-7.10 (m, 10H), 7.24-7.36 (m, 8H),

Capacitative calcium entry (CCE) inhibitory action of this compound

CCE: 100% inhibition at 0.3 μM, 95% inhibition at 0.1 μM, 30% inhibition at 0.03 μM IC$_{50}$=50 nM

Example 6

Bis(4-(4-trifluoromethylphenylhydroxyboryl)benzyl) ether

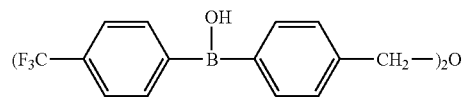

[Formula 9]

The entitled compound (52 mg) was obtained as a viscous liquid by the same method as in Example 1 using 180 mg of bis(4-bromobenzyl) ether, 225 mg of 4-bromo-α,α,α-trifluorotoluene and 0.225 mL of triisopropoxyborane as main raw materials.

$R_f$=0.47 (EtOAc, Hexane 1:1)

NMR (CDCl$_3$) 4.4 (s, 4H), 7.2-8.3 (m, 16H)

Example 7

Bis(4-(1-naphthylhydroxyboryl)benzyl) ether

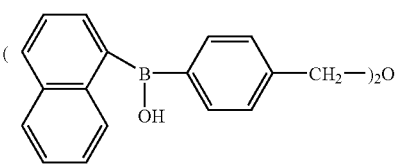

[Formula 10]

The entitled compound (79 mg) was obtained by the same method as in Example 1 using 180 mg of bis(4-bromobenzyl)

ether, 207 mg of 1-bromonaphthalene and 0.225 mL of triisopropoxyborane as main raw materials.
$R_f$=0.52 (EtOAc, Hexane 1:1)
NMR (CDCl$_3$) 4.6 (s, 4H), 7.8-8.3 (m, 22H)

Example 8

Bis(4-(fluorophenylhydroxyboryl)benzyl) ether

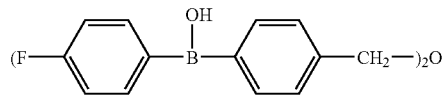
[Formula 11]

The entitled compound (46 mg) was obtained by the same method as in Example 1 using 180 mg of bis(4-bromobenzyl) ether, 165 mg of 4-fluorobromobenzene and 0.225 mL of triisopropoxyborane as main raw materials.
$R_f$=0.43 (EtOAc, Hexane 1:1)
NMR (CDCl$_3$) 4.63 (s, 4H), 7.4-8.4 (m, 16H)

Example 9

Bis(3-(4-methoxyphenylhydroxyboryl)benzyl) ether

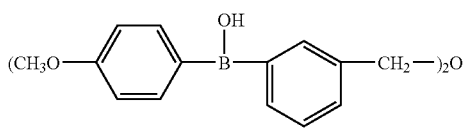
[Formula 12]

The entitled compound (62 mg) was obtained by the same method as in Example 3 using 357 mg of bis(3-bromobenzyl) ether, 374 mg of 4-methoxybromobenzene and 0.450 mL of triisopropoxyborane as main raw materials.
$R_f$=0.70 (EtOAc, Hexane 1:1)
NMR (CDCl$_3$) 3.78 (s, 6H), 4.48 (s, 4H), 5.8 (s, 2H), 6.8-6.9 (m, 12H), 7.2-7.40 (m, 4H)

Example 10

(3-(Phenylhydroxyboryl)benzyl) (4-(phenylhydroxyboryl)benzyl) ether

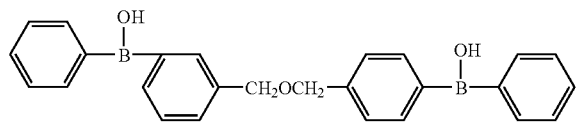
[Formula 13]

The entitled compound (56 mg) was obtained as a viscous liquid by the same method as in Example 1 using 180 mg of (3-bromobenzyl) (4-bromobenzyl) ether and 0.238 mL of diisopropoxyphenylborane as main raw materials.
$R_f$=0.43 (EtOAc, Hexane 1:2)
NMR (CDCl$_3$) 4.58 (m, 4H), 7.15-7.9 (m, 18H)

Capacitative calcium entry (CCE) inhibitory action of this compound
IC$_{50}$=200 nM Example 11

(2-(Phenylhydroxyboryl)benzyl) (3-(phenylhydroxyboryl)benzyl) ether

The entitled compound (58 mg) was obtained by the same method as in Example 3 using 357 mg of (2-bromobenzyl) (3-bromobenzyl) ether, 0.221 mL of bromobenzene and 0.46 mL of triisopropoxyborane as main raw materials.
$R_f$=0.55 (EtOAc, Hexane 1:1)
NMR (CDCl$_3$) 4.5-4.6 (m, 4H), 7.1-8.0 (m, 18H)

Example 12

(2-(Phenylhydroxyboryl)benzyl) (4-(phenylhydroxyboryl)benzyl) ether

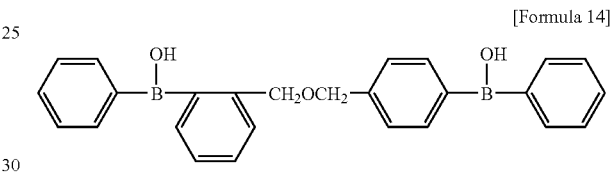
[Formula 14]

The entitled compound (22 mg) was obtained by the same method as in Example 1 using 357 mg of (2-bromobenzyl) (4-bromobenzyl) ether, 0.221 mL of bromobenzene and 0.46 mL of triisopropoxyborane as main raw materials.
$R_f$=0.65 (EtOAc, Hexane 1:1)
NMR (CDCl$_3$) 4.4-4.6 (m, 4H), 7.0-8.0 (m, 18H)
Capacitative calcium entry (CCE) inhibitory action of this compound
CCE: 100% inhibition at 3 μM, 80% inhibition at 1 μM, 10% inhibition at 0.3 μM
IC$_{50}$=500 nM Example 13

(3-(Phenylaminoethoxyboryl)benzyl) (4-(phenylaminoethoxyboryl)benzyl) ether

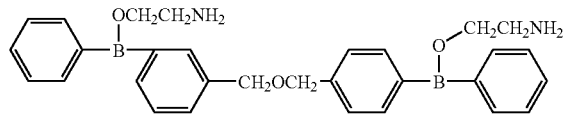
[Formula 15]

3-(Phenylhydroxyboryl)benzyl (4-(phenylhydroxyboryl) benzyl) ether (26 mg) was dissolved in 1 mL of ethanol. After addition of 8.6 mg of ethanolamine, the mixture was stirred for one hour and dried. Ether was added to the residue to give 30 mg of a solid.
NMR (CDCl$_3$) 2.53 (m, 4H), 2.75 (m, 4H), 4.08 (m, 4H), 4.42 (m, 4H), 7.0-7.3 (m, 18H)
Capacitative calcium entry (CCE) inhibitory action of this compound
IC$_{50}$=200 nM CCE: 100% inhibition at 0.3 μM, 80% inhibition at 0.2 μM
CCE: 10% inhibition at 0.1 μM

Example 14

Bis(3-(3-chloro-4-methylphenylhydroxyboryl)benzyl) ether

[Formula 16]

$(H_3C\text{-}\langle\text{Cl-phenyl}\rangle\text{-B(OH)-}\langle\text{phenyl}\rangle\text{-CH}_2\text{-})_2O$ The entitled compound (66 mg) was obtained as a viscous liquid by the same method as in Example 3 using 357 mg of bis(3-bromobenzyl) ether, 410 mg of 2-chloro-4-bromotoluene and 0.46 mL of diisopropoxyphenylborane as main raw materials.

$R_f$=0.71 (EtOAc, Hexane 1:1)
NMR (CDCl$_3$) 2.3 (s, 6H), 4.5 (s, 4H), 7.1-7.6 (m, 14H)

Example 15

(2-(Phenylaminoethoxyboryl)benzyl) (3-(phenylaminoethoxyboryl)benzyl) ether

[Formula 17]

The entitled compound (33 mg) was obtained from 29 mg of (2-(phenylhydroxyboryl)benzyl) (3-(phenylhydroxyboryl)benzyl) ether and 6.4 mg of ethanolamine.

NMR (CDCl$_3$) 2.6 (m, 4H), 3.50 (m, 4H), 3.65 (m, 4H), 4.3 (s, 2H), 4.67 (s, 2H), 7.0-7.6 (m, 18H)

CCE: 100% inhibition at 3 μM, 100% inhibition at 1 μM, 100% inhibition at 0.3 μM

Example 16

2-(Phenylaminoethoxyboryl)benzyl) (4-(phenylaminoethoxyboryl)benzyl) ether

[Formula 18]

The entitled compound (4 mg) was obtained from 9 mg of (2-(phenylhydroxyboryl)benzyl) (4-(phenylhydroxyboryl)benzyl) ether and 1.8 mg of ethanolamine.

NMR (CDCl$_3$) 2.60 (b, 4H), 2.86 (m, 4H), 3.55 (m, 4H), 4.5 (m, 4H), 7.0-7.5 (m, 18H)

Example 17

Bis(3-(4-fluorophenylhydroxyboryl)benzyl) ether

[Formula 19]

The entitled compound (48 mg) was obtained by the same method as in Example 1 using 357 mg of bis(3-bromobenzyl) ether and 350 mg of 4-fluorobromobenzene as main raw materials.

$R_f$=0.45 (EtOAc, Hexane 1:1)
NMR (CDCl$_3$) 4.6 (s, 4H), 7.0-8.2 (m, 16H)

Example 18

Bis(3-(4-fluorophenylaminoethoxyboryl)benzyl) ether

[Formula 20]

The entitled compound (12 mg) was obtained from 16 mg of bis(3-(4-fluorophenylhydroxyboryl)benzyl) ether and 3.0 mg of ethanolamine.

NMR (CDCl$_3$) 1.70 (m, 4H), 2.85 (m, 4H), 3.61 (m, 4H), 4.50 (s, 4H), 7.2-7.4 (m, 16H)

Example 19

Bis(4-(4-chloro-3-methyl-phenylhydroxyboryl)benzyl) ether

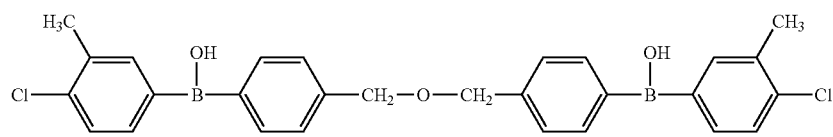

[Formula 21]

The entitled compound (69 mg) was obtained as a viscous liquid by the same method as in Example 1 using 357 mg of bis(4-bromobenzyl) ether, 410 mg of 4-chloro-3-methyl-bromobenzene and 0.459 mL of triisopropoxyborane as main raw materials.

$R_f$=0.57 (EtOAc, Hexane 1:1)

NMR (CDCl$_3$) 2.35 (s, 6H), 4.5 (s, 4H), 7.0-7.82 (m, 12H), 7.9-8.0 (m, 2H)

Example 20

Bis(4-(4-chloro-3-methyl-phenylaminoethoxyboryl) benzyl) ether

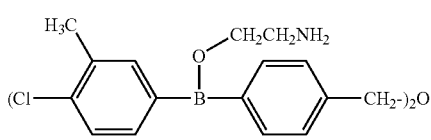

[Formula 22]

The entitled compound (15 mg) was obtained from 66 mg of bis(4-(4-chloro-3-methyl-phenylhydroxyboryl)benzyl) ether and 9 mg of ethanolamine.

NMR (CDCl$_3$) 2.32 (s, 6H), 2.42 (m, 4H), 2.85 (m, 4H), 3.62 (m, 4H), 4.54 (s, 4H), 7.10-7.40 (m, 14H)

Example 21

Bis(3-(3',4'-methylenedioxy-phenylhydroxyboryl) benzyl) ether

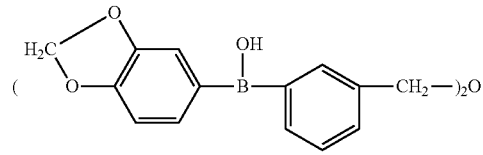

[Formula 23]

The entitled compound (52 mg) was obtained as a viscous liquid by the same method as in Example 1 using 357 mg of bis(3-bromobenzyl) ether, 402 mg of 4-bromo-1,2-methylenedioxy-benzene and 0.459 mL of triisopropoxyborane as main raw materials.

$R_f$=0.66 (EtOAc, Hexane 1:1)

NMR (CDCl$_3$) 4.58 (s, 4H), 5.96 (s, 4H), 6.7-7.9 (m, 14H)

Example 22

(3-(3-Chloro-4-methylphenylhydroxyboryl)benzyl) (4-(3-chloro-4-methylphenylhydroxyboryl)benzyl) ether

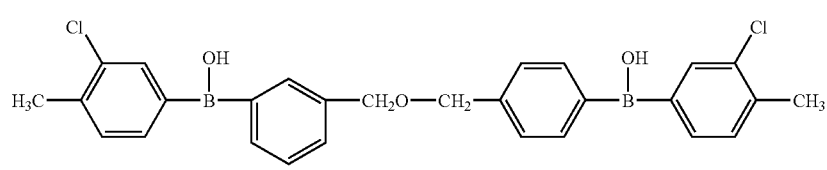

[Formula 24]

The entitled compound (38 mg) was obtained by the same method as in Example 1 using 357 mg of (3-bromobenzyl) (4-bromobenzyl) ether, 387 mg of 3-chloro-4-methyl-bromobenzene and 0.459 mL of triisopropoxyborane as main raw materials.

$R_f$=0.50 (EtOAc, Hexane 1:1)

NMR (CDCl$_3$) 2.33 (m, 6H), 4.5-4.6 (m, 4H), 7.0-7.5 (m, 14H)

Example 23

(3-(3',4',5'-Trifluorophenylhydroxyboryl)benzyl) (4-(3',4',5'-trifluorophenylhydroxyboryl)benzyl) ether

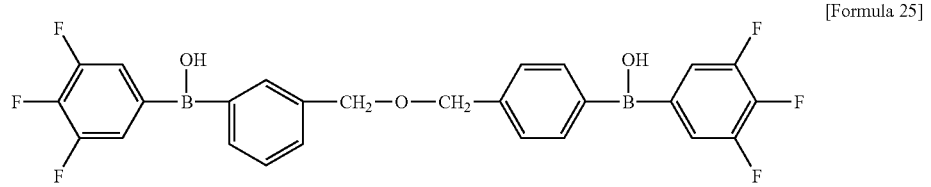

[Formula 25]

The entitled compound (36 mg) was obtained as a viscous liquid by the same method as in Example 1 using 357 mg of (3-bromobenzyl) (4-bromobenzyl) ether, 422 mg of 1-bromo-3,4,5-trifluorobenzene and 0.459 mL of triisopropoxyborane as main raw materials.

$R_f$=0.53 (EtOAc, Hexane 1:1)

NMR (CDCl$_3$) 4.59 (s, 4H), 7.2-7.4 (m, 12H)

Example 24

Bis(3-(4-methoxyphenylaminoethoxyboryl)benzyl) ether

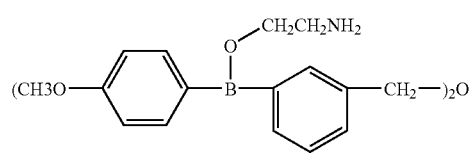

[Formula 26]

The entitled compound (28 mg) was obtained in the same manner as in Example 2 using 25 mg of bis(3-(4-methoxyphenylhydroxyboryl)benzyl) ether and 9 mg of ethanolamine.

NMR (CDCl$_3$) 2.9 (m, 4H), 3.4 (m, 4H), 3.7 (m, 4H), 3.78 (s, 6H), 4.6 (s, 4H), 6.8-7.3 (m, 16H)

Example 25

(3-(4-Chloro-3-methylphenylhydroxyboryl)benzyl) (2-(4-chloro-3-methylphenylhydroxyboryl)benzyl) ether

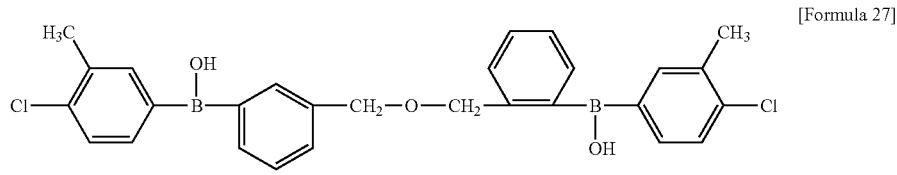

[Formula 27]

The entitled compound (35 mg) was obtained as a white solid by the same method as in Example 1 using 180 mg of (2-bromo-benzyl) (3-bromo-benzyl) ether, 205 mg of 4-chloro-3-methyl-bromobenzene and 0.225 mL of triisopropoxyborane as main raw materials.

$R_f$=0.75 (EtOAc, Hexane 1:1)

NMR (CDCl$_3$) 2.95 (s, 6H), 4.6 (m, 4H), 5.0 (s, 2H), 7.1-7.9 (m, 16H)

Example 26

Bis(3-(4-cyanophenylhydroxyboryl)benzyl) ether

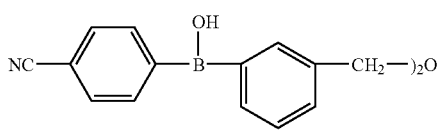

[Formula 28]

The entitled compound (37 mg) was obtained as a viscous liquid by the same method as in Example 1 using 180 mg of bis(3-bromobenzyl) ether, 182 mg of 4-cyano-bromobenzene and 0.225 mL of triisopropoxyborane as main raw materials.

$R_f$=0.75 (EtOAc, Hexane 1:1)

NMR (CDCl$_3$) 4.5-4.6 (m, 4H), 6.8-7.9 (m, 16H)

Example 27

Bis(3-(2'-thiophenylhydroxyboryl)benzyl) ether

[Formula 29]

The entitled compound (48 mg) was obtained as a viscous liquid by the same method as in Example 1 using 192 mg of 4,4'-bis(3-bromobenzyl) ether, 163 mg of 2-bromothiophene and 0.235 mL of triisopropoxyborane as main raw materials.

$R_f$=0.67 (EtOAc, Hexane 1:1)

NMR (CDCl$_3$) 4.51-4.56 (m, 4H), 6.8-8.05 (m, 14H)

Example 28

Bis(3-(1'-naphthylhydroxyboryl)benzyl) ether

[Formula 30]

The entitled compound (27 mg) was obtained as a viscous liquid by the same method as in Example 1 using 180 mg of bis(3-bromobenzyl) ether, 207 mg of 1-bromonaphthalene and 0.225 mL of triisopropoxyborane as main raw materials.

$R_f$=0.57 (EtOAc, Hexane 1:1)

NMR (CDCl$_3$) 4.4 (s, 4H), 7.0-7.8 (m, 22H)

Example 29

Bis(3-(2'-thiophenylhydroxyboryl)benzyl) ether

[Formula 31]

The entitled compound (22 mg) was obtained as a viscous liquid by the same method as in Example 1 using 357 mg of 4,4'-bis(4-bromobenzyl) ether, 326 mg of 2-bromothiophene and 0.459 mL of triisopropoxyborane as main raw materials.

$R_f$=0.57 (EtOAc, Hexane 1:1)

NMR (CDCl$_3$) 4.60 (s, 4H), 7.0-8.0 (m, 8H)

Example 30

Bis(4-(2-methoxy-5-fluorophenylhydroxyboryl)benzyl) ether

[Formula 32]

The entitled compound (31 mg) was obtained as a viscous liquid by the same method as in Example 1 using 357 mg of 4,4'-bis(4-bromobenzyl) ether, 205 mg of 2-methoxy-5-fluoro-bromobenzene and 0.459 mL of triisopropoxyborane as main raw materials.

$R_f$=0.59 (EtOAc, Hexane 1:1)

NMR (CDCl$_3$) 3.9 (s, 6H), 4.58 (s, 4H), 6.9-7.5 (m, 14H)

Example 31

Bis(4-(2-methoxy-5-fluorophenylaminoethoxyboryl)benzyl) ether

The entitled compound (12 mg) was obtained in the same manner as in Example 2 from 15 mg of bis(4-(2-methoxy-5-fluorophenylhydroxyboryl)benzyl) ether and 5 mg of ethanolamine.

NMR (CDCl$_3$) 2.89 (m, 4H), 3.22 (m, 4H), 3.86 (m, 6H), 4.08 (m, 4H), 6.7-7.76 (m, 12H)

Example 32

(3-(4-Chloro-3-methyl-phenylaminoethoxyboryl)benzyl) (2-(4-chloro-3-methyl-phenylaminoethoxyboryl)benzyl) ether

[Formula 33]

The entitled compound (13 mg) was obtained in the same manner as in Example 2 from 21 mg of 3-(4-chloro-3-methylphenylhydroxyboryl)benzyl (2-(4-chloro-3-methylphenylhydroxyboryl)benzyl) ether and 5 mg of ethanolamine.

NMR (CDCl$_3$) 2.25 (s, 6H), 2.90 (m, 4H), 3.42 (m, 4H), 3.9 (m, 4H), 4.28 (s, 2H), 4.35 (s, 2H), 6.9-7.7 (m, 14H)

Example 33

Bis(4-(3,4-difluorophenylhydroxyboryl)benzyl) ether

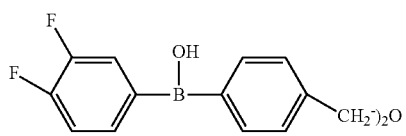

[Formula 34]

The entitled compound (44 mg) was obtained as a viscous liquid by the same method as in Example 1 using 357 mg of 4,4'-bis(4-bromobenzyl) ether, 386 mg of 3,4-difluoro-bromobenzene and 0.459 mL of triisopropoxyborane as main raw materials.

NMR (CDCl$_3$) 4.5-4.7 (m, 4H), 6.8-8.0 (m, 14H)

Example 34

Bis(4-(3,4-difluorophenylaminoethoxyboryl)benzyl) ether

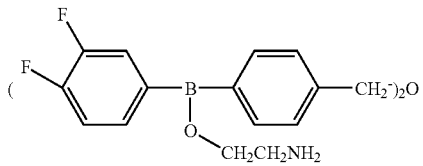

[Formula 35]

The entitled compound (32 mg) was obtained in the same manner as in Example 2 from 40 mg of bis(4-(3,4-difluorophenylhydroxyboryl)benzyl) ether and 11 mg of ethanolamine.

NMR (CDCl$_3$) 2.98 (m, 4H), 3.45 (m, 4H), 4.0 (m, 4H), 4.35 (m, 4H), 7.0-7.7 (m, 14H)

Example 35

(3-(3',4',5'-Trifluorophenylaminoethoxyboryl)benzyl) (4-(3',4',5'-trifluorophenylaminoethoxyboryl)benzyl) ether

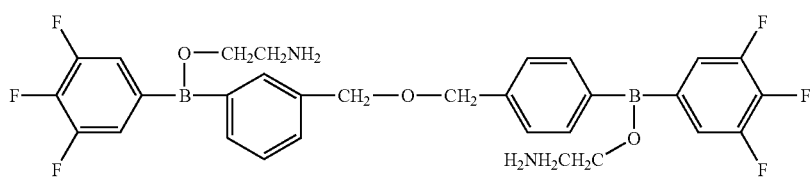

[Formula 36]

The entitled compound (14 mg) was obtained in the same manner as in Example 2 from 40 mg of 3-(3',4',5'-trifluorophenylhydroxyboryl)benzyl (4-(3',4',5'-trifluorophenylhydroxyboryl)benzyl) ether and 10 mg of ethanolamine.

NMR (CDCl$_3$) 2.86 (m, 4H), 3.80 (m, 4H), 4.12 (m, 4H), 4.4-4.5 (m, 4H), 7.1-7.6 (m, 12H)

Example 36

5,5'-(Phenylhydroxyboryl)-2,2'-dithiophene

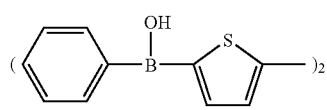

[Formula 37]

The entitled compound (31 mg) was obtained as a viscous liquid by the same method as in Example 1 using 324 mg of 5,5'-dibromo-2,2'-bithiophene, 0.211 mg of bromobenzene and 0.459 mL of triisopropoxyborane as main raw materials.

R$_f$=0.29 (EtOAc, Hexane 1:1)

NMR (CDCl$_3$) 5.72 (b, 2H), 6.7-7.9 (m, 14H)

Example 37

5,5'-(Phenylaminoethoxyboryl)-2,2'-dithiophene

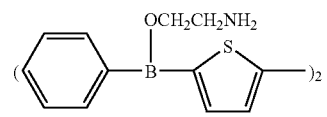

[Formula 38]

The entitled compound (8 mg) was obtained in the same manner as in Example 2 from 12 mg of 5,5'-(phenylhydroxyboryl)-2,2'-dithiophene and 4.6 mg of ethanolamine.

NMR (CDCl$_3$) 2.95 (m, 4H), 3.96 (m, 4H), 4.27 (m, 4H), 6.8-7.5 (m, 14H)

Example 38

3,5-Di(phenylaminoethoxyboryl)toluene

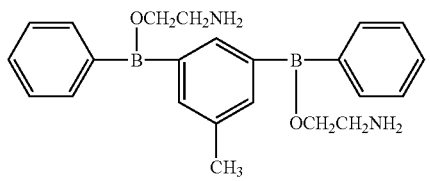

[Formula 39]

3,5-Dibromotoluene (373 mg) was dissolved in 8 mL of ether, and the solution was cooled to −78° C. After addition of 2 mL of a 1 M sec-BuLi solution, the mixture was stirred for two hours (solution A). Bromobenzene (0.317 mL) was dissolved in 8 mL of ether, and the solution was cooled to −100° C. After addition of 3 mL of a 1 M sec-BuLi solution, the mixture was stirred for 15 minutes. Triisopropoxyborane (0.685 mL) was added to the resulting solution, and the mixture was stirred at −78° C. for 1.5 hours. The solution A was added to the solution, and the mixture was gradually returned to room temperature and stirred overnight. Aqueous dilute hydrochloric acid was added, and the mixture was stirred. The organic layer was concentrated to dryness. A solution of 185 mg of ethanolamine in 20 mL of ethanol was added, and the mixture was stirred for one hour. The reaction solution was concentrated to dryness and dissolved in CH$_2$Cl$_2$. Hexane was added to precipitate 250 mg of the entitled compound as a solid.

$R_f$=0.6 (EtOAc, Hexane 1:1)

NMR (CDCl$_3$) 2.47 (s, 3H), 2.48 (s, 4H), 3.60 (s, 4H), 4.24 (m, 4H), 7.0-8.0 (m, 13H)

Example 39

2,5-Di(phenylhydroxyboryl)toluene

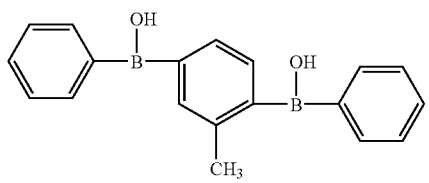

[Formula 40]

The entitled compound (50 mg) was obtained by the same method as in Example 1 using 375 mg of 2,5-dibromotoluene, 471 mg of bromobenzene and 0.658 mL of triisopropoxyborane as main raw materials.

$R_f$=0.6 (EtOAc, Hexane 1:1)

NMR (CDCl$_3$) 2.4 (s, 3H), 5.9 (m, 2H), 7.0-7.8 (m, 14H)

Example 40

2,2'-Di(phenylhydroxyboryl)-1,1'-binaphthyl

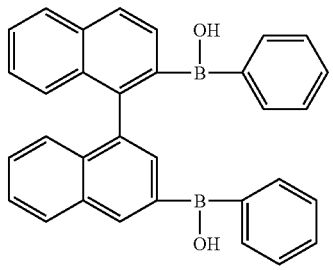

[Formula 41]

The entitled compound (140 mg) was obtained as a solid by the same method as in Example 1 using 412 mg of 2,2'-dibromo-1,1'-binaphthyl, 314 mg of bromobenzene and 0.459 mL of triisopropoxyborane as main raw materials.

$R_f$=0.6 (EtOAc, Hexane 1:1)

NMR (CDCl$_3$) 5.2 (b, 2H), 6.9-8.2 (m, 22H)

Example 41

2,2'-Di(phenylaminoethoxyboryl)-1,1'-binaphthyl

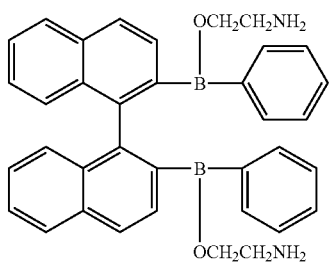

[Formula 42]

The entitled compound (50 mg) was obtained in the same manner as in Example 2 from 90 mg of 2,2'-di(phenylhydroxyboryl)-1,1'-binaphthyl and 26 mg of ethanolamine.

NMR (CDCl$_3$) 2.17 (m, 4H), 3.27 (m, 4H), 3.78 (m, 4H), 7.0-7.5 (m, 16H), 7.8-8.0 (m, 6H)

Example 42

Bis(4-(4-methylphenylhydroxyboryl)benzyl) ether

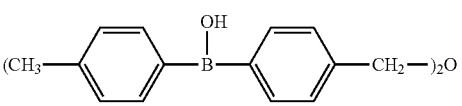

[Formula 43]

The entitled compound (101 mg) was obtained as a viscous liquid by the same method as in Example 1 using 357 mg of bis(4-bromobenzyl) ether, 342 mg of 4-bromotoluene and 0.459 mL of triisopropoxyborane as main raw materials.

R$_f$=0.57 (EtOAc, Hexane 1:1)

NMR (CDCl$_3$) 2.36 (s, 6H), 4.62 (s, 4H), 5.89 (b, 2H), 7.2-7.8 (m, 16H)

Example 43

Bis(4-(4-methylphenylaminoethoxyboryl)benzyl) ether

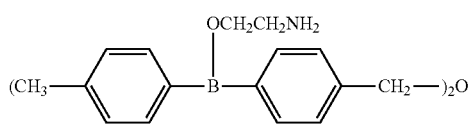

[Formula 44]

The entitled compound (30 mg) was obtained in the same manner as in Example 2 from 71 mg of bis(4-(4-methylphenylhydroxyboryl)benzyl) ether and 20 mg of ethanolamine.

NMR (CDCl$_3$) 2.13 (s, 6H), 3.00 (m, 4H), 3.27 (s, 4H), 3.93 (m, 4H), 4.56 (s, 4H), 7.3-7.52 (m, 16H)

Example 44

4,4'-(4-Methylphenylhydroxyboryl)diphenyl

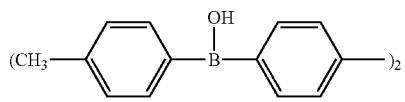

[Formula 45]

The entitled compound (89 mg) was obtained as a viscous liquid by the same method as in Example 1 using 312 mg of 4,4'-bromodiphenyl, 342 mg of 4-bromotoluene and 0.459 mL of triisopropoxyborane as main raw materials.

R$_f$=0.61 (EtOAc, Hexane 1:1)

NMR (CDCl$_3$) 2.42 (s, 6H), 5.94 (ms, 2H), 7.20- (m, 4H), 7.7-8.0 (m, 12H)

Example 45

4,4'-(4-Methylphenylaminoethoxyboryl)diphenyl

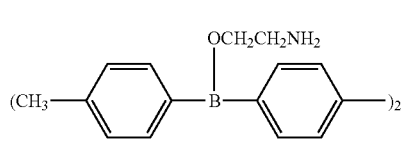

[Formula 46]

The entitled compound (60 mg) was obtained in the same manner as in Example 2 from 60 mg of 4,4'-(4-methylphenylhydroxyboryl)diphenyl and 20 mg of ethanolamine.

NMR (CDCl$_3$) 2.22 (s, 6H), 3.12 (m, 4H), 4.00 (m, 4H), 4.66 (m, 4H), 7.0-7.6 (m, 16H) 100% inhibition at 3 µM, 20% inhibition at 1 µM Example 46

4,4'-(4-Methylphenylhydroxyboryl)diphenyl ether

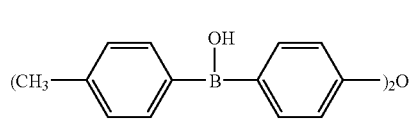

[Formula 47]

The entitled compound (145 mg) was obtained as a white solid by the same method as in Example 1 using 328 mg of 4,4'-dibromodiphenyl ether, 341 mg of 4-bromotoluene and 0.459 mL of triisopropoxyborane as main raw materials.

R$_f$=0.55 (EtOAc, Hexane 1:1)

NMR (CDCl$_3$) 2.40 (s, 6H), 5.85 (b, 2H), 6.8-8.0 (m, 16H)

Example 47

4,4'-(4-Methylphenylaminoethoxyboryl)diphenyl ether

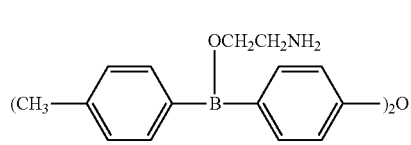

[Formula 48]

The entitled compound (83 mg) was obtained in the same manner as in Example 2 from 69 mg of (4-methylphenylhydroxyboryl)diphenyl ether and 22 mg of ethanolamine.

NMR (CDCl$_3$) 2.31 (s, 6H), 2.85 (m, 4H), 3.40 (m, 4H), 3.65 (m, 4H), 6.6-7.4 (m, 16H)

Example 48

4,4'-Bis(3-chloro-4-methyl-phenylaminoethoxyboryl)phenyl ether

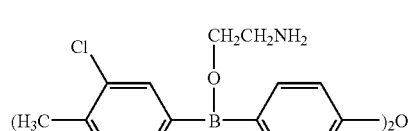

[Formula 49]

The entitled compound (58 mg) was obtained in the same manner as in Example 2 from 60 mg of 4,4'-((3-chloro-4-methyl-phenylhydroxyboryl)phenyl) ether and 13.4 mg of ethanolamine.

NMR (CDCl$_3$) 2.32 (s, 6H), 3.02 (t, 4H, J=5.9 Hz), 3.97 (t, 4H, J=5.9 Hz), 6.97 (d, 4H, J=7.0), 7.12 (d, 2H, J=7.5 Hz), 7.12 (d, 2H, J=7.5 Hz), 7.33 (d, 4H, J=7.0 Hz), 7.40 (s, 2H)

Example 49

(2-(Phenylhydroxyboryl)phenethyl) ((2-phenylhydroxyboryl)benzyl) ether

[Formula 50]

The entitled compound was obtained as a viscous liquid by the same method as in Example 1 using 2-bromophenethyl 2-bromobenzyl ether, 4-bromobenzene and triisopropoxyborane as main raw materials.

R$_f$=0.6 (EtOAc, Hexane 1:1)

NMR (DMSO-d$_6$) 3.14 (t, 2H, J=5.7 Hz) 3.93 (t, 2H J=5.7 Hz), 5.06 ((br, 2H), 7.16-7.29 (m, 5H), 7.35-7.47 (m, 1H), 7.53-7.56 (m, 2H), 7.62-7.65 (m, 1H), 7.75-7.79 (m, 1H), 7.90-7.94 (m, 2H)

Example 50

(2-(Phenylaminoethoxyboryl)phenethyl) ((2-phenylaminoethoxyboryl)benzyl) ether

[Formula 51]

The entitled compound (20 mg) was obtained in the same manner as in Example 2 from 46 mg of (2-(phenylhydroxyboryl)phenethyl) ((2-phenylhydroxyboryl)benzyl) ether and 14.2 mg of ethanolamine.

NMR (DMSO-d$_6$) 3.14 (t, 2H, J=5.7 Hz), 3.93 (t, 2H, J=5.7 Hz), 4.37 (br, 4H), 7.12-7.27 (m, 18H)

Example 51

(4-Phenylhydroxyborylphenyl) (4'-phenylhydroxyborylbenzyl) ether

[Formula 52]

The entitled compound (55 mg) was obtained as a white solid by the same method as in Example 3 using 342 mg of 4-bromophenyl 4'-bromobenzyl ether, 314 mg of 4-bromobenzene and 0.459 mL of triisopropoxyborane as main raw materials.

R$_f$=0.52 (EtOAc, Hexane 1:1)

NMR (CDCl$_3$) 5.10 (s, 2H), 5.80 (b, 2H), 6.9-7.8 (m, 18H)

CCE: 100% inhibition at 3 μM, 20% inhibition at 1 μM

Example 52

(4-Phenylaminoethoxyborylphenyl) (4'-phenylaminoethoxyborylbenzyl) ether

[Formula 53]

The entitled compound (25 mg) was obtained in the same manner as in Example 2 from 44 mg of (4-phenylhydroxyborylphenyl) (4'-phenylhydroxyborylbenzyl) ether and 14 mg of ethanolamine.

NMR (CDCl$_3$) 2.42 (m, 4H), 2.64 (m, 4H), 3.6 (m, 4H), 4.6 (s, 2H), 6.8-7.1 (m, 18H)

CCE: 100% inhibition at 3 μM

Example 53

(4-(2-Thiopheneaminoethoxyboryl)phenoxyethyl) (4'-(2-thiopheneaminoethoxyboryl)benzyl) ether

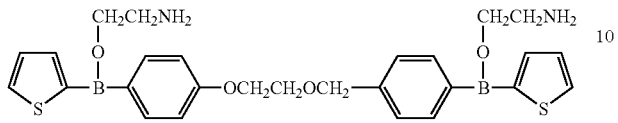

[Formula 54]

The entitled compound (33 mg) was obtained in the same manner as in Example 2 from 40 mg of (4-(2-thiophenehydroxyboryl)phenoxyethyl) (4-(2-thiophenehydroxyboryl)benzyl) ether and 11 mg of ethanolamine.

NMR (DMSO-$d_6$) 2.83 (m, 4H), 3.2 (m, 2H), 3.8 (m, 4H), 3.9 (m, 2H), 4.0 (m, 4H), 4.2 (m, 2H), 7.1-8.1 (m, 14H)

CCE: 10% inhibition at 1 μM

Example 54

(4-Trifluoromethylphenylhydroxyborylphenyl) (4'-trifluoromethylphenylhydroxyborylbenzyl) ether

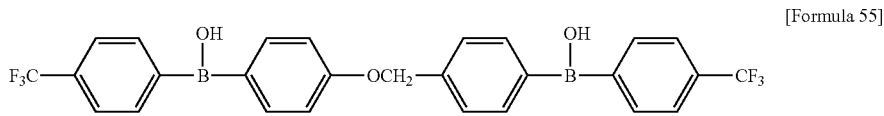

[Formula 55]

The entitled compound (48 mg) was obtained as a viscous liquid by the same method as in Example 1 using 342 mg of (4-bromophenyl) (4'-bromobenzyl) ether, 450 mg of 4-trifluoromethylphenyl bromide, 459 μL of triisoproxyborane and 1.36 mL of 1.47 M tert-BuLi as main raw materials.

$R_f$=0.67 (EtOAc, Hexane 1:1)

NMR (CDCl$_3$) 5.20 (s, 2H), 6.88-7.95 (m, 16H)

CCE: 100% inhibition at 3 μM, 60% inhibition at 1 μM

Example 55

(4-Trifluoromethylphenylaminoethoxyborylphenyl) (4'-trifluoromethylphenylaminoethoxyborylbenzyl) ether

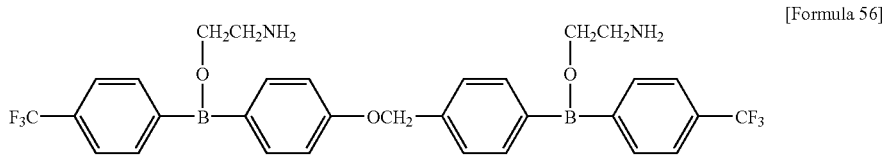

[Formula 56]

The entitled compound (20 mg) was obtained in the same manner as in Example 2 from 44 mg of (4-trifluoromethylphenylhydroxyborylphenyl) (4'-trifluoromethylphenylhydroxyborylbenzyl) ether and 13.7 mg of ethanolamine.

NMR (DMSO-$d_6$) 2.98 (m, 4H), 3.51 (m, 4H), 3.95 (m, 4H), 5.13 (s, 2H), 6.8-7.2 (16H)

CCE: 100% inhibition at 3 μM, 20% inhibition at 1 μM, 0% inhibition at 0.3 μM

Example 56

9,10-Bis-(trifluoromethylphenylhydroxyboryl)anthracene

[Formula 57]

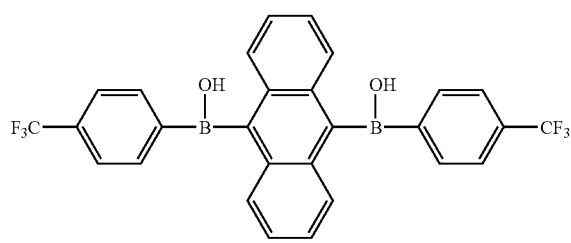

The entitled compound (82 mg) was obtained by the same method as in Example 3 using 337 mg of 9,10-dibromoanthracene, 341 mg of 4-trifluoromethylphenyl bromide and 459 μL of triisoproxyborane as main raw materials.

$R_f$=0.46 (EtOAc, Hexane 1:1)

Example 57

9,10-Bis-(trifluoromethylphenylaminoethoxyboryl)anthracene

[Formula 58]

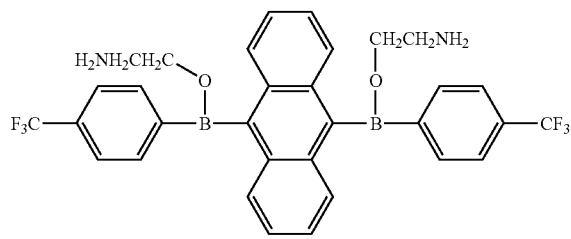

The entitled compound (15 mg) was obtained in the same manner as in Example 2 from 68 mg of 9,10-bis-(trifluoromethylphenylhydroxyboryl)anthracene and 26 mg of ethanolamine.

NMR (DMSO-$d_6$) 2.53 (m, 4H), 2.92 (m, 4H), 3.66 (m, 4H), 7.0-8.9 (m, 16H)

Example 58

Bis(3-(1-naphthylaminoethoxyboryl)benzyl) ether

[Formula 59]

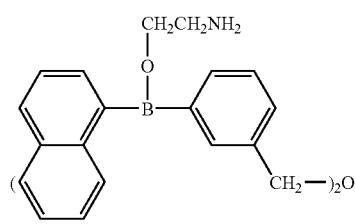

The entitled compound (13 mg) was obtained in the same manner as in Example 2 from 27 mg of bis(3-(1-naphthylhydroxyboryl)benzyl) ether and 6.5 mg of ethanolamine.

NMR (DMSO-$d_6$) 2.88 (m, 4H), 3.75 (m, 4H), 4.10 (m, 4H), 5.53 (s, 2H), 6.8-8.2 (m, 22H)

Example 59

4,5-Di(phenylhydroxyboryl)-2,7-di-t-butyl-9,9-dimethylxanthrene

[Formula 60]

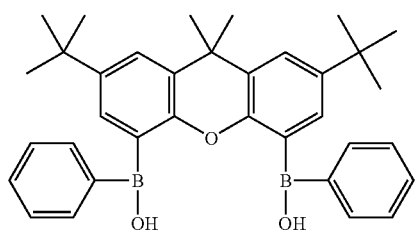

The entitled compound (211 mg) was obtained as a viscous liquid by the same method as in Example 3 using 480 mg of 4,5-dibromo-2,7-di-t-butyl-9,9-dimethylxanthrene, 341 mg of 4-bromotoluene and 459 μL of triisopropoxyborane as main raw materials.

$R_f$=0.67 (EtOAc, Hexane 1:1)

NMR (CDCl$_3$) 1.24 (s, 18H), 2.8 (s, 2H), 3.7 (s, 6H), 7.1-7.6 (m, 12H)

Example 60

4,5-Di(phenylaminoethoxyboryl)-2,7-di-t-butyl-9,9-dimethylxanthrene

[Formula 61]

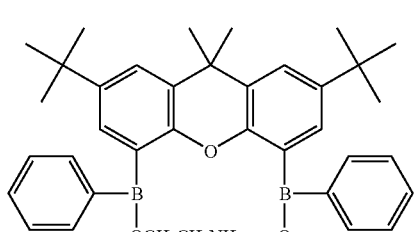

The entitled compound (13 mg) was obtained in the same manner as in Example 2 from 146 mg of 4,5-di(phenylhydroxyboryl)-2,7-di-t-butyl-9,9-dimethylxanthrene and 39 mg of ethanolamine.

NMR: unmeasurable due to insolubility in a solvent

CCE: 100% inhibition at 3 μM, 20% inhibition at 1 μM

Example 61

(4-(Phenylhydroxyboryl)phenoxyethyl) (4-(phenylhydroxyboryl)benzyl) ether

[Formula 62]

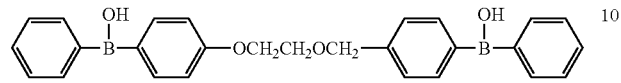

The entitled compound (23 mg) was obtained as a viscous liquid by the same method as in Example 1 using 193 mg of (4-bromophenoxyethyl) (4'-bromobenzyl) ether, 157 mg of 4-bromobenzene, 230 μL of triisoproxyborane and 0.68 mL of 1.47 M tert-butyllithium as main raw materials.

$R_f$=0.27 (EtOAc, Hexane 1:1)

NMR (CDCl$_3$) 3.78 (m, 2H), 4.17 (m, 2H), 4.63 (m, 2H), 7.4 (m, 18H)

Example 62

(4-(Phenylaminoethoxyboryl)phenoxyethyl) (4-(phenylaminoethoxyboryl)benzyl) ether

[Formula 63]

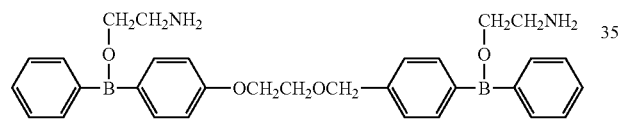

The entitled compound (4 mg) was obtained in the same manner as in Example 2 from 14 mg of (4-(phenylhydroxyboryl)phenoxyethyl) (4-(phenylhydroxyboryl)benzyl) ether and 5 mg of ethanolamine.

NMR (CDCl$_3$) 3.0 (m, 4H), 3.55 (m, 4H), 3.65 (m, 2H), 3.80 (m, 2H), 4.15 (m, 2H), 3.95 (m, 4H), 6.8-7.3 (m, 18H)

Example 63

6,6'-(Phenylhydroxyboryl)-2,2'-dipyridyl

[Formula 64]

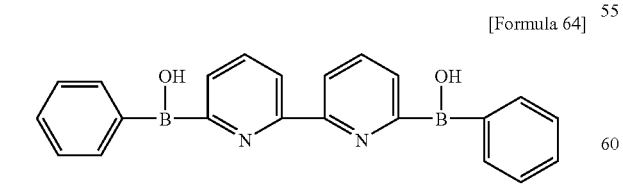

The entitled compound (207 mg) was obtained as a viscous liquid by the same method as in Example 1 using 314 mg of 6,6'-dibromo-2,2'-dipyridyl, 314 mg of bromobenzene and 459 μL of triisopropoxyborane as main raw materials.

$R_f$=0.37 (EtOAc, Hexane 1:1)

NMR (CDCl$_3$) 7.2-8.4 (m)

Example 64

6,6'-(Phenylaminoethoxyboryl)-2,2'-dipyridyl

[Formula 65]

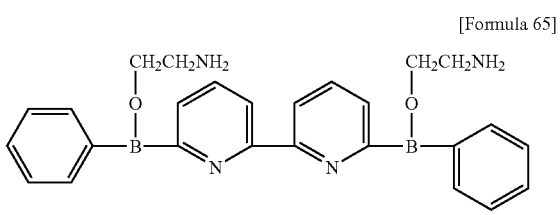

The entitled compound (84 mg) was obtained in the same manner as in Example 2 from 110 mg of 6,6'-(phenylhydroxyboryl)-2,2'-dipyridyl and 5 mg of ethanolamine.

NMR (DMSO-d$_6$) 2.84 (m, 4H), 3.75 (m, 4H), 4.03 (m, 4H), 6.8-7.3 (m, 18H)

Example 65

Bis(2,5-(phenylhydroxyboryl)furan

[Formula 66]

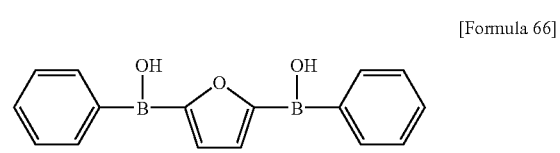

The entitled compound was obtained in the same manner as in Example 1 using 2,5-dibromofuran and bromobenzene as main raw materials.

NMR (CDCl$_3$) 7.3-7.6 (m), 8.0-8.3 (m)

Example 66

Bis(2,5-(phenylaminoethoxyboryl)furan

[Formula 67]

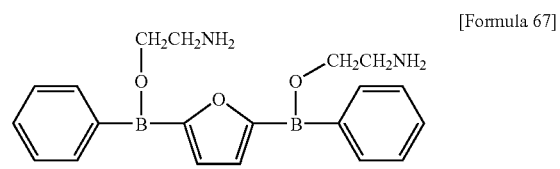

The entitled compound was obtained by allowing ethanolamine to act on bis(2,5-(phenylhydroxyboryl)furan).

NMR (DMSO-d$_6$) 2.8 (m, 4H), 4.1 (m, 4H), 6.3-7.8 (m, 12H)

Example 67

Bis(4,4'-(phenyl-N,N-dimethylaminoethoxyboryl)phenyl) ether

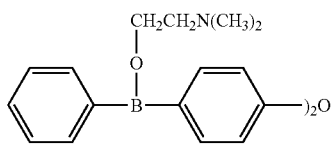

[Formula 68]

The entitled compound (60 mg) was obtained by allowing 50 mg of dimethylethanolamine to act on 95 mg of bis(4,4'-(phenylhydroxyboryl)phenyl) ether.

NMR (CDCl$_3$) 2.37 (s, 12H), 2.84 (m, 4H), 3.95 (m, 4H), 6.0-8.9 (m, 18H)

Example 68

Bis(4,4'-(phenyl-N-methylaminoethoxyboryl)phenyl) ether

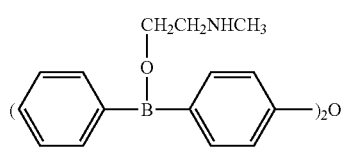

[Formula 69]

The entitled compound (32 mg) was obtained by allowing 52 mg of methylethanolamine to act on 133 mg of bis(4,4'-(phenylhydroxyboryl)phenyl) ether.

NMR (CDCl$_3$), 2.38 (s, 6H), 2.72 (m, 4H), 3.60 (m, 4H), 6.8-7.7 (m, 18H)

CCE: 80% inhibition at 1 μM, 20% inhibition at 0.3 μM

Example 69

Bis(4,4'-(phenyl-glycineboryl)phenyl) ether

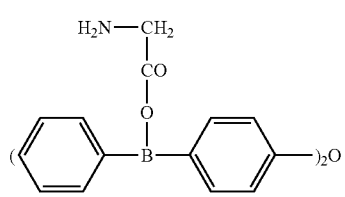

[Formula 70]

Bis(4,4'-(phenylhydroxyboryl)phenyl) ether (84 mg) and glycine (40 mg) were heated in 3 mL of ethanol at 60° C. for one hour to give 17 mg of the entitled compound.

NMR (DMSO-d$_6$), 3.43 (m, 4H), 7.0-8.0 (m, 18H)

Example 70

Bis(4,4'-(phenyl-glutamineboryl)phenyl) ether

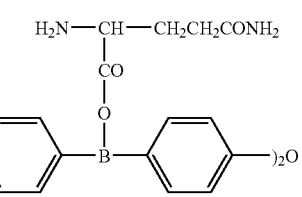

[Formula 71]

Bis(4,4'-(phenylhydroxyboryl)phenyl) ether (22 mg) and glutamine (19 mg) were heated in 2 mL of ethanol at 60° C. for one hour to give 8 mg of the entitled compound.

NMR (DMSO-d$_6$), 2.05 (m, 4H), 2.25 (m, 4H), 2.42 (m, 4H), 3.3 (m, 4H), 4.0 (m, 2H), 6.8-7.8 (m, 18H)

Example 71

Bis(4,4'-(phenyl-cysteineboryl)phenyl) ether

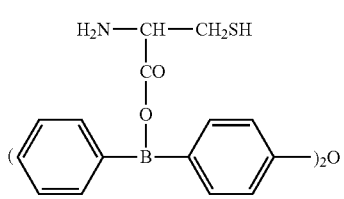

[Formula 72]

Bis(4,4'-(phenylhydroxyboryl)phenyl) ether (76 mg) and cysteine hydrochloride (70.6 mg) were heated in 3 mL of ethanol at 60° C. for one hour to give 33 mg of the entitled compound.

NMR (DMSO-d$_6$), 2.8-3.0 (m, 8H), 3.75 (m, 4H), 6.7-7.8 (m, 18H)

Example 72

Bis(4,4'-(phenyl-asparagineboryl)phenyl) ether

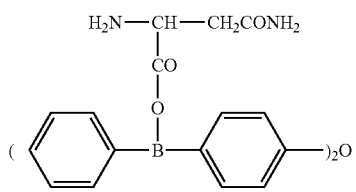

[Formula 73]

Bis(4,4'-(phenylhydroxyboryl)phenyl) ether (20 mg) and asparagine (14 mg) were heated in 3 mL of ethanol at 60° C. for one hour to give 7 mg of the entitled compound.

NMR (DMSO-$d_6$), 2.42 (m, 4H), 3.15 (m, 4H), 3.62 (m, 4H), 4.12 (m, 2H), 6.85 (m, 4H), 6.9-7.8 (m, 18H)

Example 73

(4-(Phenyl-N-methylaminoethylboryl)phenyl) (4'-(hydroxymethylphenyl-N-methylaminoethylboryl)phenyl) ether

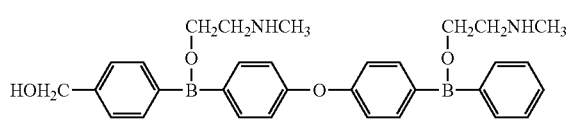

[Formula 74]

The entitled compound (15 mg) was obtained by allowing 10 mg of 4-(phenyl-hydroxyboryl)phenyl) (4'-(hydroxymethylphenyl-hydroxyboryl)phenyl) ether and 3.7 mg of N-methylethanolamine to act in 0.3 mL of ethanol.

NMR (CDCl$_3$), 2.45 (s, 12H), 2.78 (m, 4H), 3.67 (m, 4H), 3.75 (m, 2H), 6.8-7.5 (m, 17H)

Example 74

(4-(Phenyl-N,N-dimethylaminoethylboryl)phenyl) (4'-(hydroxymethylphenyl-N,N-dimethylaminoethylboryl)phenyl) ether

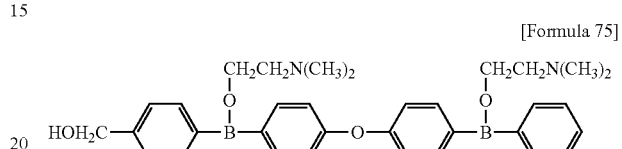

[Formula 75]

The entitled compound (17 mg) was obtained by allowing 19 mg of 4-(phenyl-hydroxyboryl)phenyl) (4'-(hydroxymethylphenyl-hydroxyboryl)phenyl) ether and 8.2 mg of N,N-dimethylethanolamine to act in 0.3 mL of ethanol.

NMR (CDCl$_3$), 2.5 (s, 12H), 2.82 (m, 4H), 4.11 (m, 4H), 4.6 (m, 2H), 7.0-7.8 (m, 17H)

Example 75

(4-(Phenyl-glutamic acid boryl)phenyl) (4'-(hydroxymethylphenyl-glutamic acid boryl)phenyl) ether

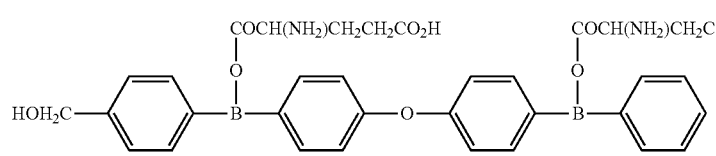

[Formula 76]

The entitled compound (23 mg) was obtained by allowing 27 mg of 4-(phenyl-hydroxyboryl)phenyl) (4'-(hydroxymethylphenyl-hydroxyboryl)phenyl) ether and 22.3 mg of sodium glutamate to act in 0.5 mL of ethanol.

NMR (DMSO-$d_6$) 2.0 (m, 4H), 2.35 (m, 4H), 4.65 (m, 4H), 5.23 (m, 4H), 6.7-7.7 (m, 17H)

Example 76

(4-(Phenyl-glutamineboryl)phenyl) (4'-(hydroxymethylphenyl-glutamineboryl)phenyl) ether

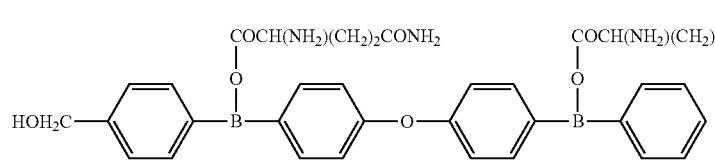

[Formula 77]

Bis(4,4'-(phenylhydroxyboryl)phenyl) ether (31 mg) and glutamine (22 mg) were heated in 3 mL of ethanol at 80° C. for three hours to give 32 mg of the entitled compound.

NMR (DMSO-$d_6$) 2.0 (m, 4H), 2.2 (m, 4H), 2.5 (m, 4H), 3.5 (m, 4H), 4.0 (m, 2H), 6.9-7.0 (m, 17H)

Example 77

Bis(4,4'-(phenyl-N,N-dimethylaminoethoxyboryl)benzyl) ether

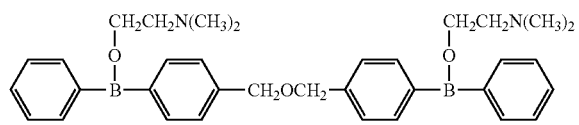

[Formula 78]

The entitled compound (60 mg) was obtained by allowing 95 mg of bis(4,4'-(phenylhydroxyboryl)benzyl) ether and 55 mg of N,N-dimethylethanolamine to act in 0.7 mL of ethanol at room temperature.

NMR (CDCl$_3$), 2.53 (s, 6H), 2.86 (m, 4H), 4.23 (m, 4H), 4.55 (s, 4H), 7.1-7.75 (m, 18H)

Example 78

Bis(4,4'-(phenyl-N-aminoethyl-aminoethoxyboryl)phenyl) ether

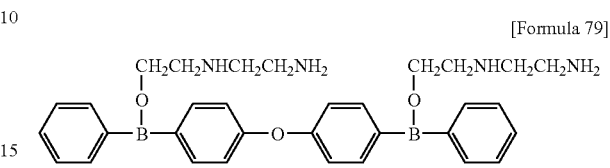

[Formula 79]

The entitled compound (26 mg) was obtained by allowing 33 mg of bis(4,4'-(phenylhydroxyboryl)phenyl) ether and 18 mg of aminoethylethanolamine to act in 0.6 mL of ethanol.

NMR (CDCl$_3$), 2.1 (m, 4H), 2.51 (m, 4H), 2.77 (m, 4H), 3.69 (m, 4H), 4.04 (m, 4H), 6.7-7.6 (m, 18H)

Example 79

(4-(Phenyl-cysteineboryl)phenyl) (4'-(hydroxymethylphenyl-cysteineboryl)phenyl) ether

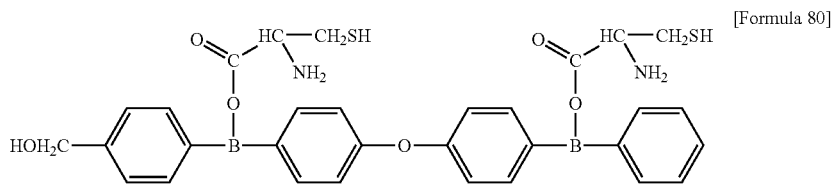

[Formula 80]

The entitled compound (10 mg) was obtained by allowing 31 mg of 4-(phenyl-hydroxyboryl)phenyl) (4'-(hydroxymethylphenyl-hydroxyboryl)phenyl) ether and 3.7 mg of cysteine to act in 0.6 mL of ethanol at 60° C. for one hour.

NMR (DMSO-$d_6$), 2.8-3.0 (m, 4H), 3.3-3.5 (m, 4H), 4.2 (m, 2H), 6.8-8.0 (m, 17H)

Example 80

Bis(4,4'-(phenoxyphenyl-aminoethoxyboryl)phenyl) ether

The entitled compound (5 mg) was obtained by allowing 38 mg of bis(4,4'-(phenoxyphenyl-hydroxyboryl)phenyl) ether and 6 mg of ethanolamine to act in 0.6 mL of ethanol.

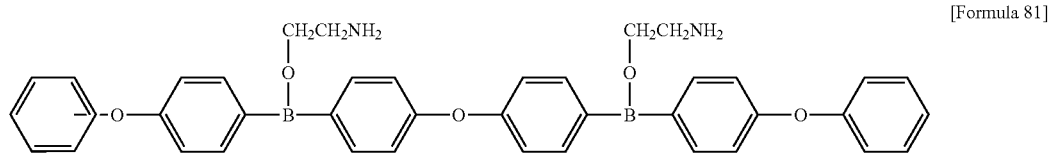

[Formula 81]

NMR (DMSO-d$_6$) 2.38 (m, 4H), 3.27 (m, 4H), 3.55 (m, 4H), 7.1-7.7 (m, 26H)

Example 81

Bis(4,4'-(phenyl-N-aminoethyl-aminoethoxyboryl)benzyl) ether

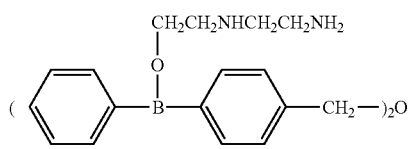

[Formula 82]

The entitled compound (28 mg) was obtained by allowing 29 mg of bis(4,4'-(phenylhydroxyboryl)benzyl) ether and 15 mg of aminoethylethanolamine to act in 0.7 mL of ethanol at room temperature.

NMR (CDCl$_3$), 2.7 (m, 8H), 3.6 (m, 4H), 3.8-4.0 (m, 8H), 4.45 (m, 4H), 7.0-8.1 (m, 18H)

Example 82

Bis(4,4'-(phenyl-N-methylaminoethoxyboryl)benzyl) ether

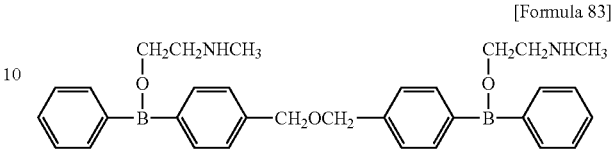

[Formula 83]

The entitled compound (8 mg) was obtained by allowing 20 mg of bis(4,4'-(phenylhydroxyboryl)benzyl) ether and 7.3 mg of N-methylaminoethanol to act in 0.7 mL of ethanol at room temperature.

NMR (CDCl$_3$), 2.20 (s, 6H), 2.77 (m, 4H), 3.85 (m, 4H), 4.50 (s, 4H), 7.2-7.7 (m, 18H)

Example 83

(4'-Trifluoromethylphenyl-N,N-dimethylaminoethoxyboryl)-4-phenyl (4'-trifluoromethylphenyl-N,N-dimethylaminoethoxyboryl)benzyl ether

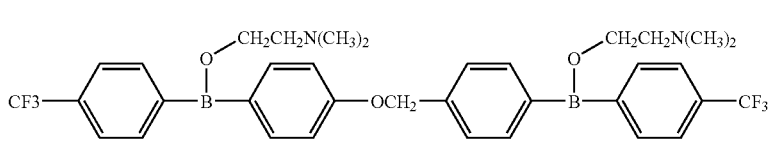

[Formula 84]

The entitled compound (7 mg) was obtained by allowing 19 mg of (4'-trifluoromethylphenyl-hydroxyboryl)-4-phenyl (4'-trifluoromethylphenyl-hydroxyboryl)-4-benzyl ether and 7 mg of N,N-dimethylethanolamine to act in 0.7 mL of ethanol at room temperature.

NMR (CDCl$_3$), 1.59 (m, 12H), 2.45 (m, 4H), 3.55 (m, 4H), 5.03 (m, 2H), 7.2-7.4 (m, 16H)

Example 84

(4'-Trifluoromethylphenyl-N-methylaminoethoxyboryl)-4-phenyl (4'-trifluoromethylphenyl-N-methylaminoethoxyboryl)-4-benzyl ether

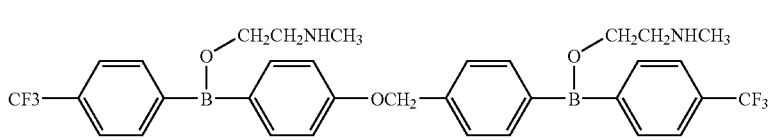

[Formula 85]

The entitled compound (9 mg) was obtained by allowing 19 mg of (4'-trifluoromethylphenyl-hydroxyboryl)-4-phenyl (4'-trifluoromethylphenyl-hydroxyboryl)-4-benzyl ether and 6 mg of N-methylethanolamine to act in 0.7 mL of ethanol at room temperature.

NMR (CDCl$_3$), 2.22 (s, 6H), 2.55 (m, 4H), 3.85 (m, 4H), 5.07 (s, 2H), 7.2-7.6 (m, 16H)

Capacitative calcium entry (CCE) inhibitory action of this compound
CCE: 100% inhibition at 3 μM, 50% inhibition at 1 μM Example 85

Bis(3,3'-(phenyl-N,N-dimethylaminoethoxyboryl)benzyl) ether

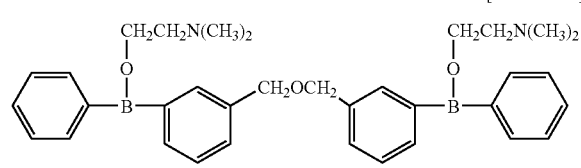
[Formula 86]

The entitled compound (10 mg) was obtained by allowing 25 mg of bis(3,3'-(phenylhydroxyboryl)benzyl) ether and 12 mg of N,N-dimethylethanolamine to act in 0.4 mL of ethanol.
NMR (CDCl$_3$), 2.35 (s, 6H), 2.72 (m, 4H), 4.05 (m, 4H), 4.51 (m, 4H)
CCE: 90% inhibition at 3 μM, 10% inhibition at 1 μM Example 86

Bis(3,3'-(phenyl-asparagineboryl)benzyl) ether

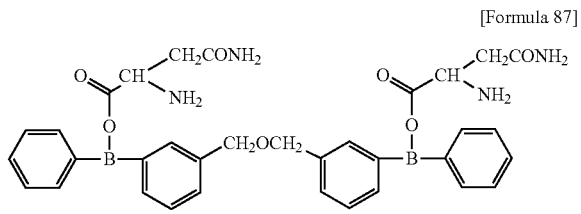
[Formula 87]

The entitled compound (9 mg) was obtained by allowing 44 mg of bis(3,3'-(phenylhydroxyboryl)benzyl) ether and 29 mg of asparagine to act in 0.5 mL of ethanol at 75° C.
NMR (CDCl$_3$), 1.8 (m, 4H), 2.3 (m, 4H), 2.92 (m, 4H), 3.45 (m, 2H), 4.5 (m, 4H), 7.3-7.8 (m, 18H)

Example 87

Bis(3,3'-(phenyl-aminothioethoxyboryl)benzyl) ether

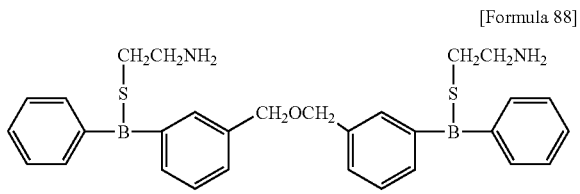
[Formula 88]

The entitled compound (15 mg) was obtained by allowing 45 mg of bis(3,3'-(phenylhydroxyboryl)benzyl) ether and 18 mg of aminoethanethiol to act in 0.3 mL of ethanol.

NMR (CDCl$_3$), 1.95 (m, 4H), 2.75 (m, 4H), 2.95 (m, 4H), 4.5 (m, 4H), 7.2-7.7 (m, 18H)

Example 88

Bis(4,4'-(phenyl-2-pyridylmethoxyboryl)benzyl) ether

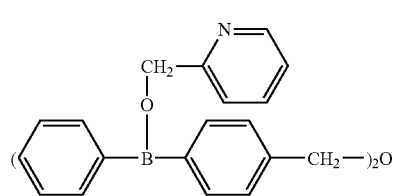
[Formula 89]

The entitled compound (34 mg) was obtained by allowing 59 mg of bis(4,4'-(phenylhydroxyboryl)benzyl) ether and 59 mg of 2-hydroxymethylpyridine to act in 0.7 mL of ethanol at room temperature.
NMR (CDCl$_3$), 4.50 (s, 4H), 5.31 (s, 4H), 7.2-8.4 (m, 26H)
Capacitative calcium entry (CCE) inhibitory action of this compound
CCE: 100% inhibition at 3 μM, 95% inhibition at 1 μM Example 89

Bis(4,4'-(p-trifluoromethylphenyl-hydroxyboryl)benzyl) ether

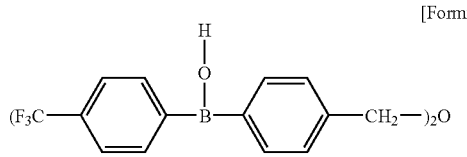
[Formula 90]

The entitled compound was obtained in the same manner as in Example 1 using trifluoromethyl-4-bromobenzene and bis(4,4-bromobenzyl) ether as main raw materials.
NMR (CDCl$_3$), 4.5 (m, 4H), 7.2-8.3 (m, 16H)

Example 90

Bis(4,4'-(3-chloro-4-methylphenyl-hydroxyboryl)benzyl) ether

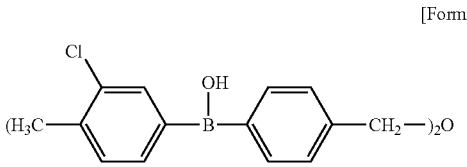
[Formula 91]

The entitled compound was obtained in the same manner as in Example 1 using 2-chloro-4-bromotoluene and bis(4,4-bromobenzyl) ether as main raw materials.
NMR (CDCl$_3$), 2.30 (s, 6H), 4.60 (m, 4H), 7.1-8.2 (m, 14H)
CCE: 100% inhibition at 3 μM, 20% inhibition at 1 μM

Example 91

Bis(4,4'-(phenyl-lysineboryl)benzyl) ether

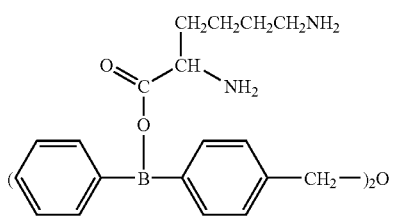

[Formula 92]

The entitled compound (25 mg) was obtained by allowing 97 mg of bis(4,4'-(phenylhydroxyboryl)benzyl) ether and 98 mg of lysine hydrochloride to act in 0.7 mL of ethanol at 90° C. for one hour.

NMR (CDCl$_3$), 1.22 (m, 8H), 2.80 (m, 4H), 3.55 (m, 4H), 4.11 (m, 2H), 4.55 (m, 18H)

Example 92

Bis(4,4'-(p-methoxymethyl-phenyl-hydroxyboryl)benzyl) ether

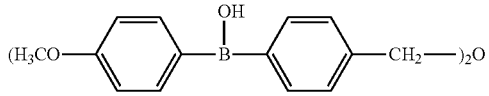

[Formula 93]

The entitled compound was obtained in the same manner as in Example 1 using 4-methoxy-bromobenzene and bis(4,4-bromobenzyl) ether as main raw materials.

NMR (CDCl$_3$), 3.82 (m, 6H), 4.67 (m, 4H), 6.9-7.6 (m, 16H)

Example 93

Bis(4,4'-(3,4-difluorophenyl-hydroxyboryl)benzyl) ether

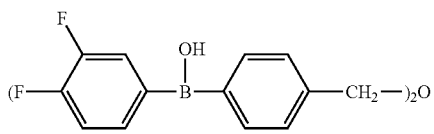

[Formula 94]

The entitled compound was obtained in the same manner as in Example 1 using 3,4-difluorobromobenzene and bis(4,4-bromobenzyl) ether as main raw materials.

NMR (CDCl$_3$), 4.59 (m, 4H), 6.8-7.8 (m, 14H)

Example 94

Bis(4,4'-(p-methoxyphenyl-aminoethoxyboryl)benzyl) ether

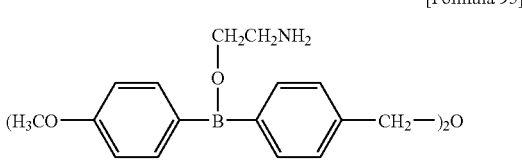

[Formula 95]

The entitled compound (20 mg) was obtained by allowing 56 mg of bis(4,4'-(p-methoxymethyl-phenyl-hydroxyboryl)benzyl) ether and 16 mg of aminoethanol to act in 0.7 mL of ethanol at room temperature for three hours.

NMR (CDCl$_3$) 1.97 (M, 4H), 2.77 (M, 4H), 3.77 (M, 6H), 4.46 (M, 4H), 6.7-7.4 (M, 16H)

Capacitative calcium entry (CCE) inhibitory action of this compound

CCE: 100% inhibition at 3 μM, 0% inhibition at 1 μM

Example 95

Bis(4,4'-(p-methoxyphenyl-N-methylaminoethoxyboryl)benzyl) ether

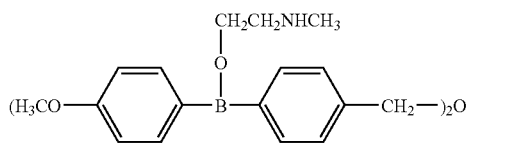

[Formula 96]

The entitled compound (16 mg) was obtained by allowing 56 mg of bis(4,4'-(p-methoxymethyl-phenyl-hydroxyboryl)benzyl) ether and 21 mg of N-methylaminoethanol to act in 0.7 mL of ethanol at room temperature for three hours.

NMR (CDCl$_3$), 2.45 (s, 6H), 2.80 (m, 4H), 3.80 (s, 6H), 4.11 (m, 4H), 4.49 (m, 4H), 6.9-7.7 (m, 16H)

Capacitative calcium entry (CCE) inhibitory action of this compound

CCE: 80% inhibition at 3 μM, 80% inhibition at 1 μM

Example 96

Bis(4,4'-(p-methoxyphenyl-N,N-dimethylaminoethoxyboryl)benzyl) ether

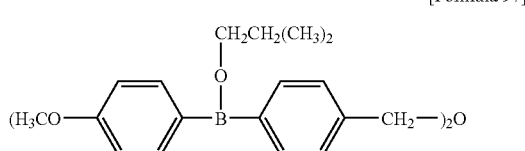

[Formula 97]

The entitled compound (51 mg) was obtained by allowing 22 mg of N,N-dimethylethanolamine to act on 85 mg of bis(4,4'-(p-methoxyphenyl-hydroxyboryl)benzyl) ether in 0.5 mL of ethanol.

NMR (CDCl₃), 2.54 (s, 12H), 2.80 (m, 4H), 3.75 (m, 6H), 4.17 (m, 4H), 4.58 (m, 4H), 6.8-7.7 (m, 16H)

Example 97

Bis(4,4'-(p-methoxyphenyl-2,4-diaminobutyric acid boryl)benzyl) ether

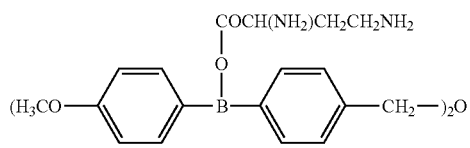

[Formula 98]

The entitled compound (15 mg) was obtained by allowing 29 mg of 2,4-diaminobutyric acid hydrochloride to act on 85 mg of bis(4,4'-(p-methoxyphenyl-hydroxyboryl)benzyl) ether in 0.5 mL of ethanol.

NMR (CDCl₃), 1.42 (m, 2H), 3.50 (m, 2H), 3.85 (m, 4H), 4.59 (m, 4H), 6.8-7.6 (m, 16H)

Example 98

Bis(4,4'-(3,4-difluorophenyl-aminoethoxyboryl)benzyl) ether

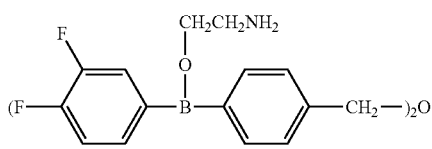

[Formula 99]

The entitled compound (15 mg) was obtained by allowing 14 mg of ethanolamine to act on 85 mg of bis(4,4'-(3,4-difluorophenyl-hydroxyboryl)benzyl) ether in 0.5 mL of ethanol.

NMR (CDCl₃), 2.93 (m, 4H), 4.45 (m, 4H), 6.8-7.6 (m, 14H)

Example 99

Bis(4,4'-(3,4-difluorophenyl-N-methylaminoethoxyboryl)benzyl) ether

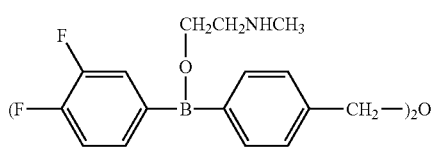

[Formula 100]

The entitled compound (18 mg) was obtained by allowing 17 mg of methylethanolamine to act on 85 mg of bis(4,4'-(3,4-difluorophenyl-hydroxyboryl)benzyl) ether in 0.6 mL of ethanol.

NMR (CDCl₃), 2.29 (s, 6H), 2.89 (m, 4H), 3.87 (m, 4H), 4.45 (m, 4H), 6.9-7.7 (m, 14H)

Example 100

Bis(4,4'-(3,4-difluorophenyl-N,N-dimethylaminoethoxyboryl)benzyl) ether

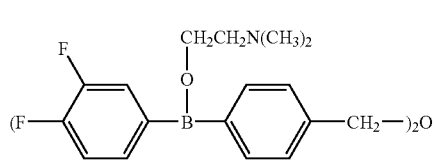

[Formula 101]

The entitled compound (15 mg) was obtained by allowing 20 mg of dimethylethanolamine to act on 49 mg of bis(4,4'-(3,4-difluorophenyl-hydroxyboryl)benzyl) ether in 0.6 mL of ethanol.

NMR (CDCl₃), 2.41 (s, 6H), 2.80 (m, 4H), 3.91 (m, 4H), 4.54 (m, 4H), 7.0-7.6 (m, 14H)

Example 101

Bis(4,4'-(3,4-difluorophenyl-N-aminoethylaminoethoxyboryl)benzyl) ether

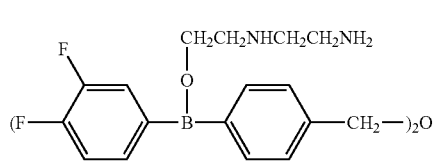

[Formula 102]

The entitled compound (17 mg) was obtained by allowing 25 mg of aminoethylethanolamine to act on 49 mg of bis(4,4'-(3,4-difluorophenyl-hydroxyboryl)benzyl) ether in 0.6 mL of ethanol.

NMR (CDCl₃), 2.62 (m, 4H), 2.75 (m, 4H), 3.02 (m, 4H), 3.80 (m, 4H), 4.55 (m, 4H), 6.9-7.6 (m, 14H)

Example 102

Bis(4,4'-(3-chloro-4-methylphenyl-aminoethoxyboryl)benzyl) ether

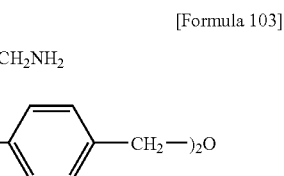

[Formula 103]

The entitled compound (5 mg) was obtained by allowing 22 mg of N,N-dimethylethanolamine to act on 99 mg of bis(4,4'-(3-chloro-4-methylphenyl-hydroxyboryl)benzyl) ether bis(4,4'-(3-chloro-4-methylphenyl-hydroxyboryl)benzyl) ether in 0.5 mL of ethanol.

NMR (CDCl₃), 2.08 (m, 6H), 2.89 (m, 4H), 2.65 (m, 4H), 4.50 (m, 4H), 7.0-7.5 (m, 6H)

Capacitative calcium entry (CCE) inhibitory action of this compound
CCE: 100% inhibition at 3 μM, 30% inhibition at 1 μM

Example 103

Bis(4,4'-(3-chloro-4-methylphenyl-N-methylamino-ethoxyboryl)benzyl) ether

[Formula 104]

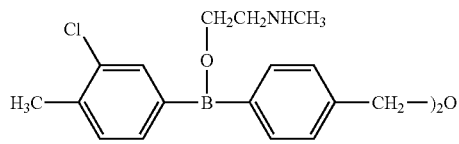

The entitled compound (31 mg) was obtained by allowing 32 mg of N-methylethanolamine to act on 99 mg of bis(4,4'-(3-chloro-4-methylphenyl-hydroxyboryl)benzyl) ether in 0.5 mL of ethanol.
NMR (CDCl$_3$), 2.16 (s, 6H), 2.30 (s, 6H), 2.70 (m, m, 4H), 3.80 (m, 4H), 4.45 (m, 4H), 7.0-7.6 (m, 14H)
CCE: 80% inhibition at 3 μM, 30% inhibition at 1 μM

Example 104

Bis(4,4'-(3-chloro-4-methylphenyl-N,N-dimethylaminoethoxyboryl)benzyl) ether

[Formula 105]

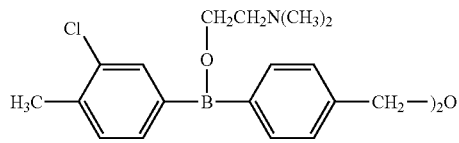

The entitled compound (5 mg) was obtained by allowing 22 mg of N,N-dimethylethanolamine to act on 99 mg of bis(4,4'-(3-chloro-4-methylphenyl-hydroxyboryl)benzyl) ether in 0.5 mL of ethanol.
NMR (CDCl$_3$), 2.3 (m, 6H), 2.54 (m, 6H), 2.86 (m, 4H), 4.18 (m, 4H), 4.49 (m, 4H), 7.0-7.7 (m, 14H)
CCE: 100% inhibition at 3 μM, 20% inhibition at 1 μM

Example 105

Bis(4,4'-(3-chloro-4-methylphenyl-2-piperidylmethyloxyboryl)benzyl) ether

[Formula 106]

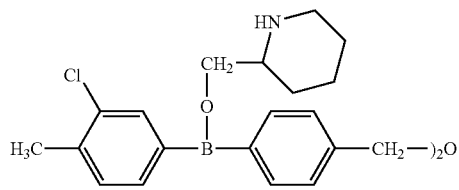

The entitled compound (88 mg) was obtained by allowing 52 mg of 2-hydroxymethylpiperidine to act on 99 mg of bis(4,4'-(3-chloro-4-methylphenyl-hydroxyboryl)benzyl) ether in 1 mL of ethanol.
NMR (CDCl$_3$), 1.25 (m, 4H), 1.59 (m, 4H), 1.80 (m, 4H), 1.30 (m, 6H), 3.00 (m, 4H), 3.50 (m, 2H), 3.65 (m, 4H), 7.0-7.6 (m, 14H)
CCE: 100% inhibition at 3 μM, 30% inhibition at 1 μM

Example 106

Bis(4,4'-(p-trifluoromethylphenyl-N,N-dimethylaminoethoxyboryl)benzyl) ether

[Formula 107]

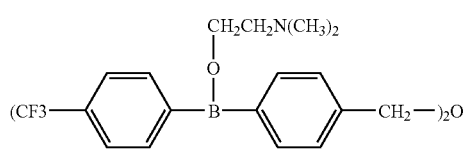

The entitled compound (39 mg) was obtained by allowing 85 mg of bis(4,4'-(p-trifluororomethylphenyl-hydroxyboryl)benzyl) ether and 31 mg of N,N-dimethylethanolamine to act in 0.7 mL of ethanol.
NMR (CDCl$_3$), 2.47 (m, 6H), 2.85 (m, 4H), 4.10 (m, 4H), 4.50 (m, 4H), 7.1-7.8 (m, m, 16H)
CCE: 100% inhibition at 3 μM, 30% inhibition at 1 μM

Example 107

Bis(4,4'-(p-trifluoromethylphenyl-asparagineboryl) benzyl) ether

[Formula 108]

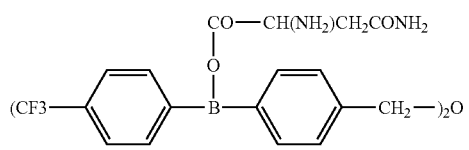

The entitled compound (8 mg) was obtained by allowing 85 mg of bis(4,4'-(p-trifluororomethyl-phenyl-hydroxyboryl)benzyl) ether and 48 mg of asparagine to act in 0.7 mL of ethanol.
NMR (DMSO-d$_6$), 2.3- (m, 4H), 2.8-3.6 (m, 10H), 4.3 (m, 4H), 6.8-7.7 (m, 16H)

Example 108

Bis(4,4'-(p-trifluoromethylphenyl-aminoethoxyboryl)benzyl) ether

[Formula 109]

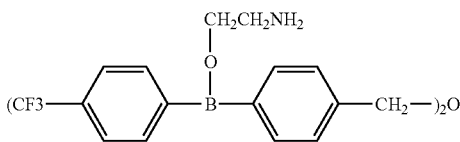

The entitled compound (28 mg) was obtained by allowing 92 mg of bis(4,4'-(p-trifluoromethylphenyl-hydroxyboryl)benzyl) ether and 23 mg of ethanolamine to act in 0.7 mL of ethanol.

NMR (CDCl$_3$), 2.31 (m, 4H), 2.91 (m, 4H), 3.67 (m, 4H), 4.52 (m, 4H), 7.1-7.7 (m, 16H)

CCE: 100% inhibition at 3 μM, 20% inhibition at 1 μM

Example 109

(4-Phenyl-N-methylaminoethoxyborylphenyl) 4'-(N-methylaminoethoxyborylbenzyl) ether

[Formula 110]

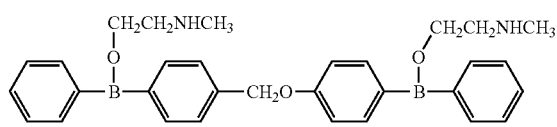

The entitled compound (68 mg) was obtained in the same manner as in Example 3 from 57 mg of (4-phenylhydroxyborylphenyl) (4'-phenylhydroxyborylbenzyl) ether and 23 mg of N-methylethanolamine.

NMR (CDCl$_3$), 2.06 (m, 6H), 2.65 (m, 4H), 3.68 (m, 4H), 5.01 (m, 2H), 6.8-7.6 (m, 18H)

CCE: 100% inhibition at 3 μM, 80% inhibition at 1 μM

Example 110

(4-Phenyl-N,N-dimethylaminoethoxyborylphenyl) 4'-(N,N-dimethylaminoethoxyborylbenzyl) ether

[Formula 111]

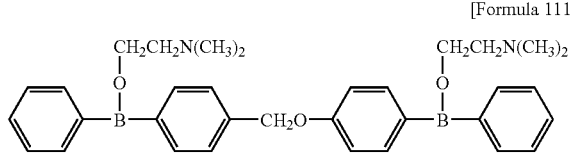

The entitled compound (80 mg) was obtained in the same manner as in Example 3 from 57 mg of (4-phenylhydroxyborylphenyl) (4'-phenylhydroxyborylbenzyl) ether and 26 mg of N,N-dimethylethanolamine.

NMR (CDCl$_3$), 2.45 (m, 12H), 2.79 (m, 4H), 4.10 (m, 4H), 5.03 (m, 2H), 6.8-7.8 (m, 18H)

CCE: 100% inhibition at 3 μM, 20% inhibition at 1 μM

Example 111

(4-Phenyl-2-pyridylmethoxyborylphenyl) (4'-phenyl-2-pyridylmethoxyborylbenzyl) ether

[Formula 112]

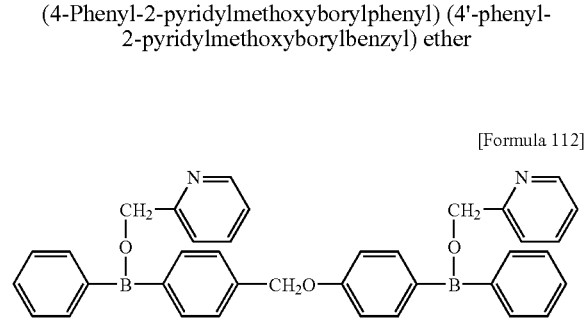

The entitled compound (48 mg) was obtained in the same manner as in Example 3 from 57 mg of (4-phenylhydroxyborylphenyl) (4'-phenylhydroxyborylbenzyl) ether and 33 mg of hydroxymethylpyridine.

NMR (CDCl$_3$), 5.03 (m, 2H), 5.28 (m, 4H), 6.9-8.3 (m, 26H)

CCE: 100% inhibition at 3 μM, 20% inhibition at 1 μM

Example 112

4-(Phenyl-p-methoxyphenyl-2-pyridylmethoxyboryl)-phenyl 4'-(p-methoxyphenyl-2-pyridylmethoxyboryl)benzyl ether

[Formula 113]

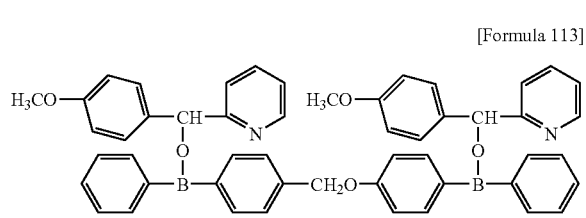

The entitled compound (89 mg) was obtained in the same manner as in Example 3 from 57 mg of (4-phenylhydroxyborylphenyl) (4'-phenylhydroxyborylbenzyl) ether and 63 mg of 1-(4-methoxyphenyl)-1-(2-pyridyl)methanol.

NMR (CDCl$_3$), 3.81 (m, 6H), 5.02 (m, 2H), 6.07 (m, 4H), 6.9-7.8 (m, 36H)

Example 113

Bis(4,4'-(phenyl-3-piperidyloxyboryl)phenyl) ether

[Formula 114]

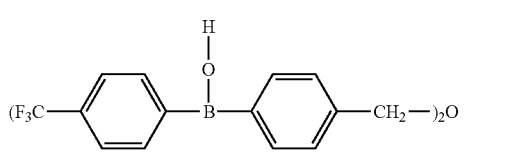

The entitled compound was obtained in the same manner as in Example 1 using trifluoromethyl-bromobenzene and bis(4,4'-bromobenzyl) ether as main raw materials.

NMR (CDCl$_3$), 4.42 (m, 4H), 7.0-8.1 (m, 16H)

Example 114

Bis(4,4'-(phenyl-2-pyridylmethoxyboryl)phenyl) ether

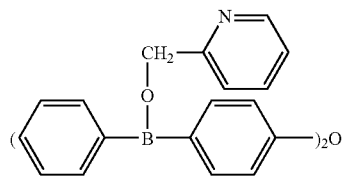

[Formula 115]

The entitled compound (38 mg) was obtained by allowing 42 mg of bis(4,4'-(phenylhydroxyboryl)phenyl) ether and 20 mg of 2-hydroxymethylpyridine to act in 0.25 mL of ethanol.

NMR (CDCl$_3$), 5.28 (s, 4H), 6.8-8.4 (m, 26H)

Example 115

Bis(4,4'-(phenyl-aminothioethoxyboryl)phenyl) ether

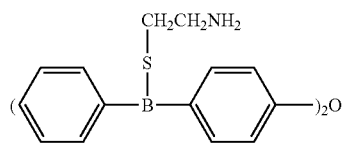

[Formula 116]

The entitled compound (36 mg) was obtained by allowing 42 mg of bis(4,4'-(phenylhydroxyboryl)phenyl) ether and 18 mg of 2-aminoethanethiol to act in 0.5 mL of ethanol.

NMR (CDCl$_3$), 2.67 (m, 4H), 2.91 (m, 4H), 3.30, 6.9-7.6 (m, 18H)

Example 116

Bis(4,4'-(phenyl-2-amino-1-phenylethoxyboryl)phenyl) ether

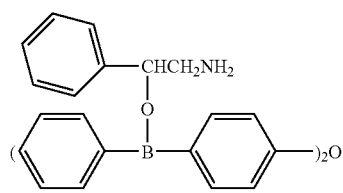

[Formula 117]

The entitled compound (41 mg) was obtained by allowing 42 mg of bis(4,4'-(phenylhydroxyboryl)phenyl) ether and 30 mg of 2-aminophenylethanol to act in 0.5 mL of ethanol.

NMR (CDCl$_3$), 2.85 (m, 4H), 3.35 (m, 4H), 5.10 (m, 2H), 6.9-7.7 (m, 18H)

Example 117

Bis(4,4'-(phenyl-ornithineboryl)phenyl) ether

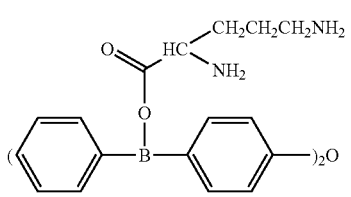

[Formula 118]

The entitled compound (44 mg) was obtained by allowing 37 mg of bis(4,4'-(phenylhydroxyboryl)phenyl) ether and 35 mg of 2,4-diaminobutyric acid hydrochloride to act in 0.5 mL of ethanol.

NMR (DMSO-d$_6$), 1.20 (m, 4H), 2.50 (m, 2H), 3.20 (m, 4H), 6.7-7.8 (m, 18H)

CCE: 100% inhibition at 3 μM, 80% inhibition at 1 μM

Example 118

Bis(4,4'-(phenyl-2,3-diaminopropionic acid boryl)phenyl) ether

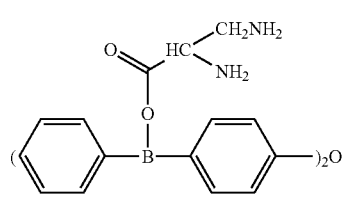

[Formula 119]

The entitled compound (32 mg) was obtained by allowing 37 mg of bis(4,4'-(phenylhydroxyboryl)phenyl) ether and 26 mg of 2,4-diaminopropionic acid hydrochloride to act in 0.5 mL of ethanol.

NMR (DMSO-d$_6$), 2.3-2.4 (m, 4H), 2.7-3.0 (m, 10H), 6.7-7.4 (m, 18H)

Example 119

Bis(4,4'-(phenyl-lysineboryl)phenyl) ether

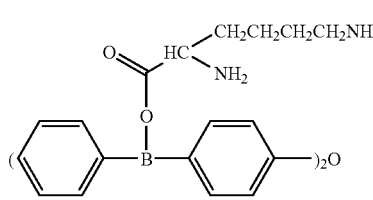

[Formula 120]

The entitled compound (25 mg) was obtained by allowing 37 mg of bis(4,4'-(phenylhydroxyboryl)phenyl) ether and 35 mg of lysine hydrochloride to act in 0.25 mL of ethanol.

NMR (DMSO-d$_6$), 0.80 (m, 4H), 1.10 (m, 4H), 1.60 (m, 4H), 2.2 (m, 8H), 2.70 (m, 4H), 6.8-7.2 (m, 18H)

Example 120

Bis(4,4'-(phenyl-2-pyrrolidinemethoxyboryl)phenyl) ether

[Formula 121]

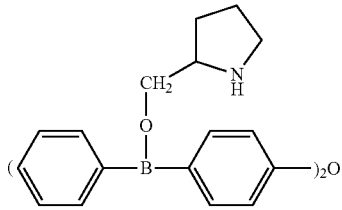

The entitled compound (38 mg) was obtained by allowing 37 mg of bis(4,4'-(phenylhydroxyboryl)phenyl) ether and 19 mg of 2-pyrrolidinemethanol to act in 0.25 mL of ethanol.

NMR (CDCl$_3$), 1.6 (m, 4H), 2.0 (m, 4H), 2.8 (m, 4H), 3.5-3.8 (m, 4H), 6.8-7.6 (m, 18H)

Example 121

Bis(4,4'-(naphthylhydroxyboryl)phenyl) ether

[Formula 122]

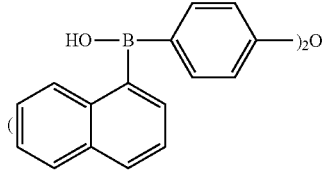

The entitled compound was obtained in the same manner as in Example 1 using 1-bromonaphthalene and bis(4,4'-bromophenyl) ether as main raw materials.

NMR (CDCl$_3$), 6.0-7.8 (m, 22H)

Example 122

Bis(4,4'-(tolylhydroxyboryl)phenyl) ether

[Formula 123]

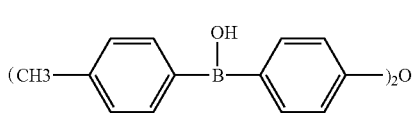

The entitled compound was obtained in the same manner as in Example 1 using 4-bromotoluene and bis(4,4'-bromophenyl) ether as main raw materials NMR (CDCl$_3$), 1.37 (s, 6H), 6.9-7.9 (m, 16H).

Example 123

Bis(4,4'-(naphthyl-aminoethoxyboryl)phenyl) ether

[Formula 124]

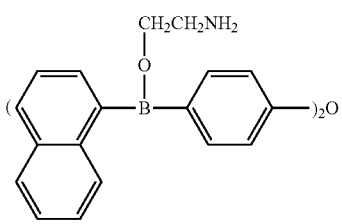

The entitled compound (81 mg) was obtained by allowing 86 mg of bis(4,4'-(naphthyl-hydroxyboryl)phenyl) ether and 22 mg of ethanolamine to act in 0.25 mL of ethanol.

NMR (CDCl$_3$), 2.72 (m, 4H), 2.99 (m, 4H), 3.83 (m, 4H), 6.7-7.5 (m, 22H)

Example 124

Bis(4,4'-(naphthyldimethylaminoethoxyboryl)phenyl) ether

[Formula 125]

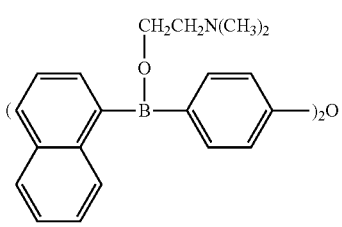

The entitled compound (32 mg) was obtained by allowing 86 mg of bis(4,4'-(naphthyl-hydroxyboryl)phenyl) ether and 31 mg of dimethylethanolamine to act in 0.25 mL of ethanol.

NMR (CDCl$_3$), 2.35 (m, 12H), 2.73 (m, 4H), 2.87 (m, 4H), 7.65-7.8 (m, 22H)

Example 125

Bis(4,4'-(naphthyl-2-pyridylmethoxyboryl)phenyl) ether

[Formula 126]

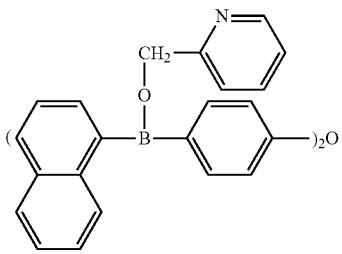

The entitled compound (39 mg) was obtained by allowing 86 mg of bis(4,4'-(naphthyl-hydroxyboryl)phenyl) ether and 39 mg of 2-hydroxypyridine to act in 0.6 mL of ethanol.
NMR (CDCl$_3$), 5.21 (s, 4H), 6.8-7.50 (m, 22H)

Example 126

Bis(4,4'-(naphthylglutamineboryl)phenyl) ther

[Formula 127]

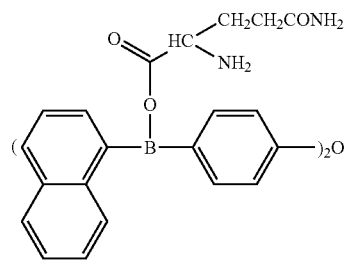

The entitled compound (46 mg) was obtained by allowing 86 mg of bis(4,4'-(naphthyl-hydroxyboryl)phenyl) ether and 52 mg of glutamine to act in 0.6 mL of ethanol.
NMR (DMSO-d$_6$), 2.20 (m, 4H), 3.4 (m, 8H), 4.35 (m, 2H), 6.7-7.8 (m, 24H)

Example 127

Bis(4,4'-(naphthyl-2,4-diaminopropionic acid boryl)phenyl) ether

[Formula 128]

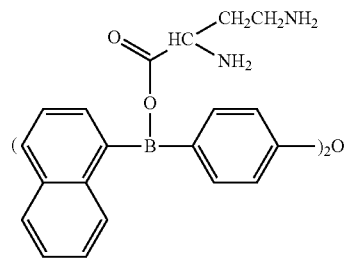

The entitled compound (81 mg) was obtained by allowing 86 mg of bis(4,4'-(naphthyl-hydroxyboryl)phenyl) ether and 22 mg of ethanolamine to act in 0.25 mL of ethanol.
NMR (DMSO-d$_6$), 1.74 (m, 4H), 2.45 (m, 4H), 3.6-3.8 (m, 8H), 7.3-7.8 (m, 22H)

Example 128

Bis(4,4'-(tolyldimethylaminoethoxyboryl)phenyl) ether

[Formula 129]

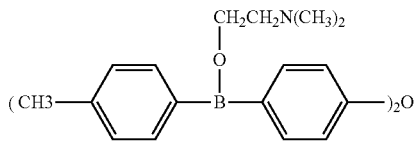

The entitled compound (39 mg) was obtained by allowing 82 mg of 4,4'-(4-methylphenylhydroxyboryl)diphenyl ether and 35 mg of N,N-dimethylaminoethanol to act in 0.25 mL of ethanol.
NMR (CDCl$_3$), 1.94 (m, 4H), 2.39 (s, 6H), 3.79 (m, 4H), 6.8-7.9 (m, 16H)

Example 129

Bis(4,4'-(tolylpiperazylethoxyboryl)phenyl) ether

[Formula 130]

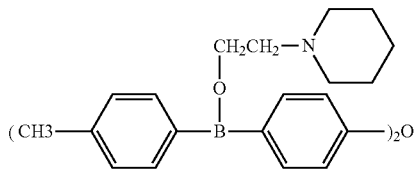

The entitled compound (71 mg) was obtained by allowing 81 mg of 4,4'-(4-methylphenylhydroxyboryl)diphenyl ether and 53 mg of piperazineethanol to act in 0.6 mL of ethanol.
NMR (CDCl$_3$), 2.51 (m, 12H), 2.89 (m, 6H), 3.38 (m, 12H), 3.67 (m, 4H), 6.8-7.9 (m, 16H)

Example 130

Bis(4,4'-(tolylglutamineboryl)phenyl) ether

[Formula 131]

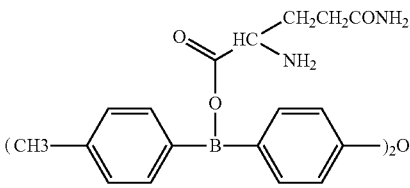

The entitled compound (37 mg) was obtained by allowing 82 mg of 4,4'-(4-methylphenylhydroxyboryl)diphenyl ether and 81 mg of asparagine to act in 0.6 mL of ethanol.

NMR (DMSO-$d_6$), 2.50 (s, 6H), 2.73 (m, 4H), 3.5-3.7 (m, 4H), 6.9-7.8 (m, 16H)

Example 131

Bis(4,4'-(tolyllysineboryl)phenyl) ether

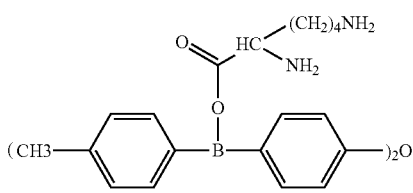
[Formula 132]

The entitled compound (76 mg) was obtained by allowing 82 mg of 4,4'-(4-methylphenylhydroxyboryl)diphenyl ether and 73 mg of lysine to act in 0.6 mL of ethanol.

Example 132

Bis(4,4'-(phenyl-2-amino-1-phenylethoxyboryl)benzyl) ether

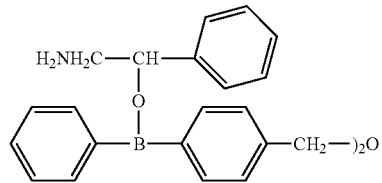
[Formula 133]

The entitled compound (52 mg) was obtained by allowing 26.5 mg of bis(4,4'-(phenylhydroxyboryl)benzyl) ether and 26.5 mg of 2-aminophenylethanol to act in 0.6 mL of ethanol.

NMR (CDCl$_3$), 2.10 (m, 4H), 2.85 (m, 2H), 4.53 (m, 4H), 7.1-7.4 (m, 28H)

Example 133

Bis(4,4'-(phenyl-aminothioethoxyboryl)benzyl) ether

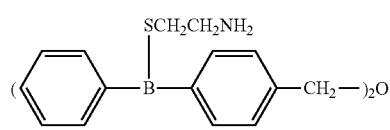
[Formula 134]

The entitled compound (32 mg) was obtained by allowing 23.5 mg of bis(4,4'-(phenylhydroxyboryl)benzyl) ether and 8.93 mg of 2-aminoethanethiol to act in 3 mL of ethanol.

NMR (CDCl$_3$), 2.74 (m, 4H), 3.64 (m, 8H), 4.51 (m, 4H), 7.01-7.55 (m, 18H)

Example 134

Bis(4,4'-(phenyl-2-pyrrolidinemethoxyboryl)benzyl) ether

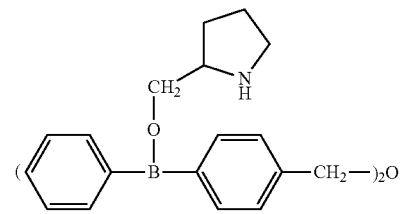
[Formula 135]

The entitled compound (35 mg) was obtained by allowing 23.5 mg of bis(4,4'-(phenylhydroxyboryl)benzyl) ether and 14 mg of 2-pyrrolidinemethanol to act in 1 mL of ethanol.

NMR (CDCl$_3$), 1.50 (m, 8H), 2.65 (m, 6H), 4.49 (m, 4H), 7.15-7.42 (m, 18H)

CCE: 100% inhibition at 3 μM, 20% inhibition at 1 μM

Example 135

Bis(4,4'-(phenyl-2,4-diaminobutyric acid boryl)benzyl) ether

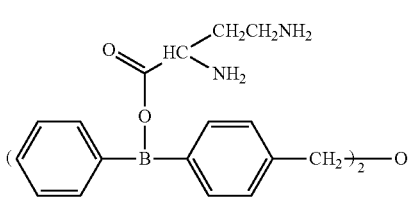
[Formula 136]

The entitled compound (35 mg) was obtained by allowing 26 mg of bis(4,4'-(phenylhydroxyboryl)benzyl) ether and 26 mg of 2,4-diaminobutyric acid to act in 1 mL of ethanol.

NMR (DMSO-$d_6$), 0.9 (m, 4H), 1.2-1.5 (m, 6H), 1.8-2.8 (m, 10H), 6.8-7.3 (m, 18H)

Example 136

Bis(4,4'-(phenyl-butylaminoethoxyboryl)benzyl) ether

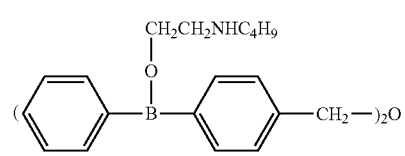
[Formula 137]

The entitled compound (35 mg) was obtained by allowing 40.6 mg of bis(4,4'-(phenylhydroxyboryl)benzyl) ether and 23 mg of N-n-butylethanolamine to act in 1 mL of ethanol.

NMR (CDCl$_3$), 0.83 (t, 6H), 1.21 (m, 4H), 1.45 (m, 4H), 2.83 (m, 4H), 4.01 (m, 4H), 4.51 (s, 4H), 7.2-7.6 (m, 18H)
CCE: 100% inhibition at 3 μM, 30% at 1 μM

Example 137

Bis(4,4'-(phenyl-phenylaminoethoxyboryl)benzyl) ether

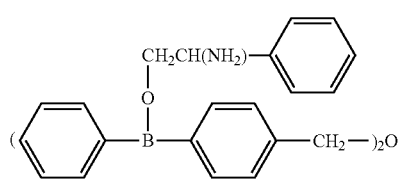

[Formula 138]

The entitled compound (43 mg) was obtained by allowing 40.6 mg of bis(4,4'-(phenylhydroxyboryl)benzyl) ether and 14 mg of phenylglycinol to act in 1 mL of ethanol.
NMR (CDCl$_3$), 4.12 (m, 2H), 4.36 (m, 4H), 4.41 (m, 4H), 7.15-7.55 (m, 18H)

Example 138

Bis(4,4'-(phenyl-benzylaminoethoxyboryl)benzyl) ether

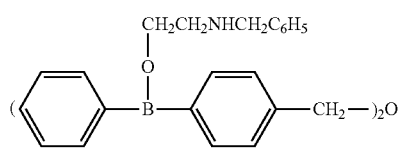

[Formula 139]

The entitled compound (43 mg) was obtained by allowing 41 mg of bis(4,4'-(phenylhydroxyboryl)benzyl) ether and 16 mg of benzylethanolamine to act in 1 mL of ethanol.
NMR (CDCl$_3$), 2.82 (m, 4H), 3.79 (m, 4H), 3.97 (m, 4H), 4.47 (s, 4H), 7.2-7.6 (m, 18H)

Example 139

Bis(4,4'-(phenyl-N-methylpiperidine-methoxyboryl)benzyl) ether

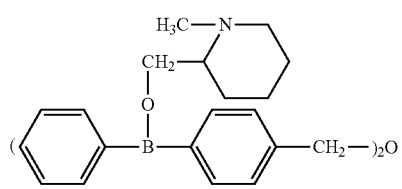

[Formula 140]

The entitled compound (40 mg) was obtained by allowing 41 mg of bis(4,4'-(phenylhydroxyboryl)benzyl) ether and 26 mg of N-methyl-piperidine-2-methanol to act in 1 mL of ethanol.

NMR (CDCl$_3$), 1.50-1.60 (m, 12H), 2.45 (m, 4H), 2.63 (m, 6H), 3.00 (m, 2H), 4.02 (m, 4H), 4.50 (m, 4H), 7.1-7.8 (m, 18H)
CCE: 100% inhibition at 3 μM, 40% inhibition at 1 μM

Example 140

Bis(4,4'-(phenyl-1-methyl-2-aminoethoxyboryl)benzyl) ether

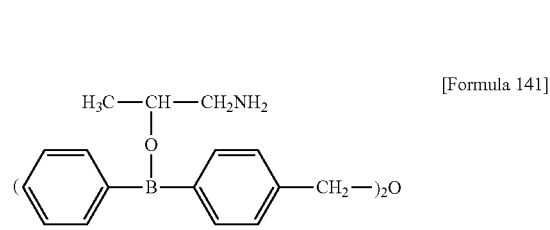

[Formula 141]

The entitled compound (40 mg) was obtained by allowing 41 mg of bis(4,4'-(phenylhydroxyboryl)benzyl) ether and 18 mg of 1-aminopropanol to act in 1 mL of ethanol.
NMR (CDCl$_3$), 1.18 (m, 6H), 1.92 (m, 4H), 3.65 (m, 2H), 3.80 (m, 4H), 4.50 (s, 4H), 7.1-7.5 (m, 18H)

Example 141

Bis(4,4'-(phenyl-1-piperidylethoxyboryl)benzyl) ether

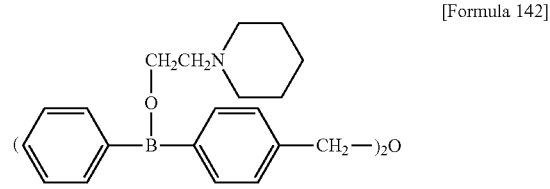

[Formula 142]

The entitled compound (22 mg) was obtained by allowing 41 mg of bis(4,4'-(phenylhydroxyboryl)benzyl) ether and 13 mg of 1-piperidineethanol to act in 1 mL of ethanol.
NMR (CDCl$_3$), 1.62 (m, 4H), 2.60 (m, 4H), 3.79 (m, 4H), 4.65 (s, 4H), 7.1-7.5 (m, 18H)

Example 142

Bis(3,3'-(phenyl-2-pyrrolidinomethoxyboryl)benzyl) ether

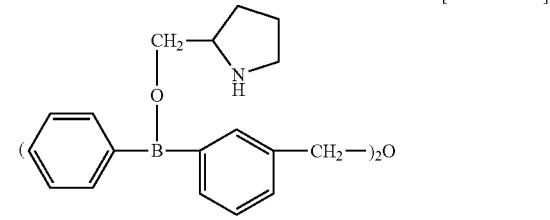

[Formula 143]

The entitled compound (33 mg) was obtained by allowing 41 mg of bis(3,3'-(phenylhydroxyboryl)benzyl) ether and 20 mg of 2-pyrrolidinemethanol to act in 0.4 mL of methanol.

NMR (CDCl$_3$), 1.4-2.0 (m, 8H), 2.4-2.9 (m, 6H), 4.4 (m, 4H), 4.5 (m, 4H), 7.1-7.5 (m, 18H)

Example 143

Bis(3,3'-(phenyl-aminothioethoxyboryl)benzyl) ether

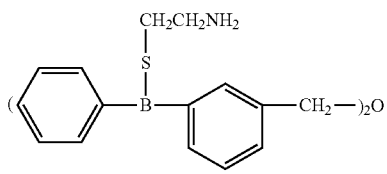

[Formula 144]

The entitled compound (18 mg) was obtained by allowing 41 mg of bis(3,3'-(phenylhydroxyboryl)benzyl) ether and 20 mg of 2-aminoethanethiol to act in 0.4 mL of methanol.
NMR (DMSO-d$_6$), 2.73 (m, 4H), 3.29 (m, 4H), 4.21 (m, 4H), 6.8-7.7 (m, 18H)

Example 144

Bis(3,3'-(phenyl-2-phenyl-2-aminoethoxyboryl)benzyl) ether

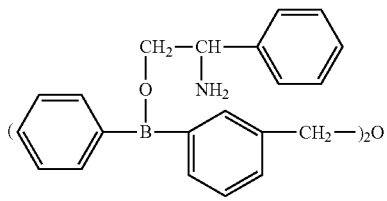

[Formula 145]

The entitled compound (40 mg) was obtained by allowing 41 mg of bis(3,3'-(phenylhydroxyboryl)benzyl) ether and 28 mg of phenylglycinol to act in 1 mL of methanol.
NMR (CDCl$_3$), 2.8-2.9 (m, 2H), 3.52 (m, 4H), 4.54 (m, 4H), 6.8-7.5 (m, 28H)

Example 145

Bis(3,3'-(phenyl-2-piperazylmethoxyboryl)benzyl) ether

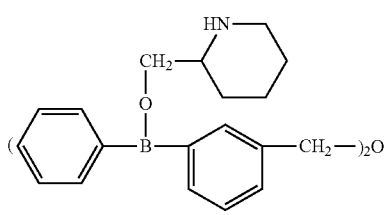

[Formula 146]

The entitled compound (42 mg) was obtained by allowing 41 mg of bis(3,3'-(phenylhydroxyboryl)benzyl) ether and 26 mg of piperidine-2-methanol to act in 1 mL of ethanol.

NMR (CDCl$_3$), 1.54 (m, 12H), 2.52 (m, 4H), 2.94 (m, 2H), 4.15 (m, 4H), 4.53 (s, 4H), 7.1-7.7 (m, 18H)

Example 146

Bis(3,3'-(phenyl-dimethylaminoethoxyboryl)benzyl) ether

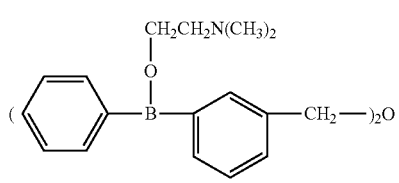

[Formula 147]

The entitled compound (45 mg) was obtained by allowing 41 mg of bis(3,3'-(phenylhydroxyboryl)benzyl) ether and 19 mg of dimethylaminoethanol to act in 1 mL of ethanol.
NMR (CDCl$_3$), 2.38 (s, 6H), 2.73 (m, 4H), 3.80 (m, 4H), 4.47 (m, 4H), 7.2-7.7 (m, 18H)

Example 147

Bis(3,3'-(phenyl-1-methyl-2-aminoethoxyboryl)benzyl) ether

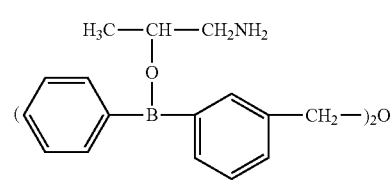

[Formula 148]

The entitled compound (42 mg) was obtained by allowing 41 mg of bis(3,3'-(phenylhydroxyboryl)benzyl) ether and 17 mg of 1-amino-2-propanol to act in 1 mL of ethanol.
NMR (CDCl$_3$), 1.31 (m, 6H), 2.4 (m, 4H), 3.8 (m, 2H), 4.58 (m, 4H), 7.1-7.4 (m, 18H)

Example 148

Bis(3,3'-(phenyl-2-piperidylethoxyboryl)benzyl) ether

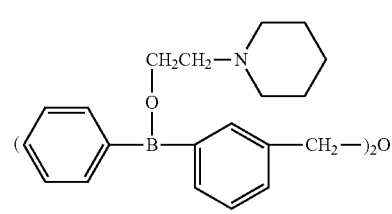

[Formula 149]

The entitled compound (36 mg) was obtained by allowing 41 mg of bis(3,3'-(phenylhydroxyboryl)benzyl) ether and 26 mg of 1-(2-hydroxyethyl)piperidine to act in 1 mL of ethanol.

NMR (CDCl$_3$), 1.43 (m, 4H), 1.63 (m, 8H), 2.83 (m, 12H), 3.43 (m, 4H), 4.54 (s, 4H), 7.2-7.8 (m, 18H)

Example 149

Bis(3,3'-(phenyl-2-pyridylmethoxyboryl)benzyl) ether

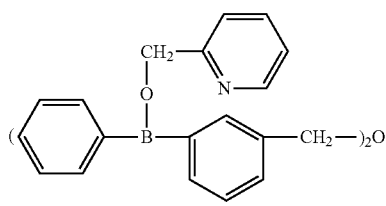

[Formula 150]

The entitled compound (46 mg) was obtained by allowing 41 mg of bis(3,3'-(phenylhydroxyboryl)benzyl) ether and 28 mg of 2-aminophenylethanol to act in 1 mL of ethanol.

NMR (CDCl$_3$), 4.47 (m, 4H), 5.30 (m, 4H), 7.0-8.2 (m, 26H)

Example 150

Bis(3,3'-(phenyl-2-amino-1-phenylethoxyboryl)benzyl) ether

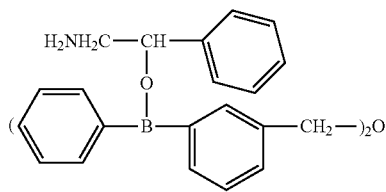

[Formula 151]

The entitled compound (46 mg) was obtained by allowing 41 mg of bis(3,3'-(phenylhydroxyboryl)benzyl) ether and 28 mg of 2-aminophenylethanol to act in 1 mL of ethanol.

NMR (CDCl$_3$), 2.5-2.9 (m, 4H), 4.12 (m, 2H), 5.52 (m, 4H), 6.8-7.8 (m, 28H)

CCE: 100% inhibition at 3 μM, 50% inhibition at 1 μM

Example 151

Bis(3,3'-(phenyl-N-methylethoxyboryl)benzyl) ether

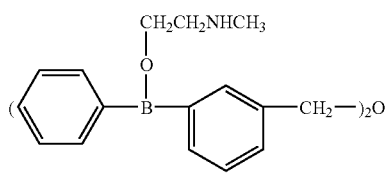

[Formula 152]

The entitled compound (16 mg) was obtained by allowing 41 mg of bis(3,3'-(phenylhydroxyboryl)benzyl) ether and 17 mg of N-methylethanolamine to act in 1 mL of ethanol.

NMR (CDCl$_3$), 2.07 (s, 6H), 2.72 (m, 4H), 3.85 (m, 4H), 4.49 (s, 4H), 7.0-7.7 (m, 18H)

CCE: 100% inhibition at 3 μM, 60% inhibition at 1 μM

Example 152

Bis(3,3'-(phenyl-N-aminoethyl-1-methyl-3-aminopropoxyboryl)benzyl) ether

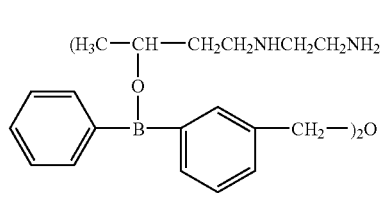

[Formula 153]

The entitled compound (50 mg) was obtained by allowing 41 mg of bis(3,3'-(phenylhydroxyboryl)benzyl) ether and 26 mg of N-(2-hydroxypropyl)ethylenediamine to act in 1 mL of ethanol.

NMR (CDCl$_3$), 1.20 (m, 4H), 1.9 (m, 6H), 2.6-3.0 (m, 12H), 4.09 (m, 3H), 5.1 (m, 4H), 7.0-7.6 (m, 18H)

CCE: 80% inhibition at 3 μM, 40% inhibition at 1 μM

Example 153

Bis(3,3'-(phenyl-glutamineboryl)benzyl) ether

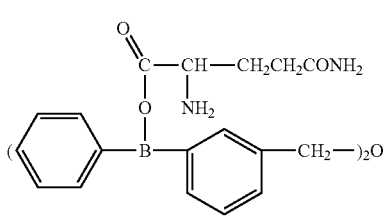

[Formula 154]

The entitled compound (52 mg) was obtained by allowing 41 mg of bis(3,3'-(phenylhydroxyboryl)benzyl) ether and 29 mg of glutamine to act in 1 mL of ethanol.

NMR (DMSO-d$_6$), 1.8-2.1 (m, 4H), 2.3 (m, 4H), 3.6-4.2 (m, 4H), 6.0-7.6 (m, 18H)

Example 154

Bis(3,3'-(phenyl-2,4-diaminobutyric acid boryl)benzyl) ether

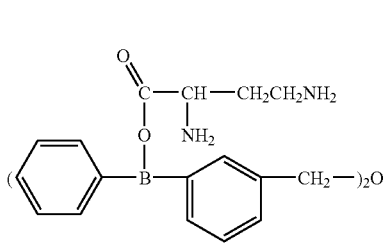

[Formula 155]

The entitled compound (17 mg) was obtained by allowing 41 mg of bis(3,3'-(phenylhydroxyboryl)benzyl) ether and 38 mg of 2,4-diaminobutyric acid to act in 1 mL of ethanol at 70° C.

NMR (DMSO-$d_6$), 2.18 (m, 4H), 2.98 (m, 4H), 3.77 (m, 4H), 4.50 (m, 4H), 6.8-7.6 (m, 18H)

Example 155

Bis(3,3'-(phenyl-N-butylaminoethylboryl)benzyl) ether

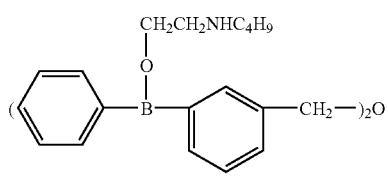

[Formula 156]

The entitled compound (38 mg) was obtained by allowing 44 mg of bis(3,3'-(phenylhydroxyboryl)benzyl) ether and 24 mg of N-butylethanolamine to act in 1 mL of ethanol.

NMR (CDCl$_3$), 0.81 (s, 6H), 1.15 (m, 4H), 1.40 (m, 4H), 2.50 (m, 4H), 2.91 (m, 4H), 3.99 (m, 4H), 4.52 (s, 4H), 7.2-7.6 (m, 18H)

CCE: 100% inhibition at 3 µM, 95% inhibition at 1 µM

Example 156

Bis(3,3'-(phenyl-asparagineboryl)benzyl) ether

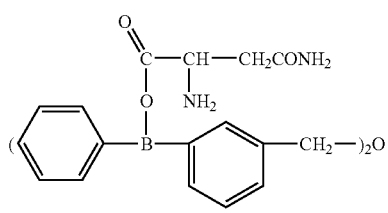

[Formula 157]

The entitled compound (23 mg) was obtained by allowing 41 mg of bis(3,3'-(phenylhydroxyboryl)benzyl) ether and 26 mg of asparagine to act in 1 mL of ethanol.

NMR (DMSO-$d_6$), 2.50 (m, 4H), 2.78 (m, 4H), 3.79 (m, 2H), 4.52 (m, 4H), 7.0-7.7 (m, 18H)

Example 157

Bis(3,3'-(phenyl-lysineboryl)benzyl) ether

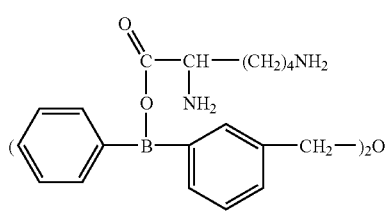

[Formula 158]

The entitled compound (50 mg) was obtained by allowing 41 mg of bis(3,3'-(phenylhydroxyboryl)benzyl) ether and 37 mg of lysine to act in 1 mL of ethanol.

NMR (DMSO-$d_6$), 1.24 (m, 8H), 2.28 (m, 4H), 2.49 (m, 2H), 4.3 (m, 4H), 6.8-7.7 (m, 18H)

Example 158

Bis(3,3'-(phenyl-ornithineboryl)benzyl) ether

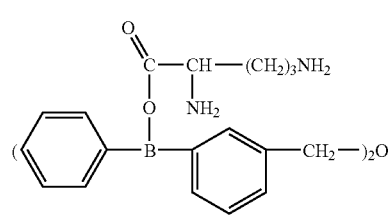

[Formula 159]

The entitled compound (54 mg) was obtained by allowing 41 mg of bis(3,3'-(phenylhydroxyboryl)benzyl) ether and 44 mg of ornithine to act in 1 mL of ethanol.

NMR (DMSO-$d_6$), 1.50 (m, 4H), 1.79 (m, 4H), 2.42 (m, 2H), 3.85 (m, 4H), 4.42 (m, 4H), 6.8-7.7 (m, 18H)

Example 159

Bis(4,4'-(phenyl-2-methyl-8-quinolinooxyboryl)phenyl) ether

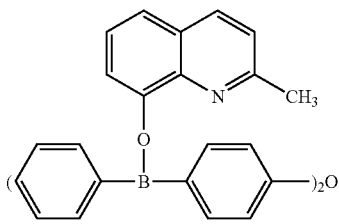

[Formula 160]

The entitled compound (25 mg) was obtained by allowing 32 mg of bis(4,4'-(phenylhydroxyboryl)phenyl) ether and 27 mg of 2-methyl-8-hydroxyquinoline to act in 1 mL of ethanol.

NMR (CDCl$_3$), 3.72 (s, 6H), 7.0-8.3 (m, 28H)

Example 160

Bis(4,4'-(phenyl-2-pyridylmethoxyboryl)phenyl) ether

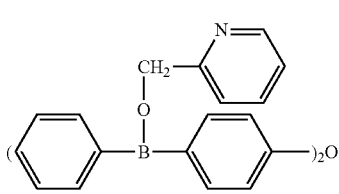

[Formula 161]

The entitled compound (28 mg) was obtained by allowing 68 mg of bis(4,4'-(phenylhydroxyboryl)phenyl) ether and 39 mg of 2-pyridylmethanol to act in 1 mL of ethanol.

NMR (CDCl$_3$), 5.30 (s, 4H), 6.9-8.4 (m, 26H)

CCE: 100% inhibition at 10 μM, 0% inhibition at 3 μM

Example 161

Bis(4,4'-(phenyl-2-benzyl-2-amino-ethoxyboryl) benzyl) ether

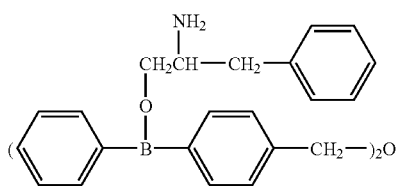

[Formula 162]

The entitled compound (9 mg) was obtained by allowing 41 mg of bis(4,4'-(phenylhydroxyboryl)benzyl) ether and 10 mg of 2-amino-3-phenylpropanol to act in 1 mL of ethanol.

NMR (CDCl$_3$), 1.92 (m, 4H), 2.76 (m, 2H), 3.98 (m, 4H), 4.49 (m, 4H), 7.7-7.5 (m, 18H)

Example 162

Bis(4,4'-(phenyl-2-benzyl-2-amino-ethoxyboryl) phenyl) ether

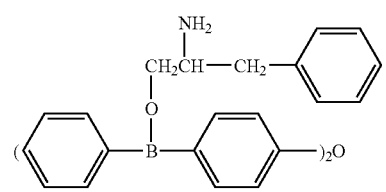

[Chemical 163]

The entitled compound (73 mg) was obtained by allowing 77 mg of bis(4,4'-(phenylhydroxyboryl)phenyl) ether and 75 mg of 2-amino-3-phenylpropanol to act in 1 mL of acetonitrile.

NMR (CDCl$_3$), 2.50 (m, 4H), 2.75 (m, 2H), 4.45 (m, 4H), 7.0-7.7 (m, 28H)

Example 163

Bis(3,3'-(phenyl-2-benzyl-2-amino-ethoxyboryl) benzyl) ether

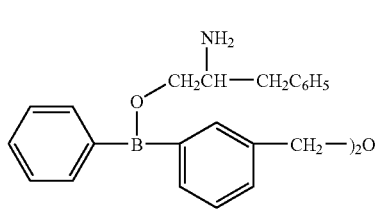

[Formula 164]

The entitled compound (6 mg) was obtained by allowing 34 mg of bis(3,3'-(phenylhydroxyboryl)benzyl) ether and 26 mg of 2-amino-3-phenylpropanol to act in 1 mL of ethanol.

NMR (CDCl$_3$), 1.96 (m, 4H), 2.35 (m, 2H), 3.00 (2H), 3.34 (m, 2H), 4.50 (m, 4H), 4.64 (m, 4H), 6.8-7.4 (m, 28H)

Example 164

Bis(4,4'-(phenyl-2-phenyl-2-amino-ethoxyboryl) benzyl) ether

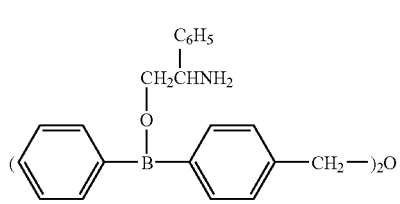

[Formula 165]

The entitled compound (12 mg) was obtained by allowing 52 mg of bis(4,4'-(phenylhydroxyboryl)phenyl) ether and 27 mg of 2-amino-3-phenylpropanol to act in 0.5 mL of ethanol.

NMR (CDCl$_3$), 1.74 (m, 4H), 3.35 (m, 2H), 4.00 (m, 4H), 4.52 (m, 4H), 7.0-7.7 (m, 28H)

CCE: 100% inhibition at 10 μM, 100% inhibition at 3 μM

INDUSTRIAL APPLICABILITY

The bisboron compound of the present invention is a drug effectively reducing the intracellular calcium concentration abnormally increased by IP$_3$ receptor activation or capacitative calcium entry, and thus has an action of strongly inhibiting an increase in the intracellular calcium concentration. Therefore, the compound can be used as a prophylactic and/or therapeutic agent for various diseases caused by an increase in the intracellular calcium concentration, for example, diseases requiring control of vasoconstriction or vascular permeability; control of the respiratory tract; adjustment of gastrointestinal tract movement, neuronal differentiation or nerve growth cone; and control of pheromone reception, smooth muscle contraction or the like, specifically, diseases such as ischemic heart or brain disease, cardiac hypertrophy, renal disease, hypertension, cerebral vasospasm, pancreatitis, asthma, immunodeficiency, allergic disease and Alzheimer's disease.

The invention claimed is:
1. A bisboron compound having activity to control the intracellular calcium concentration represented by the general formula (I):

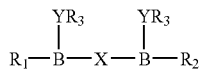

wherein B represents a boron atom,
Y represents an oxygen or sulfur atom,
$R_1$ and $R_2$ independently represent a monocyclic aromatic group, a polycyclic aromatic group, or a heterocyclic group containing at least one heteroatom selected from oxygen, nitrogen and sulfur atoms,
$R_3$ represents a hydrogen atom; —$(CH_2)_2$—$NR_4R_5$, wherein $R_4$ and $R_5$ independently represent a hydrogen atom, or C1-C4 alkyl substituted or unsubstituted with amino, mono- or di-C1-C4 alkylamino or phenyl group, or $R_4$ and $R_5$ are taken together with the nitrogen atom to which they are bonded to form a 5- or 6-membered cyclic ring; —CO—$(CH_2)_m$—$NR_4R_5$, wherein m represents an integer of 1 to 4, and $R_4$ and $R_5$ are as defined above; —$COCH(NH_2)R_6$, wherein $R_6$ represents an amino acid residue or —$(CH_2)_nNH_2$, wherein n represents an integer of 1 to 3; —$CHR_7R_8$, wherein $R_7$ and $R_8$ independently represent C1-C4 alkyl substituted or unsubstituted with amino, mono- or di-(amino group-substituted or unsubstituted C1-C4 alkyl)amino or phenyl group, pyridyl, or phenyl substituted with C1-C3 alkoxy group; —$CH_2CH(NH_2)$—$R_9$, wherein $R_9$ represents phenyl, or C1-C4 alkyl substituted with phenyl group; quinolyl or isoquinolyl substituted with C1-C4 alkyl group; or C1-C4 alkyl substituted with pyridyl, piperidino or pyrrolidinyl group, and
X represents a bifunctional group having a monocyclic aromatic group, polycyclic aromatic group or heterocyclic group bonded to each side of a group selected from $CH_2OCH_2$, and $CH_2OCH_2CH_2$,
or a salt thereof,
provided that bis[2-(hydroxyphenylboryl)benzyl]ether, 1,4-bis[4-(hydroxyphenylboryl)phenoxy)butane, bis[4-(hydroxyphenylboryl)benzyl]ether, bis[2-[(2-aminoethoxy)phenylboryl]benzyl]ether, bis[4-((2-aminoethoxy)phenylboryl]benzyl]ether, [4-[(2-aminoethoxy)phenylboryl]benzyl][2-[4-[(2-aminoethoxy)phenylboryl]phenyl]ethyl]ether, [2-[(2-aminoethoxy)phenylboryl]benzyl][2-[4-[(2-aminoethoxy)phenylboryl]phenyl]ethyl]ether and salts thereof are excluded.
2. The bisboron compound or salt thereof according to claim 1, wherein the monocyclic aromatic group or polycyclic aromatic group is an aromatic group substituted or unsubstituted with at least one substituent selected from the group consisting of halogen, halogenated C1-C4 alkyl, cyano, hydroxy, sulfanyl, amino, nitro, mono- or di-C1-C4 alkylamino, carboxyl, C1-C4 alkylcarbonyl, C1-C4 alkylcarbonyloxy, C2-C4 alkenyl, C2-C4 alkynyl, cycloalkyl, cycloalkenyl, C1-C4 alkyl, C1-C4 alkylthio, C1-C4 alkoxy, aryl, amide and C1-C4 alkylamide.
3. The bisboron compound or salt thereof according to claim 1, wherein the heterocyclic group is a 5- to 15-membered heterocyclic group substituted or unsubstituted with at least one substituent selected from the group consisting of halogen, cyano, hydroxy, sulfanyl,amino, nitro, mono- or di-C1-C4 alkylamino, carboxyl, C1-C4 alkylcarbonyl, C1-C4 alkylcarbonyloxy, C2-C4 alkenyl, C2-C4 alkynyl, cycloalkyl, cycloalkenyl, C1-C4 alkyl, C1-C4 alkylthio, C1-C4 alkoxy, aryl, amide and C1-C4 alkylamide.
4. The bisboron compound or salt thereof according to claim 1, wherein the X is a group selected from the group consisting of the following groups

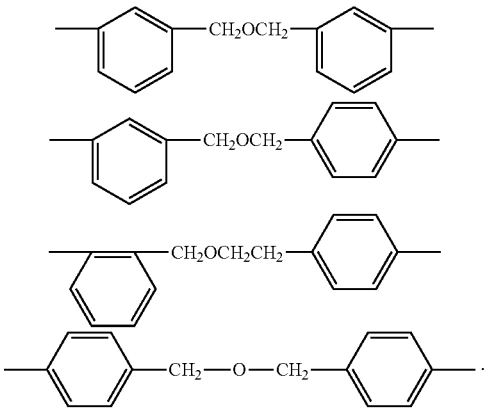

5. The bisboron compound or salt thereof according to claim 1, wherein the X is substituted or unsubstituted, dibenzyl ether, or benzyl phenethyl ether having a meta-meta, ortho-ortho, para-para, meta-para, meta-ortho or ortho-para orientation.
6. The bisboron compound or salt thereof according to claim 5, wherein the X is dibenzyl ether having any of meta-meta, ortho-para, ortho-meta and meta-para orientations.
7. The bisboron compound or salt thereof according to claim 6, wherein the X is dibenzyl ether having a meta-meta orientation.
8. The bisboron compound or salt thereof according to claim 5, wherein the X is benzyl phenethyl ether having any of meta-meta, ortho-ortho, ortho-meta and meta-para orientations.
9. The bisboron compound or salt thereof according to claim 8, wherein the X is benzyl phenethyl ether having a meta-meta or ortho-ortho orientation.
10. The bisboron compound or salt thereof according to claim 1, wherein the $R_1$ and $R_2$ are independently a substituted or unsubstituted phenyl or phenylene group.
11. The bisboron compound or salt thereof according to claim 1, wherein the $R_3$ is a hydrogen atom or a 2-aminoethyl group.
12. The bisboron compound or salt thereof according to claim 1, wherein the Y is an oxygen atom.
13. The bisboron compound according to claim 1, wherein the compound is selected from the group consisting of:
bis(4,4'-(3-chloro-4-methylphenylhydroxyboryl)benzyl) ether;
bis(3,3'-(phenylhydroxyboryl)benzyl) ether;
bis(3,3'-(phenylaminoethoxyboryl)benzyl) ether;
bis(4-(4-trifluoromethylphenylhydroxyboryl)benzyl) ether;
bis(4-(1-naphthylhydroxyboryl)benzyl) ether;
bis(4-(fluorophenylhydroxyboryl)benzyl) ether;
bis(3-(4-methoxyphenylhydroxyboryl)benzyl) ether;
(3-(phenylhydroxyboryl)benzyl) (4-(phenylhydroxyboryl)benzyl) ether;
(2-(phenylhydroxyboryl)benzyl) (3-(phenylhydroxyboryl)benzyl) ether;

(2-(phenylhydroxyboryl)benzyl) (4-(phenylhydroxyboryl)benzyl) ether;
(3-(phenylaminoethoxyboryl)benzyl) (4-(phenylaminoethoxyboryl)benzyl) ether;
bis(3-(3-chloro-4-methylphenylhydroxyboryl)benzyl) ether;
(2-(phenylaminoethoxyboryl)benzyl) (3-(phenylaminoethoxyboryl)benzyl) ether;
2-(phenylaminoethoxyboryl)benzyl) (4-(phenylaminoethoxyboryl)benzyl) ether;
bis(3-(4-fluorophenylhydroxyboryl)benzyl) ether;
bis(3-(4-fluorophenylaminoethoxyboryl)benzyl) ether;
bis(4-(4-chloro-3-methyl-phenylhydroxyboryl)benzyl) ether;
bis(4-(4-chloro-3-methyl-phenylaminoethoxyboryl)benzyl) ether;
bis(3-(3',4'-methylenedioxy-phenylhydroxyboryl)benzyl) ether;
(3-(3-chloro-4-methylphenylhydroxyboryl)benzyl) (4-(3-chloro-4-methylphenylhydroxyboryl)benzyl) ether;
(3-(3',4',5'-trifluorophenylhydroxyboryl)benzyl) (4-(3',4',5'-trifluorophenylhydroxyboryl)benzyl) ether;
bis(3-(4-methoxyphenylaminoethoxyboryl)benzyl) ether;
(3-(4-chloro-3-methylphenylhydroxyboryl)benzyl) (2-(4-chloro-3-methylphenylhydroxyboryl)benzyl) ether;
bis(3-(4-cyanophenylhydroxyboryl)benzyl) ether;
bis(3-(2'-thiophenylhydroxyboryl)benzyl) ether;
bis(3-(1'-naphthylhydroxyboryl)benzyl) ether;
bis(3-(2'-thiophenylhydroxyboryl)benzyl) ether;
bis(4-(2-methoxy-5-fluorophenylhydroxyboryl)benzyl) ether;
bis(4-(3,4-difluorophenylhydroxyboryl)benzyl) ether;
bis(4-(3,4-difluorophenylaminoethoxyboryl)benzyl) ether;
bis(4-(4-methylphenylhydroxyboryl)benzyl) ether;
bis(4-(4-methylphenylaminoethoxyboryl)benzyl) ether;
(2-(phenylhydroxyboryl)phenethyl) ((2-phenylhydroxyboryl)benzyl) ether;
(2-(phenylhydroxyboryl)phenethyl) ((2-phenylaminoethoxyboryl)benzyl) ether;
bis(3-(1-naphthylaminoethoxyboryl)benzyl) ether;
bis(4,4'-(phenyl-N,N-dimethylaminoethoxyboryl)benzyl) ether;
bis(4,4'-(phenyl-N-aminoethylaminoethoxyboryl)benzyl) ether;
bis(4,4'-(phenyl-N-methylaminoethoxyboryl)benzyl) ether;
bis(3,3'-(phenyl-N,N-dimethylaminoethoxyboryl)benzyl) ether;
bis(3,3'-(phenyl-asparagineboryl)benzyl) ether;
bis(3,3'-(phenyl-aminothioethoxyboryl)benzyl) ether;
bis(4,4'-(phenyl-2-pyridylmethoxyboryl)benzyl) ether;
bis(4,4'-(p-trifluoromethylphenyl-hydroxyboryl)benzyl) ether;
bis(4,4'-(3-chloro-4-methylphenyl-hydroxyboryl)benzyl) ether;
bis(4,4'-(phenyl-lysineboryl)benzyl) ether;
bis(4,4'-(p-methoxymethyl-phenyl-hydroxyboryl)benzyl) ether;
bis(4,4'-(3,4-difluorophenyl-hydroxyboryl)benzyl) ether;
bis(4,4'-(p-methoxyphenyl-aminoethoxyboryl)benzyl) ether;
bis(4,4'-(p-methoxyphenyl-N-methylaminoethoxyboryl)benzyl) ether;
bis(4,4'-(p-methoxyphenyl-N,N-dimethylaminoethoxyboryl)benzyl) ether;
bis(4,4'-(p-methoxyphenyl-2,4-diaminobutyric acid boryl)benzyl) ether;
bis(4,4'-(3,4-difluorophenyl-aminoethoxyboryl)benzyl) ether;
bis(4,4'-(3,4-difluorophenyl-N-methylaminoethoxyboryl)benzyl) ether;
bis(4,4'-(3,4-difluorophenyl-N,N-dimethylaminoethoxyboryl)benzyl) ether;
bis(4,4'-(3,4-difluorophenyl-N-aminoethylaminoethoxyboryl)benzyl) ether;
bis(4,4'-(3-chloro-4-methylphenyl-aminoethoxyboryl)benzyl) ether;
bis(4,4'-(3-chloro-4-methylphenyl-N-methylaminoethoxyboryl)benzyl) ether;
bis(4,4'-(3-chloro-4-methylphenyl-N,N-dimethylaminoethoxyboryl)benzyl) ether;
bis(4,4'-(3-chloro-4-methylphenyl-2-piperidylmethyloxyboryl)benzyl) ether;
bis(4,4'-(p-trifluoromethylphenyl-N,N-dimethylaminoethoxyboryl)benzyl) ether;
bis(4,4'-(p-trifluoromethylphenyl-asparagineboryl)benzyl) ether;
bis(4,4'-(p-trifluoromethylphenyl-aminoethoxyboryl)benzyl) ether;
bis(4,4'-(phenyl-2-amino-1-phenylethoxyboryl)benzyl) ether;
bis(4,4'-(phenyl-aminothioethoxyboryl)benzyl) ether;
bis(4,4'-(phenyl-2-pyrrolidinemethoxyboryl)benzyl) ether;
bis(4,4'-(phenyl-2,4-diaminobutyric acid boryl)benzyl) ether;
bis(4,4'-(phenyl-butylaminoethoxyboryl)benzyl) ether;
bis(4,4'-(phenyl-phenylaminoethoxyboryl)benzyl) ether;
bis(4,4'-(phenyl-benzylaminoethoxyboryl)benzyl) ether;
bis(4,4'-(phenyl-N-methylpiperidine-methoxyboryl)benzyl) ether;
bis(4,4'-(phenyl-1-methyl-2-aminoethoxyboryl)benzyl) ether;
bis(4,4'-(phenyl-1-piperidylethoxyboryl)benzyl) ether;
bis(3,3'-(phenyl-2-pyrrolidinomethoxyboryl)benzyl) ether;
bis(3,3'-(phenyl-aminothioethoxyboryl)benzyl) ether;
bis(3,3'-(phenyl-2-phenyl-2-aminoethoxyboryl)benzyl) ether;
bis(3,3'-(phenyl-2-piperazylmethoxyboryl)benzyl) ether;
bis(3,3'-(phenyl-dimethylaminoethoxyboryl)benzyl) ether;
bis(3,3'-(phenyl-1-methyl-2-aminoethoxyboryl)benzyl) ether;
bis(3,3'-(phenyl-2-piperidylethoxyboryl)benzyl) ether;
bis(3,3'-(phenyl-2-pyridylmethoxyboryl)benzyl) ether;
bis(3,3'-(phenyl-2-amino-1-phenylethoxyboryl)benzyl) ether;
bis(3,3'-(phenyl-N-methylethoxyboryl)benzyl) ether;
bis(3,3'-(phenyl-N-aminoethyl-1-methyl-3-aminopropoxyboryl)benzyl) ether;
bis(3,3'-(phenyl-glutamineboryl)benzyl) ether;
bis(3,3'-(phenyl-2,4-diaminobutyric acid boryl)benzyl) ether;
bis(3,3'-(phenyl-N-butylaminoethylboryl)benzyl) ether;
bis(3,3'-(phenyl-asparagineboryl)benzyl) ether;
bis(3,3'-(phenyl-lysineboryl)benzyl) ether;
bis(3,3'-(phenyl-ornithineboryl)benzyl) ether;
bis(4,4'-(phenyl-2-benzyl-2-amino-ethoxyboryl)benzyl) ether;
bis(3,3'-(phenyl-2-benzyl-2-amino-ethoxyboryl)benzyl) ether;

bis(4,4'-(phenyl-2-phenyl-2-amino-ethoxyboryl)benzyl) ether; and salts thereof.

14. A composition comprising the bisboron compound or salt thereof according to claim 1.

15. A method for alleviation or treatment of a disease associated with an increase in intracellular calcium concentration comprising administering a therapeutically effective amount of the composition of claim 14, to a subject in need thereof.

16. A method for reducing release of endogenous calcium and/or entry of capacitative calcium comprising administering an effective amount of the composition according to claim 14, to reduce release of endogenous calcium and/or entry of capacitative calcium.

17. The method according to claim 15, wherein the disease is selected from the group consisting of ischemic heart or brain disease, cardiac hypertrophy, renal disease, hypertension, cerebral vasospasm, pancreatitis, asthma, immunodeficiency, allergic disease, and Alzheimer's disease.

* * * * *